US009101327B2

(12) United States Patent
Ho et al.

(10) Patent No.: US 9,101,327 B2
(45) Date of Patent: Aug. 11, 2015

(54) DEVICES, SYSTEMS, AND METHODS FOR CONTROLLING FIELD OF VIEW IN IMAGING SYSTEMS

(71) Applicant: Volcano Corporation, San Diego, CA (US)

(72) Inventors: Dietrich Ho, Mountain View, CA (US); Elizabeth Begin, Billerica, MA (US); Oren Levy, Emerald Hills, CA (US); Jason Sproul, Watertown, MA (US); Stan Thomas, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/679,688

(22) Filed: Nov. 16, 2012

(65) Prior Publication Data

US 2013/0137985 A1     May 30, 2013

Related U.S. Application Data

(63) Continuation of application No. 13/665,470, filed on Oct. 31, 2012.

(60) Provisional application No. 61/553,772, filed on Oct. 31, 2011, provisional application No. 61/553,789, filed on Oct. 31, 2011.

(51) Int. Cl.
*A61B 8/00*      (2006.01)
*A61M 25/00*    (2006.01)
(Continued)

(52) U.S. Cl.
CPC .............. *A61B 8/54* (2013.01); *A61B 1/00006* (2013.01); *A61B 1/0008* (2013.01); *A61B 1/00009* (2013.01); *A61B 8/4461* (2013.01); *A61B 8/4466* (2013.01); *A61M 25/0068* (2013.01); *A61M 25/0105* (2013.01); *A61M 25/0108* (2013.01); *A61B 1/0058* (2013.01); *A61B 1/00096* (2013.01); *A61B 1/00172* (2013.01); *A61B 1/00183* (2013.01); *A61B 1/05* (2013.01);
(Continued)

(58) Field of Classification Search
USPC .......................................... 600/445, 459, 463
See application file for complete search history.

(56) References Cited

U.S. PATENT DOCUMENTS

| 5,379,772 | A | 1/1995 | Imran |
| 2007/0016062 | A1 | 1/2007 | Park et al. |

(Continued)

OTHER PUBLICATIONS

Diagnostic Ultrasound: Imaging and Blood Flow Measurements by Shung, published 2006 by CRC press Taylor and Francis Group.*

(Continued)

*Primary Examiner* — Katherine Fernandez
*Assistant Examiner* — Michael Kellogg
(74) *Attorney, Agent, or Firm* — Haynes and Boone, LLP

(57) ABSTRACT

Devices, systems, and methods for controlling the field of view in imaging systems are provided. For example, in one embodiment an imaging system includes a flexible elongate member sized and shaped for use within an internal structure of a patient, an imaging transducer positioned within the distal portion of the flexible elongate member, an imaging marker positioned to be detectable within a field of view of the imaging transducer, and a controller in communication with the flexible elongate member and configured to adjust a control signal of the flexible elongate member based on the detection of the imaging marker in data received from the flexible elongate member in order to achieve a desired field of view for the imaging transducer.

32 Claims, 34 Drawing Sheets

(51) Int. Cl.
- A61M 25/01 (2006.01)
- A61B 1/00 (2006.01)
- *A61B 1/005* (2006.01)
- *A61B 19/00* (2006.01)
- *A61B 1/05* (2006.01)
- *A61B 1/313* (2006.01)
- *A61B 8/12* (2006.01)
- *A61B 8/08* (2006.01)
- *G01S 15/89* (2006.01)

(52) U.S. Cl.
CPC .............. *A61B 1/3137* (2013.01); *A61B 8/0883* (2013.01); *A61B 8/0891* (2013.01); *A61B 8/12* (2013.01); *A61B 8/445* (2013.01); *A61B 8/4483* (2013.01); *A61B 8/4494* (2013.01); *A61B 8/52* (2013.01); *A61B 8/543* (2013.01); *A61B 8/58* (2013.01); *A61B 8/585* (2013.01); *A61B 2019/5287* (2013.01); *A61B 2019/5425* (2013.01); *G01S 15/894* (2013.01)

(56) References Cited

U.S. PATENT DOCUMENTS

| | | |
|---|---|---|
| 2009/0264768 A1 | 10/2009 | Brian et al. |
| 2011/0218437 A1* | 9/2011 | Park et al. ............ 600/443 |
| 2011/0263986 A1 | 10/2011 | Park et al. |
| 2013/0178746 A1* | 7/2013 | Ho et al. ............ 600/463 |

OTHER PUBLICATIONS

International Search Report and Written Opinion received in Patent Cooperation Treaty Application No. PCT/US2012/062821, dated Mar. 18, 2013, 10 pages.

\* cited by examiner

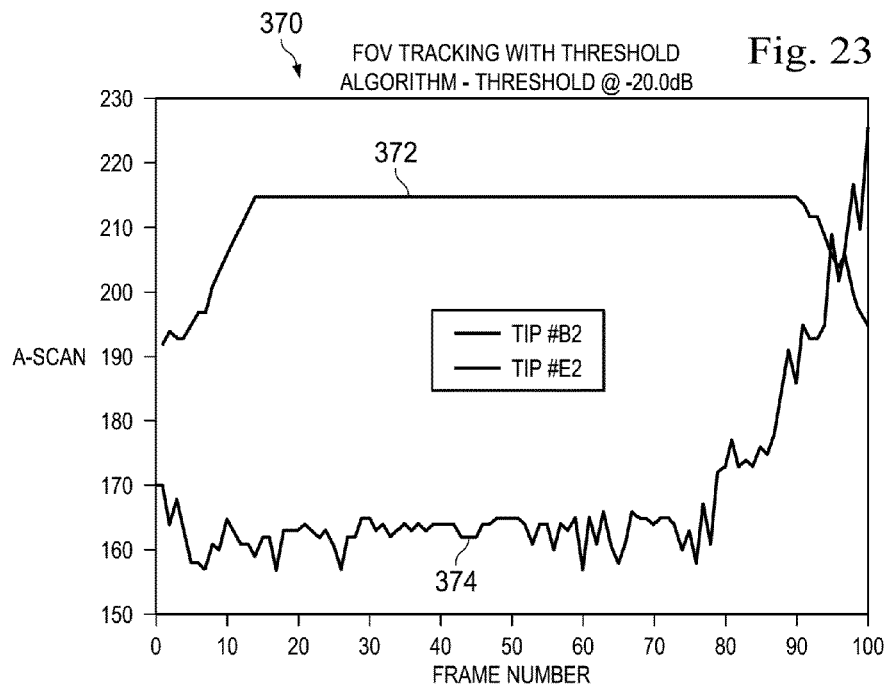
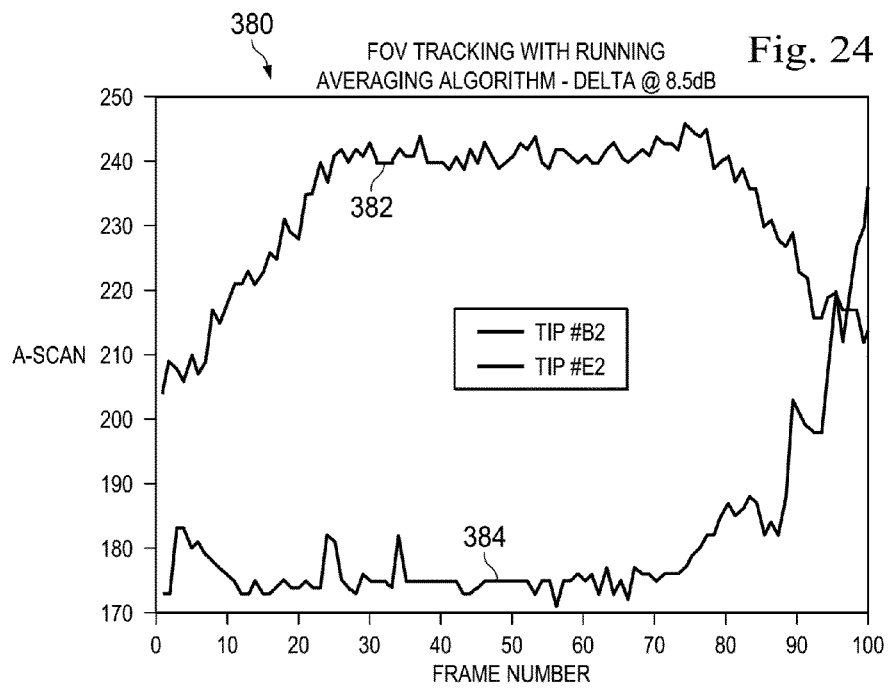

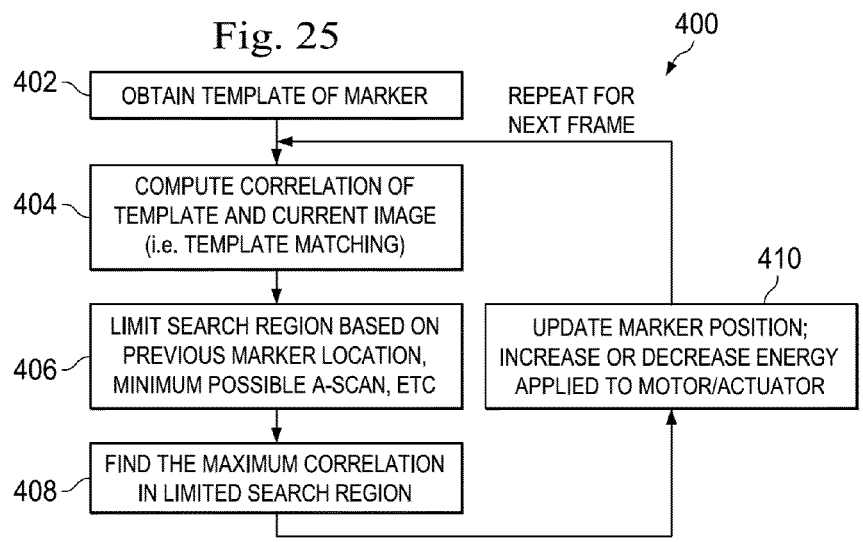
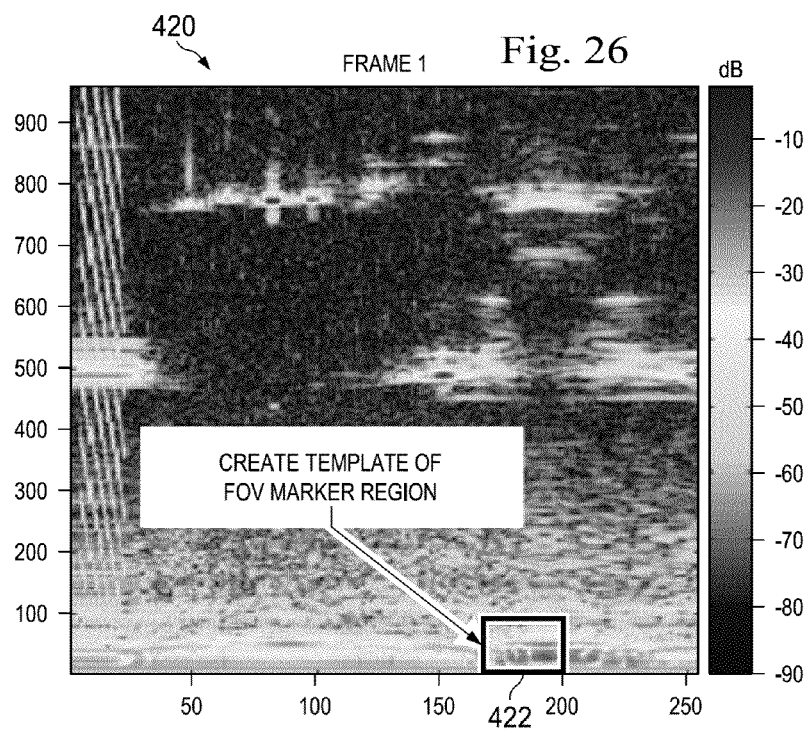

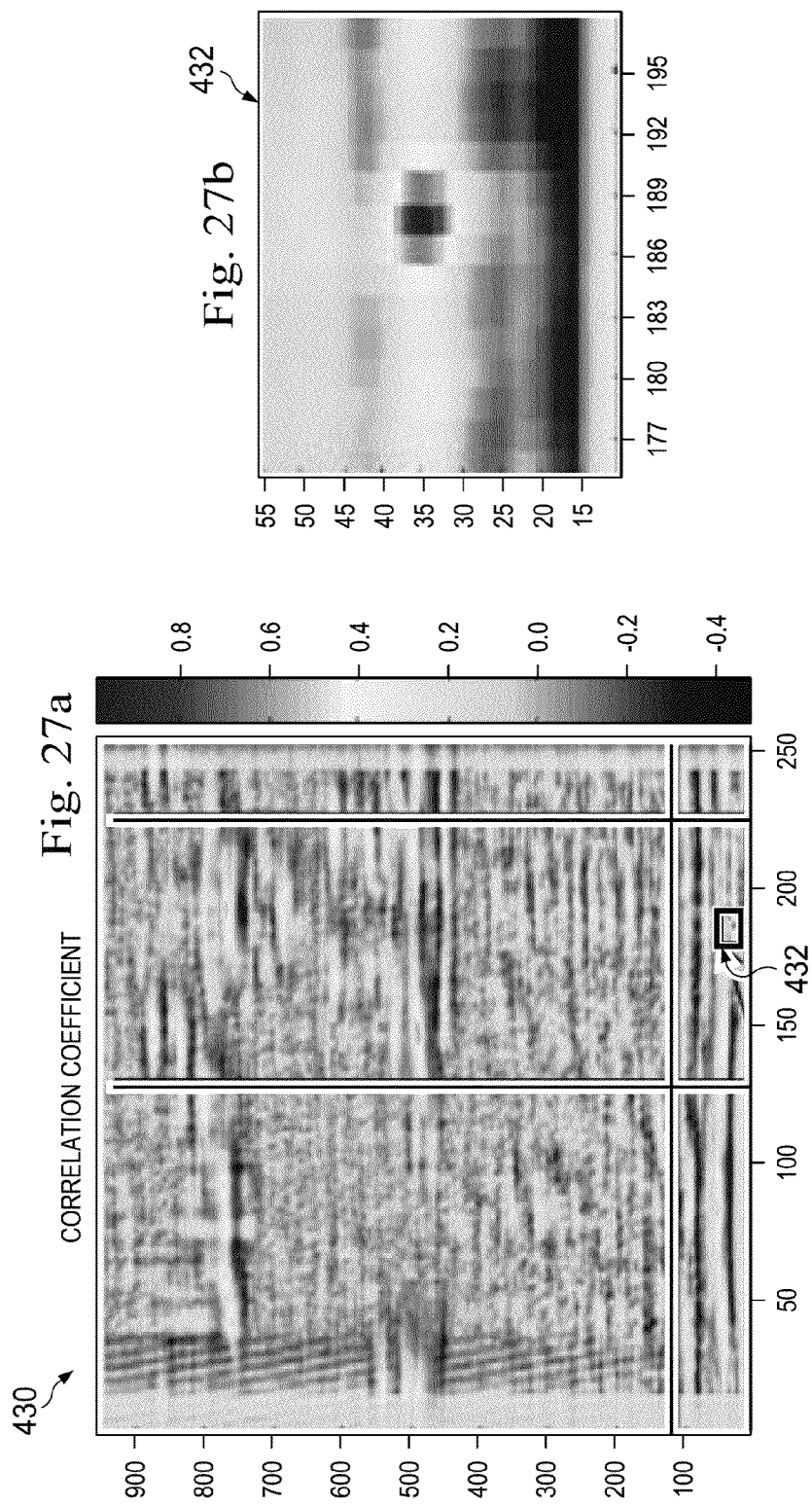

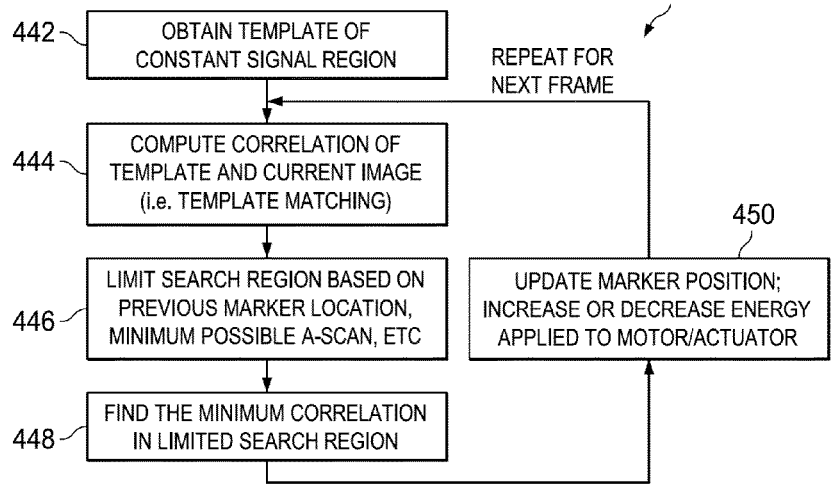
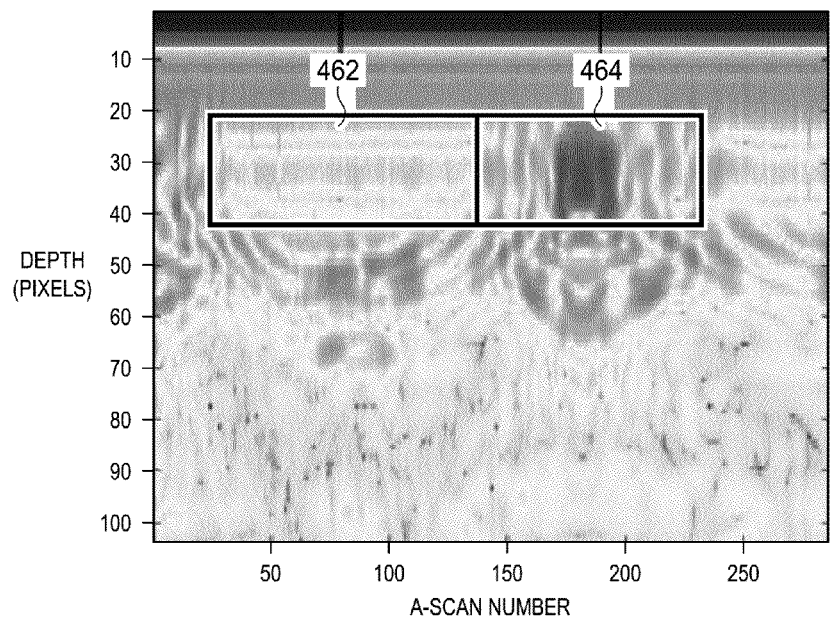

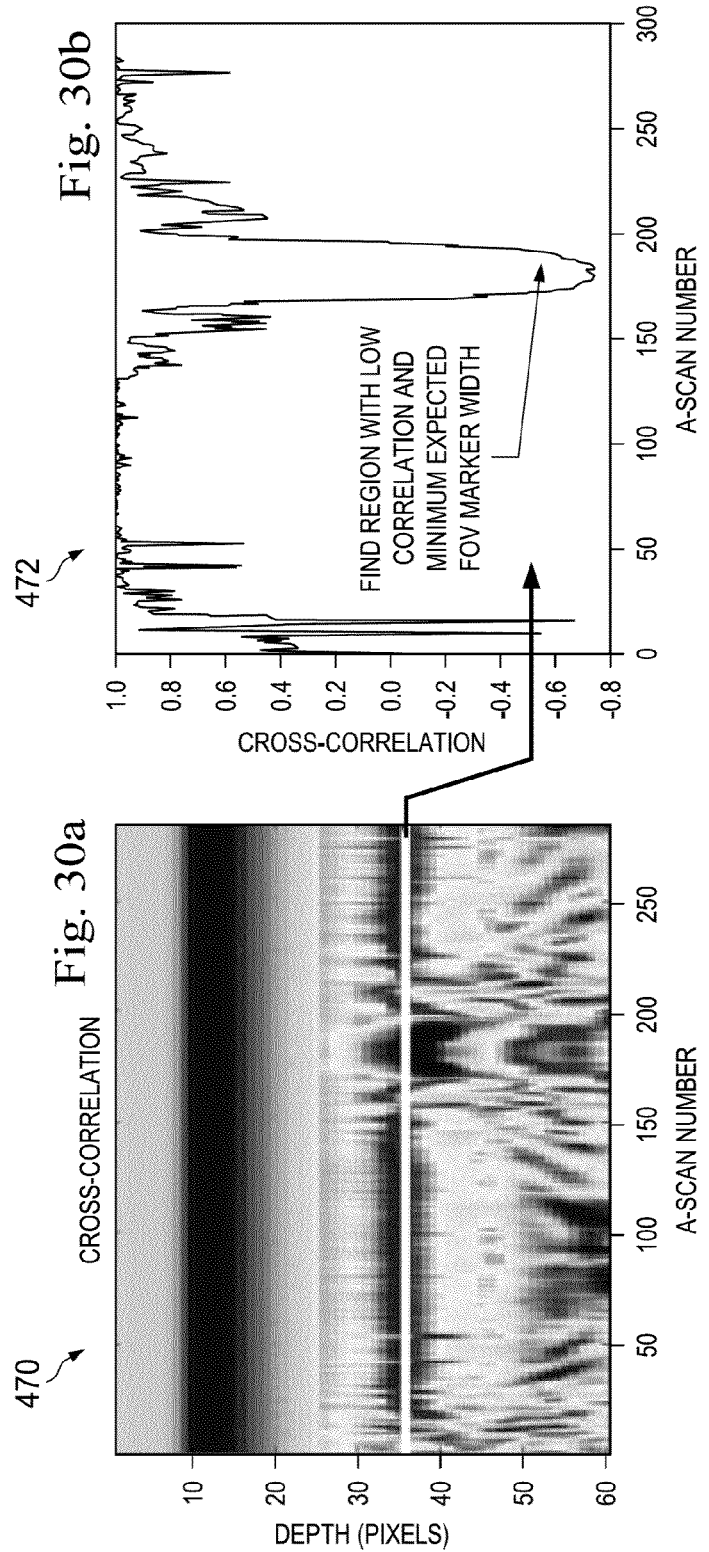

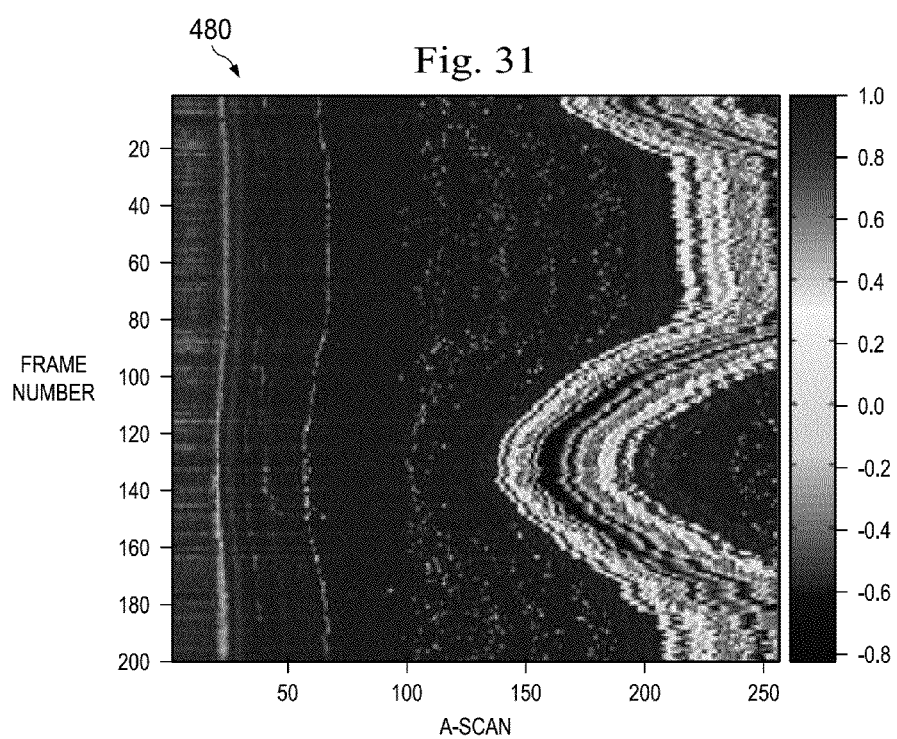

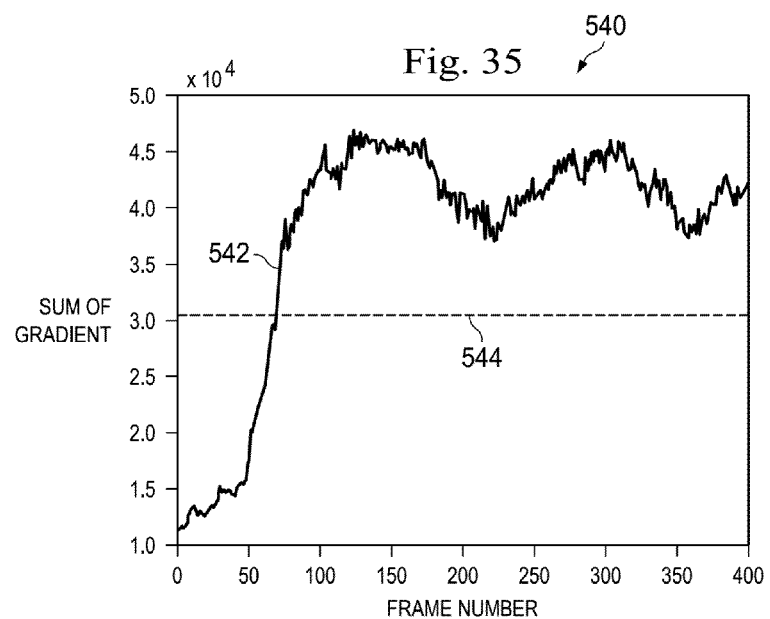
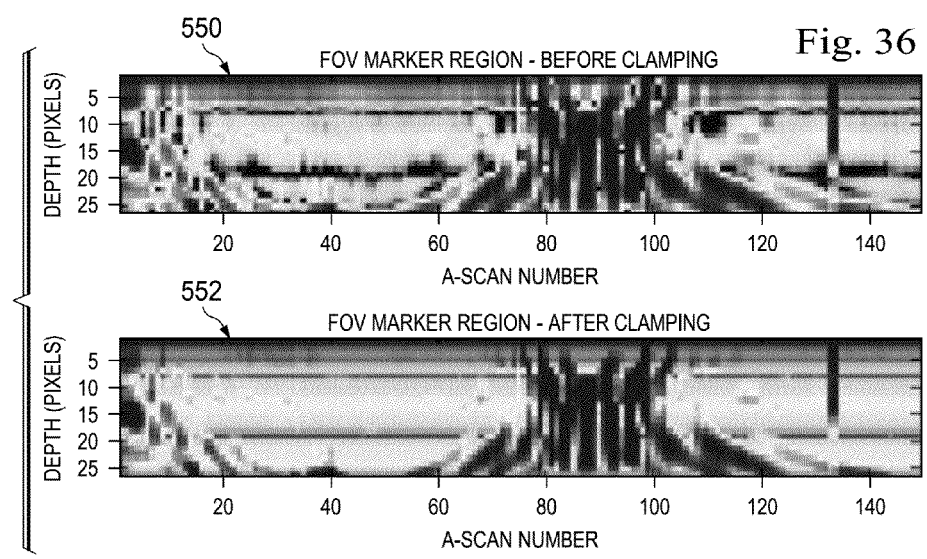

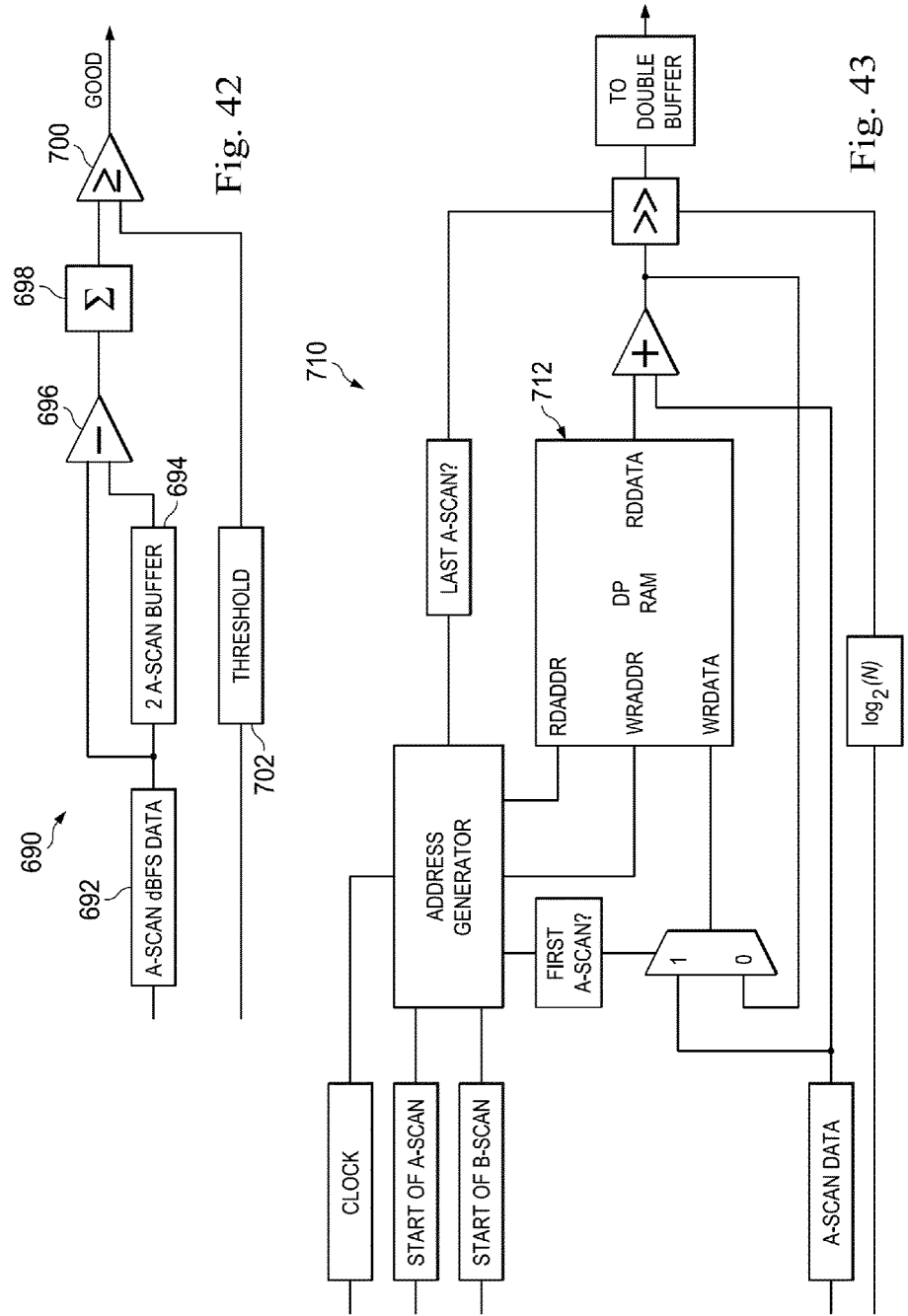

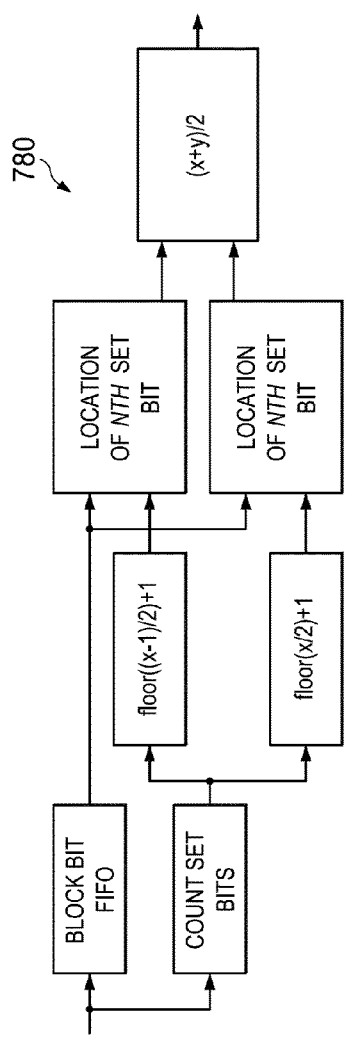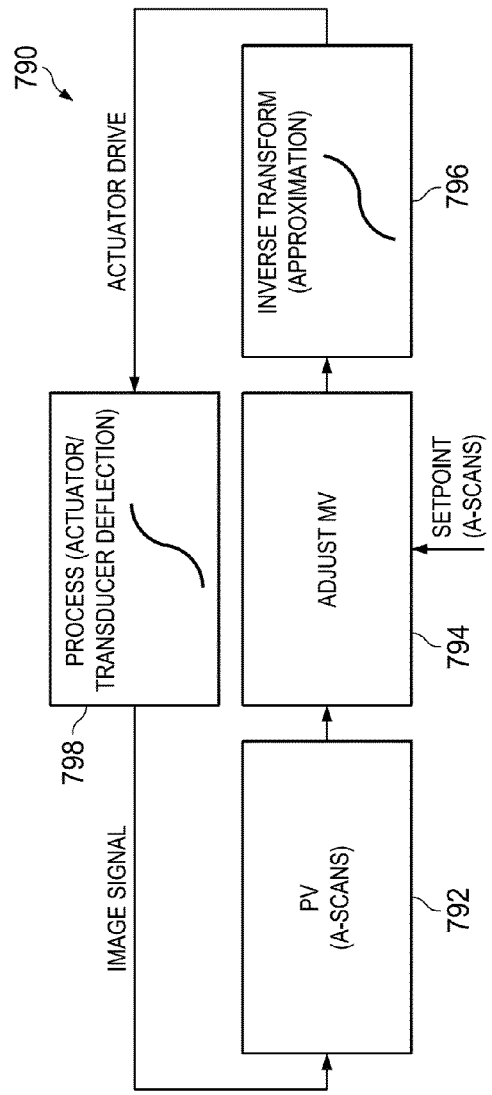
Fig. 45
Fig. 46

DEVICES, SYSTEMS, AND METHODS FOR CONTROLLING FIELD OF VIEW IN IMAGING SYSTEMS

CROSS-REFERENCE TO RELATED APPLICATIONS

The present application is a continuation of U.S. patent application Ser. No. 13/665,470, filed Oct. 31, 2012, which claims priority to and the benefit of each of U.S. Provisional Patent Application Nos. 61/553,772 and 61/553,789, filed Oct. 31, 2011, each of which is hereby incorporated by reference in its entirety.

TECHNICAL FIELD

Embodiments of the present disclosure relate generally to imaging systems and, more particularly, to imaging systems sized for use within human vasculature. In some instances, the devices, systems, and methods of the present disclosure are directed to controlling the field of view of such imaging systems.

BACKGROUND

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death.

The medical profession relies upon a wide variety of tools to treat heart disease, ranging from drugs to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow. Such techniques have traditionally relied on CT scans performed before surgery and angiograms during surgery to identify important anatomical features of the vasculature associated with the interventions. However, the information from a CT scan is often inaccurate at the time of surgery since the aneurysm is continually evolving over time.

Further, interventional procedures in the intracardiac space are continually developing. In that regard, structural heart procedures, including but not limited to valve replacement, valve repair, catheter ablation for arrhythmia, left atrial appendage (LAA) procedures, patent foramen ovale (PFO) procedures, and atrial septal defect procedures, also rely on imaging of the corresponding heart structures. Without accurate and detailed images of the associated structures, these interventional procedures in the intracardiac space become difficult, if not impossible, to perform successfully.

In recent years, techniques have been developed for obtaining detailed information about coronary and peripheral vessels as well as the intracardiac structures. For example, Intravascular Ultrasound (IVUS) and Intracardiac Echocardiography (ICE) techniques employ one or more very small transducers arranged towards the end of a catheter to provide electronically transduced echo signals to an external imaging system in order to produce a two or three-dimensional image of the lumen, the vessel tissue, and/or the tissue surrounding the vessel. Often these high quality images are generated in substantially real time. The images from these techniques allow a user to view the form and structure of a site rather then merely determining that blood is flowing.

In some instances, these devices rely on mechanical movement of an imaging transducer (e.g., an ultrasound transducer) in order to repeatedly sample a multi-dimensional space. In order to provide accurate information, effort is made to coordinate the transducer motion and the associated ultrasound acquisition. In that regard, the external imaging system often controls the movement of the transducer. For example, in some instances the displacement of the imaging transducer is directly correlated to the voltage or current waveform of a control signal generated by the external imaging system.

While the existing devices and methods have been generally adequate for their intended purposes, they have not been entirely satisfactory in all respects. The devices, systems, and associated methods of the present disclosure overcome one or more of the shortcomings of the prior art.

SUMMARY

Devices, systems, and methods for controlling the field of view in imaging systems are provided.

In one embodiment an imaging device is provided. The imaging device includes a flexible elongate member having a proximal portion and a distal portion. The flexible elongate member is sized and shaped for use within an internal structure of a patient. An imaging transducer is positioned within the distal portion of the flexible elongate member. The imaging transducer is movable along a motion profile. A marker is positioned adjacent to the imaging transducer such that the marker is identifiable in image data obtained by the imaging transducer when the imaging transducer reaches a predetermined position along the motion profile. In some instances, the predetermined position is a start boundary or an end boundary of the motion profile. In some embodiments, the motion profile has a desired field of view of between about 30 degrees and about 400 degrees, such as 120 degrees, 360 degrees, or otherwise. In some embodiments, the marker is integrally formed with a housing of the flexible elongate member. In some embodiments, the marker is secured to the distal portion of the flexible elongate member and is formed of a material having an increased acoustic reflectivity relative to other sections of the distal portion of the flexible elongate member. In some instances, the marker has a simple geometrical profile. The flexible elongate member has a diameter equal to or less than 4 mm, 1 mm, and/or 0.3 mm in some implementations.

In some implementations, the marker includes an inner surface for reflecting energy emitted from the imaging transducer. In that regard, the inner surface may be planar and/or curved. In some instances, the inner surface extends parallel to a longitudinal axis of the flexible elongate member. In some instances, the inner surface extends at an oblique angle with respect to a longitudinal axis of the flexible elongate member. In some embodiments, the oblique angle is between about 1 degrees and about 89 degrees such that a distal portion of the inner surface is positioned closer to the longitudinal axis than a proximal portion of the inner surface. In some implementations, a distal end of the inner surface is positioned in alignment with an axis of rotation of the imaging transducer along a longitudinal axis of the imaging element. In other implementations, a distal end of the inner surface is positioned distally beyond an axis of rotation of the imaging transducer along a longitudinal axis of the imaging element. In that regard, the distal end of the inner surface is positioned between about 0.001" and about 0.100" distal of the axis of rotation of the imaging transducer in some instances. Further, in some instances the distal end of the inner surface is positioned at an angle between about 0 degrees and about 75 degrees distally relative to the axis of rotation of the imaging transducer.

In some embodiments, an imaging system is provided. The imaging system includes an imaging device according to the present disclosure. In that regard, the imaging device may include a flexible elongate member having a proximal portion and a distal portion. The flexible elongate member is sized and shaped for use within an internal structure of a patient. An imaging transducer is positioned within the distal portion of the flexible elongate member. The imaging transducer is movable along a motion profile. A marker is positioned adjacent to the imaging transducer such that the marker is identifiable in image data obtained by the imaging transducer when the imaging transducer reaches a predetermined position along the motion profile. In some instances, the predetermined position is a start boundary or an end boundary of the motion profile. In some embodiments, the motion profile has a desired field of view of between about 30 degrees and about 400 degrees, such as 120 degrees, 360 degrees, or otherwise. In some embodiments, the marker is integrally formed with a housing of the flexible elongate member. The flexible elongate member has a diameter equal to or less than 4 mm, 1 mm, and/or 0.3 mm in some implementations.

The imaging system also includes a controller in communication with the imaging device. The controller is configured to adjust a control signal being provided to an actuator moving the imaging transducer along the motion profile based on identifying the marker within the image data in order to achieve a desired field of view for the imaging transducer as well as the start and end positions of the field of view.

Additional aspects, features, and advantages of the present disclosure will become apparent from the following detailed description.

BRIEF DESCRIPTION OF THE DRAWINGS

FIG. 23 is a graph showing the tracking of the markers of FIGS. 21a-21k and FIGS. 22a-22k according to an embodiment of the present disclosure incorporating a thresholding algorithm.

FIG. 24 is a graph showing the tracking of the markers of FIGS. 21a-21k and FIGS. 22a-22k according to another embodiment of the present disclosure incorporating a running average algorithm.

FIG. 25 is a flow chart illustrating a method of controlling a control signal of an imaging system according to an embodiment of the present disclosure incorporating a correlation algorithm.

FIG. 26 is an image showing identification of a region associated with a visual marker suitable for creating a template for use in a correlation algorithm according to an embodiment of the present disclosure.

FIG. 27a is a heat map showing a cross-correlation between a template of a correlation algorithm and a current imaging frame according to an embodiment of the present disclosure.

FIG. 27b is a close-up of a portion of the heat map of FIG. 27a containing an area of maximum correlation.

FIG. 28 is a flow chart illustrating a method of controlling a control signal of an imaging system according to an embodiment of the present disclosure incorporating a reverse correlation algorithm.

FIG. 29 is an image showing identification of a constant signal region and a imaging marker region that are suitable for creating a template for use in a reverse correlation algorithm according to an embodiment of the present disclosure.

FIG. 30a is a heat map showing the variance in cross-correlation values between the constant signal region and the imaging marker region of FIG. 29 according to an embodiment of the present disclosure.

FIG. 30b is a line graph of the cross-correlation values of the heat map of FIG. 30a at a particular image depth.

FIG. 31 is a heat map showing a cross-correlation between a template of a reverse correlation algorithm and a plurality of A-scans according to an embodiment of the present disclosure.

FIG. 35 is a line graph of the sum-of-gradient across a plurality of frames according to an embodiment of the present disclosure.

FIG. 36 includes a first (upper) heat map illustrating detection of a imaging marker across a plurality of A-scans before clamping and a second (lower) heat map illustrating detection of the imaging marker across the plurality of A-scans after clamping according to an embodiment of the present disclosure.

FIG. 42 is a diagrammatic schematic view of a hardware architecture suitable for implementing a sum-of-gradient portion of an algorithm according to an embodiment of the present disclosure.

FIG. 43 is a diagrammatic schematic view of a hardware architecture suitable for implementing a sum-of-differences portion of an algorithm according to an embodiment of the present disclosure.

FIG. 45 is a diagrammatic schematic view of a hardware architecture suitable for determining a location of a visual marker based on a median value according to an embodiment of the present disclosure.

FIG. 46 is a diagrammatic schematic view of a hardware architecture suitable for acting as a control loop for a sum-of-differences and sum-of-gradient algorithm according to an embodiment of the present disclosure.

DETAILED DESCRIPTION

Figure 1:
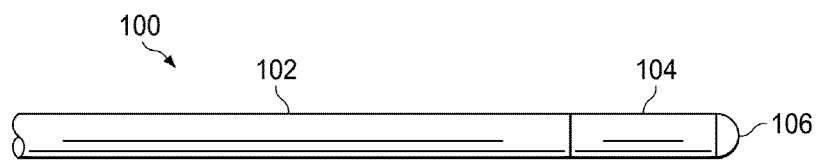
FIG. 1 is a diagrammatic schematic view of a portion of an elongated member of an imaging system according to one aspect of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figures 2, 7:
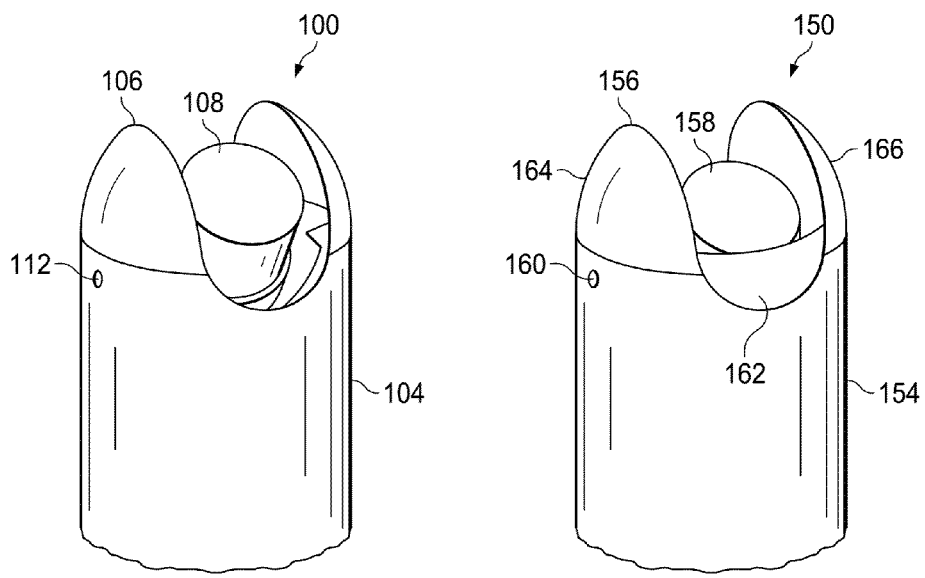
FIG. 2 is a diagrammatic perspective view of a distal end portion of the elongated member of FIG. 1 according to an embodiment of the present disclosure.
FIG. 7 is a diagrammatic perspective view of a distal end portion of an elongated member that includes an imaging marker according to an embodiment of the present disclosure.
Figure 3:
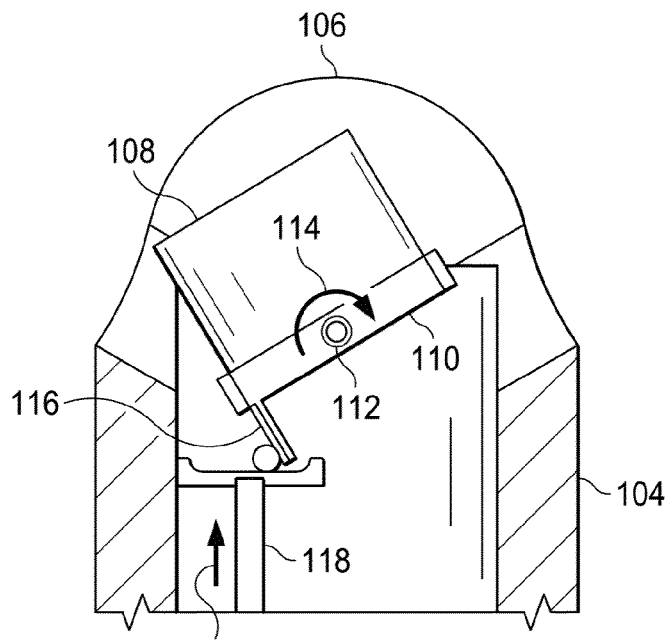
FIG. 3 is a partial cross-sectional side view of a distal end portion of the elongated member of FIGS. 1 and 2 illustrating a transducer element of the imaging system in a first orientation.
Figure 4:
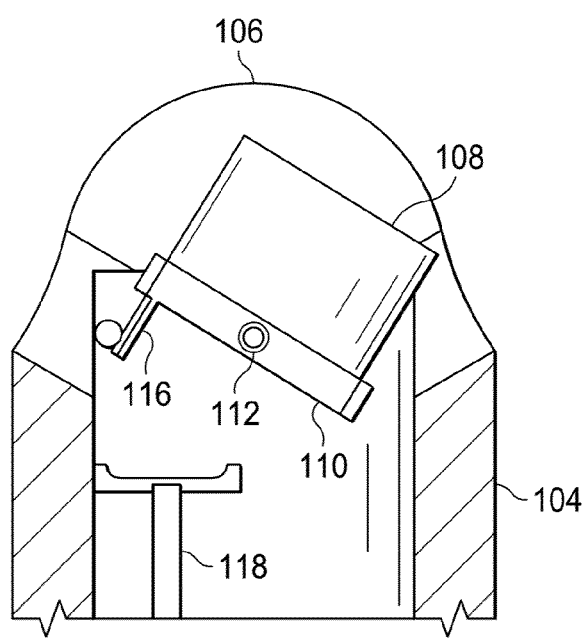
FIG. 4 is a partial cross-sectional side view of the distal end portion of the elongated member similar to that of FIG. 3 but illustrating the transducer element in a second orientation.

Referring to FIGS. 1-4, shown therein are aspects of an elongated member 100 of an imaging system according to an embodiment of the present disclosure. More specifically, FIG. 1 is a diagrammatic schematic view of a portion of the elongated member 100; FIG. 2 is a diagrammatic perspective view of a distal end portion of the elongated member 100; FIG. 3 is a partial cross-sectional side view of a distal end portion of the elongated member 100, illustrating a transducer element of the imaging system in a first orientation; FIG. 4 is a partial cross-sectional side view of the distal end portion of the elongated member 100, similar to that of FIG. 3, but illustrating the transducer element in a second orientation.

As shown in FIG. 1, the elongated member 100 includes a flexible body 102 having a distal housing portion 104 extending to a distal tip 106. As shown in FIGS. 2-4, a transducer 108 is disposed within the distal housing portion 104 adjacent the distal tip 106. In some instances the transducer 108 is an ultrasound transducer. In the illustrated embodiment, the transducer 108 is mounted on a platform 110 that is configured to rotate about an axis defined by a pivot pin 112 extending through a portion of the platform 110. In that regard, transducer 108 rotates—in the direction of arrow 114—from an initial orientation (shown in FIG. 3) to a fully-rotated orientation (shown in FIG. 4). From the fully-rotated orientation, the transducer rotates—in the direction opposite of arrow 114—back to the initial orientation. This process is repeated to cause oscillation of the transducer 108.

In the illustrated embodiment, an interface arm 116 extends proximally from the platform 110 and interfaces with an actuator 118 to facilitate oscillation of the transducer 108. In that regard, in some instances the actuator 118 is a shape-memory actuator as described in U.S. Pat. No. 7,658,715, titled "MINIATURE ACTUATOR MECHANISM FOR INTRAVASCULAR IMAGING," or U.S. Provisional Patent Application No. 61/546,419, filed on Oct. 12, 2011, each hereby incorporated by reference in its entirety. In other instances, the actuator 118 is driven by a drive shaft or other physical connection to a motor or other driving device positioned adjacent a proximal portion of the elongated member. In yet other instances, the actuator is driven by hydraulics, air pressure, and/or other means of transmitting mechanical energy into motion. As a general matter, the actuator 118 can be any type of device suitable for imparting sweeping, oscillatory, and/or rotational movement to the transducer 108. As shown in FIG. 3, when the transducer 108 is in the initial position advancement of the actuator 118 distally, as indicated by arrow 120, urges the interface arm 116 distally, which causes the platform 110 to rotate about the pivot pin 112. Rotation of the platform 110 sweeps the transducer 108 from the initial position (FIG. 3) to the fully-rotated position (FIG. 4).

Figure 5:
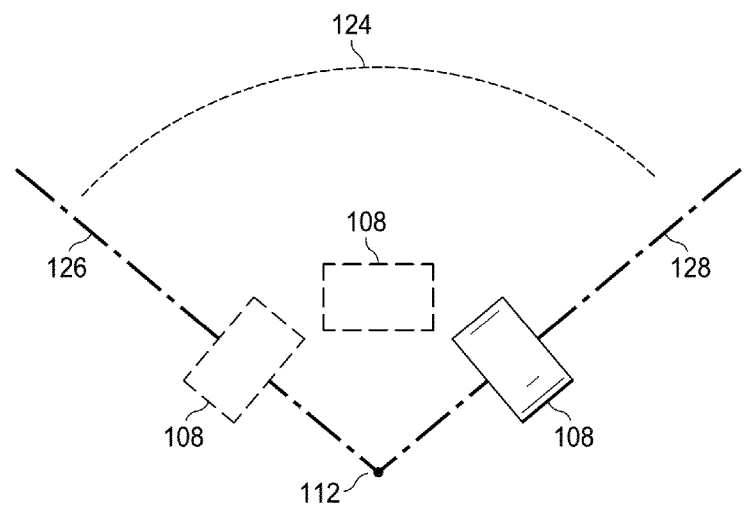
FIG. 5 is a diagrammatic schematic view of a motion path of a transducer element of an imaging system according to one aspect of the present disclosure.

In that regard, FIG. 5 illustrates an exemplary motion profile of the transducer 108. As shown, the transducer 108 pivots about the pivot pin 112 and travels across an angle 124 between a starting orientation (represented by axis 126 and the transducer 108 shown in phantom on the far left of the drawing) and an ending orientation (represented by axis 128 and the transducer 108 shown on the far right of the drawing). The angle 124 that the transducer 108 travels between the starting orientation and the ending orientation is generally between about 1 degree and about 400 degrees, depending on the imaging application. In some instances, the angle 124 is between about 25 degrees and about 360 degrees. In some particular instances, the angle 124 is approximately 120 degrees. It is understood, however, that the present disclosure is applicable to any amount of transducer rotation and no limitation is intended by these exemplary ranges.

Figure 6:
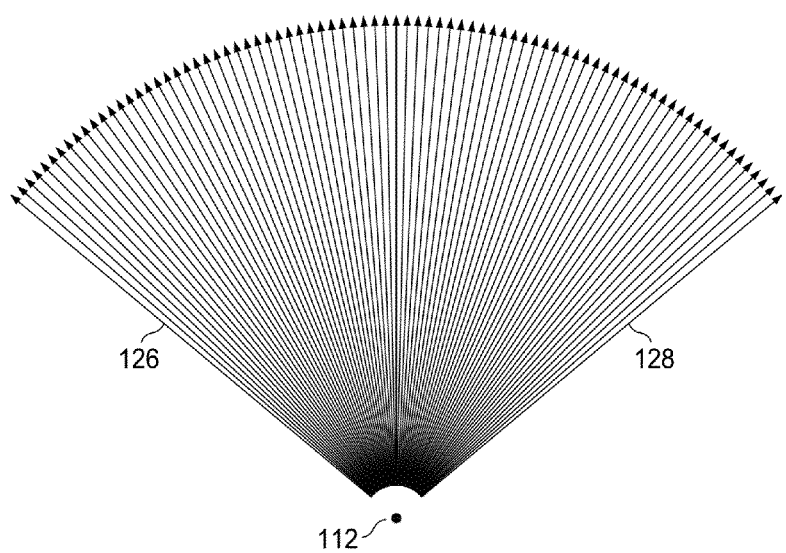
FIG. 6 is a diagrammatic schematic view of the imaging scans associated with the motion path of FIG. 5 according to one aspect of the present disclosure.

Referring now to FIG. 6, shown therein is a diagrammatic schematic representation of the imaging scans associated with the motion path of imaging transducer 108 shown in FIG. 5. In that regard, in order to better understand the techniques of the present disclosure, it is necessary to first understand the image format nomenclature that will be used herein to describe various embodiments of the present disclosure. In that regard, typically as the ultrasound transducer or optical element traverses through its motion profile, it collects data on a line-by-line basis as the transducer is repeatedly transitioned between send and receive modes. Each line is generally referred to as an "A-Scan" and it contains data sampled at defined depths. Once the transducer has travelled the entire field-of-view, the set of A-Scans are collected and grouped together as a "B-Scan" or "frame." Accordingly, a "B-Scan" or "frame" is most commonly understood to be the set of "A-Scans" or lines associated with the transducer or other imaging element traveling once along its motion profile. In that regard, each of the lines in FIG. 6 is representative of an "A-scan," whereas the entire collection of lines in FIG. 6 is representative of a "B-scan." It should be noted, however, that in some embodiments of the present disclosure, for various reasons, one or more A-scans are omitted from the collection of A-scans that are grouped together to form a B-scan.

While the transducer 108 has been described as under going oscillatory motion, in other instances the transducer 108 is maintained in a fixed position and a mirror or other reflective element is oscillated. In that regard, the mirror or other reflective element reflects the signals generated by the fixed transducer (e.g., acoustic waves associated with ultrasound imaging) such that the signals are swept through the motion profile in a manner similar to when the transducer itself is oscillated. In some instances, the fixed transducer and reflector are configured in a manner similar to the embodiments described U.S. Pat. No. 7,658,715, titled "MINIATURE ACTUATOR MECHANISM FOR INTRAVASCULAR IMAGING," which is hereby incorporated by reference in its entirety.

In general, the elongate member 100 is sized and shaped for use within an internal structure of a patient, including but not limited to a patient's arteries, veins, heart chambers, neurovascular structures, GI track, bronchials, organs, and/or other areas where internal imaging of patient anatomy is desirable. In that regard, depending on the particular medical application, the elongate member 100 is configured for use in cardiology procedures, neurovascular procedures, pulmonology procedures, endoscopy procedures, colonoscopy procedures, natural orifice procedures (such as Natural Orifice Translumenal Endoscopic Surgery (NOTES)), and/or other medical procedures.

Accordingly, in some embodiments the elongate member 100 takes the form of a guidewire or catheter. In some instances, the imaging system as a whole, the elongate member 100, the actuator 118, and/or other aspects of the imaging system are similar to those described in U.S. Pat. No. 5,379, 772, titled "FLEXIBLE ELONGATE DEVICE HAVING FORWARD LOOKING ULTRASONIC IMAGING," U.S. Pat. No. 7,115,092, titled "TUBULAR COMPLIANT MECHANISMS FOR ULTRASONIC IMAGING SYSTEMS AND INTRAVASCULAR INTERVENTIONAL DEVICES," and/or U.S. Pat. No. 7,658,715, titled "MINIATURE ACTUATOR MECHANISM FOR INTRAVASCULAR IMAGING," each of which is hereby incorporated by reference in its entirety.

To function most effectively, the data acquired with the transducer 108 must be coordinated with the transducer's motion. Accordingly, in some aspects, the present disclosure is directed to control mechanisms that monitor and control the motion of the transducer and, thereby, control the resulting field of view of the imaging system. In that regard, aspects of the present disclosure increase the accuracy and reproducibility of the transducer's motion. This results in improved clarity and accuracy in the resulting images provided by the imaging systems. In that regard, some embodiments of the field-of-view control techniques of the present disclosure are suitable for use in the context of one or more acoustic or imaging markers or targets. Further, in some particular instances, imaging devices of the present disclosure include one or more acoustic or other imaging-modality markers that are utilized by the field-of-view control techniques of the present disclosure. A few exemplary embodiments of imaging devices having such markers are described below, but no limitation is intended thereby. Rather, it is understood that the field-of-view control techniques of the present disclosure are suitable for use with virtually any type of marker, including markers of various shapes, sizes, and materials, markers positioned in, on, adjacent to, and spaced from an imaging device, and/or markers otherwise identifiable by an imaging system.

As noted, in some embodiments a marker is utilized to monitor the position of the transducer 108 during its motion profile. In that regard, the marker facilitates detection of when/if the transducer 108 reaches a certain point along its motion profile. For example, in some instances the marker is configured such that it is detected when the transducer 108 reaches the ending orientation, as represented by axis 128. In other instances, the marker is configured to be detected if and/or when the transducer 108 reaches other points along its motion profile, including but not limited to the starting orientation, a mid-point orientation (represented by transducer 108 shown in phantom in the middle of the drawing of FIG. 5), and/or other orientations along the motion profile. In that regard, the boundaries of the motion profile of the transducer 108 are illustrated in FIG. 5 by axes 126 and 128. These boundaries are representative of the desired motion profile of the transducer during use. However, it is understood that the actual motion profile of the transducer may vary during use and, therefore, may travel beyond the boundaries of the desired motion profile. Accordingly, in some instances, the marker is configured to be detected if and/or when the transducer 108 reaches a point beyond the desired motion profile. Further, in some embodiments, markers are utilized to detect if and/or when the transducer 108 reaches two or more points along the motion profile, rather than a single point. In that regard, in some instances the two or more points are spaced apart by a fixed distance and/or angle from one another.

Exemplary embodiments of configurations of imaging devices having markers suitable for use with the techniques of the present disclosure will now be described in the context of FIGS. 7-16. For the sake of clarity and simplicity, the discussion herein will use the ending orientation of the transducer (represented by axis 128 and the transducer 108 shown on the far right of FIG. 5) as the location of the described markers. However, no limitation is intended thereby. Rather, it is explicitly understood that the one or more of the described markers and/or other types of markers may be positioned for detection at one or more points along the motion profile of the transducer as discussed above.

Referring to FIGS. 7-16, shown therein are several exemplary embodiments of imaging devices incorporating markers that are suitable for use with the field-of-view control techniques of the present disclosure. In that regard, referring more specifically to FIG. 7, shown therein is a distal portion of an elongated member 150 according to an embodiment of the present disclosure. The distal portion of the elongated member 150 includes a housing 154 extending to a distal tip 156. Further, an ultrasound transducer 158 is positioned within the distal portion of the elongated member 150 and pivots about a pivot pin 160. The elongated member 150 also includes an acoustic target 162 positioned between arms 164 and 166. In the illustrated embodiment, the acoustic target 162 is positioned such that when the ultrasound transducer 158 reaches the ending orientation of its motion profile the acoustic target 162 is within the visible field of the ultrasound transducer 158. In that regard, when the acoustic target 162 is within the visible field or frame of the ultrasound transducer 158 the acoustic target 162 is identifiable as an acoustic signal. The acoustic target 162 is formed from a material having a high (or low) acoustic reflectivity relative to its environment during use. In some instances, the acoustic target 162 has an easily recognizable shape, such as a simple geometrical profile. Accordingly, a processing system receiving data from the ultrasound transducer 158 can determine whether the acoustic target 162 is present in any particular image or set of images. Various techniques for making this determination are discussed below in detail. In this manner, the system can recognize when the ultrasound transducer 158 reaches the full field of view.

Further, while the acoustic target 162 has been described in the context of an ultrasound transducer 158, it is understood that a similar concept may be employed with an optical or optoelectronic sensor. In that regard, instead of an acoustic target, a visual target that is identifiable by the optical sensor may be utilized. Further still, in some instances a plurality of acoustic targets 162 are utilized at discrete points along the motion profile of the transducer, including but not limited to the starting orientation, the mid-point orientation, the ending orientation, and/or points in between. These variations are likewise applicable to the other embodiments described herein.

Figure 8:
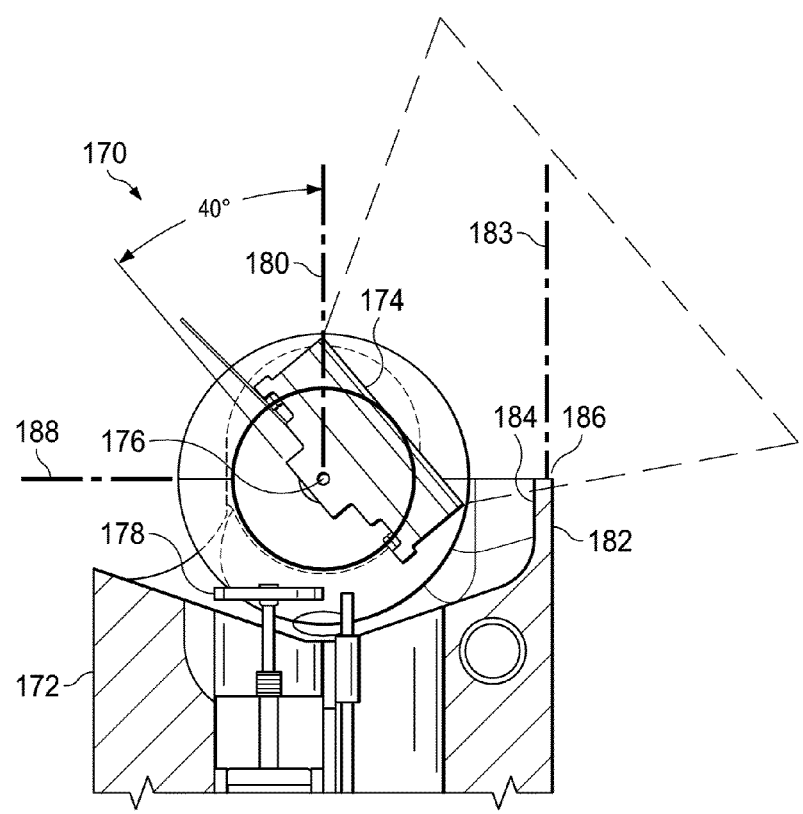
FIG. 8 is a diagrammatic cross-sectional side view of a distal end portion of an elongated member having an imaging marker according to an embodiment of the present disclosure, where a transducer of the elongate member is in a first orientation relative to the imaging marker.
Figure 9:
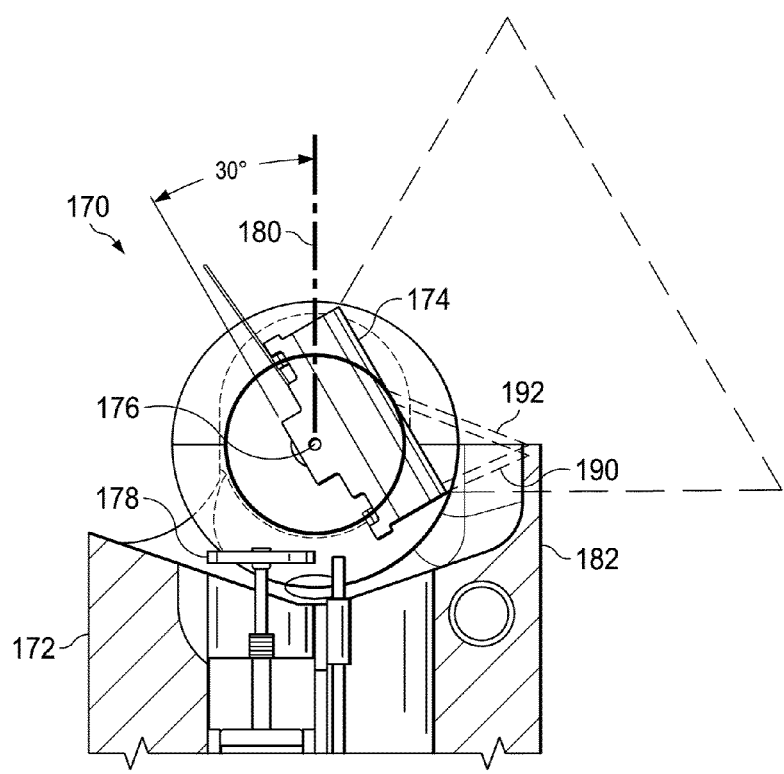
FIG. 9 is a diagrammatic cross-sectional side view of the distal end portion of the elongated member of FIG. 8, but where the transducer of the elongate member is in a second orientation relative to the imaging marker.
Figure 10:
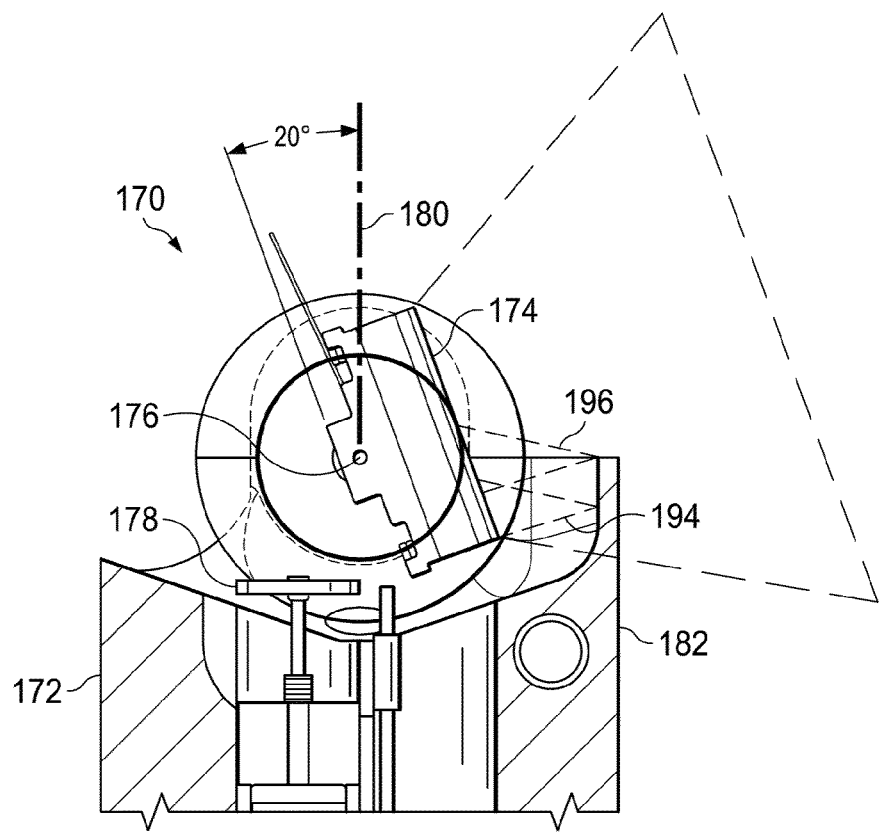
FIG. 10 is a diagrammatic cross-sectional side view of the distal end portion of the elongated member of FIG. 8, but where the transducer of the elongate member is in a third orientation relative to the imaging marker.

Referring now to FIGS. 8-10, shown therein are aspects of an imaging device 170 according to an embodiment of the present disclosure. Referring initially to FIG. 8, a diagrammatic cross-sectional side view of a distal portion 172 of the imaging device 170 is shown. In that regard, the imaging device 170 includes an imaging element 174 that rotates about a pivot axis 176 in response to actuator 178. The imaging element 174 may be any type of imaging element (e.g., ultrasound transducer, optical emitter/receiver, reflector, and/or otherwise), but for the sake of clarity will be described as an ultrasound transducer. In the illustrated embodiment, the imaging element 174 pivots about the pivot axis 176 through a motion profile having an angle between about 100 degrees and about 160 degrees in some instances. In other embodiments, the imaging element 174 pivots about the pivot axis through a motion profile having an angle less than about 100 degrees or more than about 160 degrees.

Generally, for a particular imaging device or a specific application of that imaging device there is a particular motion profile angle that is desirable. It is understood that this value varies greatly between devices and even application of a single device. For example, as noted above the desired motion profile angle may be between about 1 degree and about 400 degrees. For the sake of clarity in understanding the concepts related to marker discussed with respect to the embodiment of FIGS. 8-10 (and the embodiments of FIGS. 11-16 discussed below), a desired motion profile angle of 120 degrees will be assumed. More specifically, referring to FIG. 8, the desired motion profile will be assumed to be from 60 degrees to either side of the longitudinal axis 180 of the imaging device 170. That is, the desired motion profile will have a desired starting orientation where the transducer 174 is positioned at a 60 degree angle to the left of the longitudinal axis 180 as viewed in FIG. 8 and a desired ending orientation where the transducer 174 is positioned at a 60 degree angle to the right of the longitudinal axis as viewed in FIG. 8. For reference, the orientation of the transducer 174 illustrated in FIG. 8 is a 50 degree angle to the right of the longitudinal axis 180. However, no limitation is intended by this presumed motion profile as the concepts of the present disclosure are equally applicable to other motion profile angles, including smaller angles, larger angles, varying angles, angle ranges, and/or other variations of the motion profile.

As shown in FIG. 8, the imaging device 170 includes a marker or target 182. In some instances, the marker 182 is positioned between arms of the imaging device similar to acoustic target 162 of elongated member 150 discussed above. In the illustrated embodiment, the marker 182 is positioned such that when the ultrasound transducer 174 reaches the ending orientation of its motion profile the marker 182 is within the visible field of the transducer 174. In that regard, with the marker within the visible field or frame of the transducer 174, the marker 182 can be identified within the imaging data obtained from the transducer. Accordingly, a processing system receiving data from the transducer 174 can determine whether the marker 182 is present in any particular image or set of images and/or the location of the marker within such an image or set of images.

In the embodiment of FIG. 8, the marker 182 is a wall or portion of a wall defined by the distal portion 172 of the imaging device. The marker 182 extends along axis 183 that is parallel to the longitudinal axis 180 in the illustrated embodiment. In some instances, an inner wall 184 defined by the marker 182 is planar. In other instances, the inner wall 184 is at least partially concave. In yet other instances, the inner wall 184 is at least partially convex. In some instances, the inner wall 184 is a combination of two or more of planar, concave, and/or convex surfaces. In that regard, the inner wall 184 is sized and shaped to reflect energy emitted from the transducer 174 when the transducer reaches one or more points along the motion profile of the transducer. For example, in the embodiment of FIG. 8, the marker 182 is configured to reflect energy emitted from the transducer 174 when the transducer reaches the ending orientation (i.e., 60 degrees offset to the right of the longitudinal axis 180 as viewed in FIG. 8). To that end, in the illustrated embodiment a distal most portion or distal tip 186 of the marker 182 ends at position that is in alignment with the axis of rotation 176. In that regard, the distal tip 186 of the marker 182 ends at an axis 188 extending perpendicular to the longitudinal axis 180 and through the pivot axis 176, as shown. However, in other embodiments the distal tip 186 of the marker 182 ends at positions proximal to the pivot axis 176 (downward as viewed in FIG. 8) and positions distal to the pivot axis 176 (upward as viewed in FIG. 8). The positioning of the distal tip 186 of the marker 182 along the longitudinal axis 180 relative to the pivot axis 176 is selected based on the desired field-of-view angle in some instances.

In some instances, the marker 182 is integrally formed with the remaining portions of the housing or distal portion 172. For example, in some instances the distal portion 172 is machined from a single piece of material to include the marker 182. In other instances, the marker 182 is fixedly secured to the distal portion 172 via welding, adhesive, bonding, mechanical connection, and/or combinations thereof. In that regard, the marker 182 is formed of the same material as other portions of the housing or distal portion 172 in some embodiments. However, in other embodiments the marker 182 is formed of a material different than the remaining portions of the housing or distal portion 172. Examples of suitable materials for the marker 182 and/or the distal portion 172 include without limitation, biocompatible metals (e.g., stainless steel, cobalt chrome, etc.), ceramics, and polymers.

As noted above, in the embodiment of FIGS. 8-10, the marker 182 is configured to reflect energy emitted from the transducer 174 when the transducer reaches the ending orientation of the transducer motion profile (i.e., 60 degrees offset to the right of the longitudinal axis 180 as viewed in FIG. 8). In that regard, referring to FIG. 8, when the transducer 174 is at a 50 degree angle to the right of the longitudinal axis 180, 10 degrees short of the ending orientation, none (or a negligible amount) of the energy emitted by the transducer is reflected by the marker 182 and back onto the transducer. However, referring to FIG. 9, when the transducer 174 is at a 60 degree angle to the right of the longitudinal axis 180 (i.e., at the ending orientation) a portion 190 of the energy emitted by the transducer contacts the marker 182 and reflects a signal 192 back onto the transducer. Referring now to FIG. 10, when the transducer 174 is at a 70 degree angle to the right of the longitudinal axis 180 (i.e., 10 degrees beyond the ending orientation) a portion 194 of the energy emitted by the transducer contacts the marker 182 and reflects a signal 196 back onto the transducer. As shown, both the emitted portion 194 of the signal sent from the transducer that contacts the marker and the reflected signal 196 that is received by the transducer from the marker in the over-driven position of FIG. 10 are increased relative to the emitted portion 190 and reflected signal 192 associated with the ending orientation of FIG. 9. In some instances, as the signal strength increases the ability to identify the marker in the resulting image data becomes easier. Further, in some embodiments the relative strength and/or area of the reflected signal can be utilized to determine an orientation of the transducer.

Figure 11:
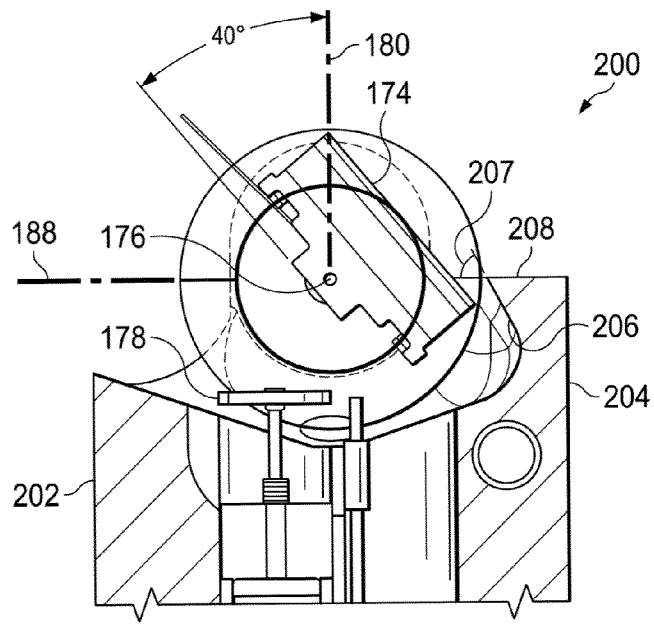
FIG. 11 is a diagrammatic cross-sectional side view of a distal end portion of an elongated member having an imaging marker according to another embodiment of the present disclosure, where a transducer of the elongate member is in a first orientation relative to the imaging marker.
Figure 12:
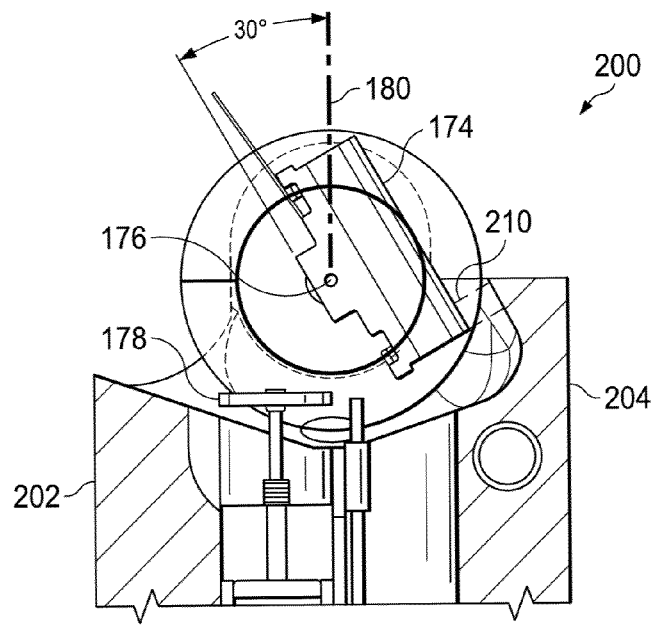
FIG. 12 is a diagrammatic cross-sectional side view of the distal end portion of the elongated member of FIG. 11, but where the transducer of the elongate member is in a second orientation relative to the imaging marker.
Figure 13:
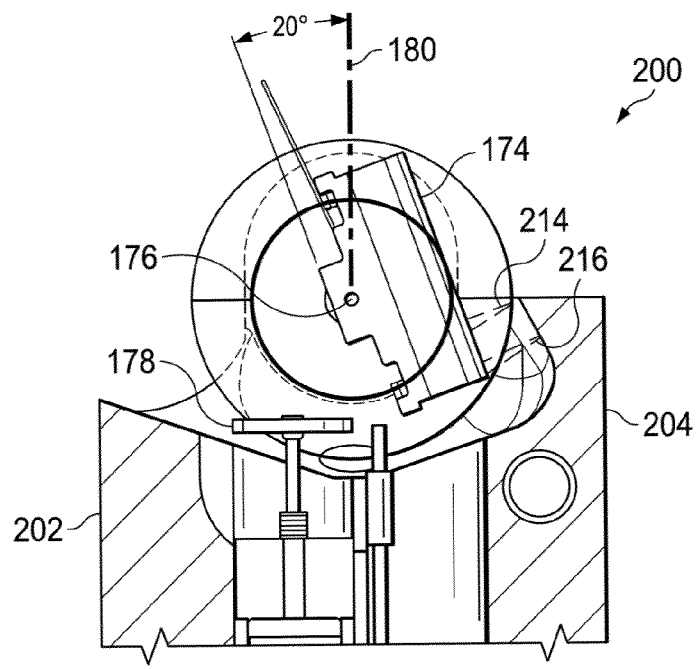
FIG. 13 is a diagrammatic cross-sectional side view of the distal end portion of the elongated member of FIG. 11, but where the transducer of the elongate member is in a third orientation relative to the imaging marker.

Referring now to FIGS. 11-13, shown therein are aspects of an imaging device 200 according to an embodiment of the present disclosure. Referring initially to FIG. 11, a diagrammatic cross-sectional side view of a distal portion 202 of the imaging device 200 is shown. In that regard, the imaging device 200 includes some elements similar to those discussed above with respect to imaging device 170 and, therefore, the same reference numerals are utilized in the context of imaging device 200. For example, the imaging device 200 includes an imaging element 174 that rotates about a pivot axis 176 in response to actuator 178. The imaging element 174 may be any type of imaging element (e.g., ultrasound transducer, optical emitter/receiver, reflector, and/or otherwise), but for the sake of clarity will be described as an ultrasound transducer.

As shown in FIG. 11, the imaging device 200 includes a marker or target 204. In some instances, the marker 204 is positioned between arms of the imaging device similar to acoustic target 162 of elongated member 150 discussed above. In the illustrated embodiment, the marker 204 is positioned such that when the ultrasound transducer 174 reaches the ending orientation of its motion profile the marker 204 is within the visible field of the transducer 174. In that regard, with the marker 204 within the visible field or frame of the transducer 174, the marker 204 can be identified within the imaging data obtained from the transducer. Accordingly, a processing system receiving data from the transducer 174 can determine whether the marker 204 is present in any particular image or set of images and/or the location of the marker within such an image or set of images.

In the embodiment of FIG. 11, the marker 204 is a wall or portion of a wall defined by the distal portion 202 of the imaging device 200. The marker 204 has an inner wall 206 that extends at an oblique angle with respect to the longitudinal axis 180 and the axis 188 of the imaging device 200. In that regard, in some embodiments the inner wall 206 extends at an angle 207 between about 1 degree and about 89 degrees relative to an axis extending perpendicular to the longitudinal axis 180 (e.g., axis 188), which corresponds to an angle between about 89 degrees and about 1 degree relative to the longitudinal axis 180. In some particular embodiments, the inner wall extends at an angle between about 50 degrees and about 80 degrees, which corresponds to an angle between about 40 degrees and about 10 degrees relative to the longitudinal axis 180. In some instances, the angle 207 is selected such that the inner wall extends substantially perpendicular to the primary axis of transmission of the imaging element (e.g., the ultrasound acoustic vector) when the desired field of view is reached. In the illustrated embodiment of FIG. 11, the inner wall 206 extends at approximately a 60 degree angle relative to the axis 188. In some instances, the inner wall 206 defined by the marker 204 is planar. In other instances, the inner wall 206 is at least partially concave. In yet other instances, the inner wall 206 is at least partially convex. In some instances, the inner wall 206 is a combination of two or more of planar, concave, and/or convex surfaces. A benefit of the angled marker 206 is that the marker 206 is more easily visible or identifiable compared to when the marker is not angled because of the increased signal reflection resulting from the reflection angle of the transducer signal.

The inner wall 206 is sized and shaped to reflect energy emitted from the transducer 174 when the transducer reaches one or more points along the motion profile of the transducer. For example, in the embodiment of FIG. 11, the marker 204 is configured to reflect energy emitted from the transducer 174 when the transducer reaches the ending orientation (i.e., 60 degrees offset to the right of the longitudinal axis 180 as viewed in FIG. 11). More specifically, the inner wall 206 is configured to extend substantially parallel to the outer surface of the transducer 174 when the transducer is in the ending orientation such that the inner wall 206 extends substantially perpendicular to a primary axis along which the transducer 174 will emit energy. Further, in the illustrated embodiment a distal most portion or distal tip 208 of the marker 204 ends at position that is in alignment with the axis of rotation 176 of the transducer 174. In that regard, the distal tip 208 of the marker 204 ends at an axis 188 extending perpendicular to the longitudinal axis 180 and through the pivot axis 176, as shown. However, in other embodiments the distal tip 208 of the marker 204 ends at positions proximal to the pivot axis 176 (downward as viewed in FIG. 11) and positions distal to the pivot axis 176 (upward as viewed in FIG. 11). The positioning of the distal tip 208 of the marker 204 along the longitudinal axis 180 relative to the pivot axis 176 is selected based on the desired field-of-view angle in some instances.

As noted above, in the embodiment of FIGS. 11-13, the marker 204 is configured to reflect energy emitted from the transducer 174 when the transducer reaches the ending orientation of the transducer motion profile (i.e., 60 degrees offset to the right of the longitudinal axis 180 as viewed in FIG. 11). In that regard, referring to FIG. 11, when the transducer 174 is at a 50 degree angle to the right of the longitudinal axis 180, 10 degrees short of the ending orientation, none (or a negligible amount) of the energy emitted by the transducer is reflected by the marker 204 and back onto the transducer. However, referring to FIG. 12, when the transducer 174 is at a 60 degree angle to the right of the longitudinal axis 180 (i.e., at the ending orientation) a portion 210 of the energy emitted by the transducer contacts the marker 204 and reflects a signal back onto the transducer. In that regard, the inner surface 206 of the marker 204 is substantially perpendicular to the outer surface of the transducer 174. Referring now to FIG. 13, when the transducer 174 is at a 70 degree angle to the right of the longitudinal axis 180 (i.e., 10 degrees beyond the ending orientation) a portion 214 of the energy emitted by the transducer contacts the marker 204 and reflects a signal 216 back onto the transducer.

Figure 14:
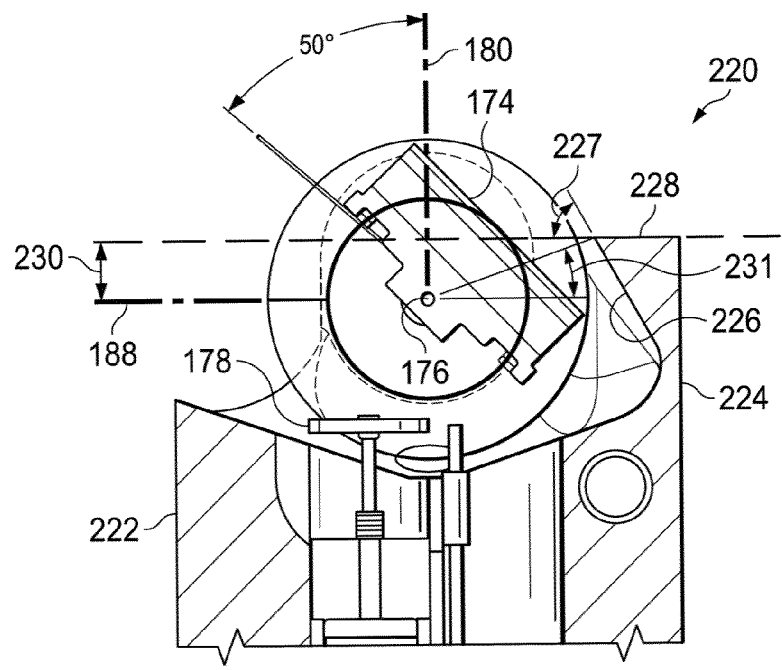
FIG. 14 is a diagrammatic cross-sectional side view of a distal end portion of an elongated member having an imaging marker according to another embodiment of the present disclosure, where a transducer of the elongate member is in a first orientation relative to the imaging marker.
Figure 15:
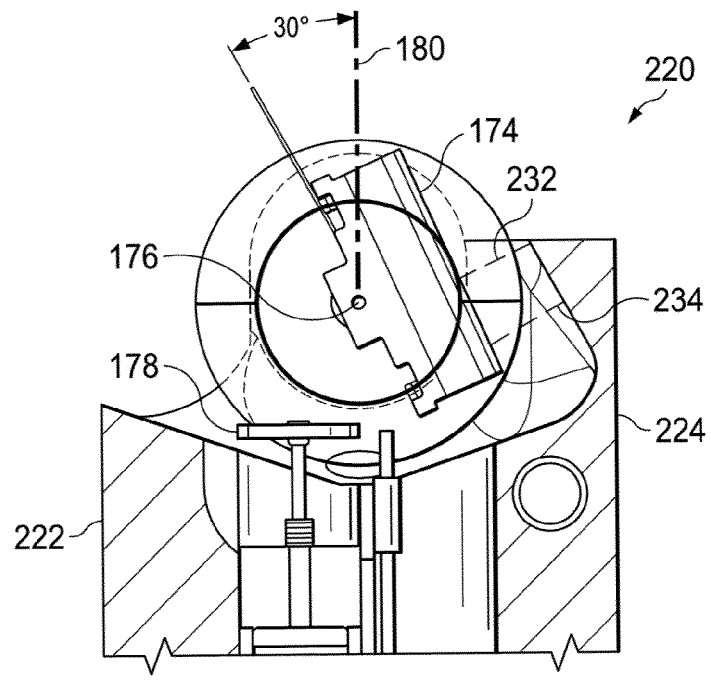
FIG. 15 is a diagrammatic cross-sectional side view of the distal end portion of the elongated member of FIG. 14, but where the transducer of the elongate member is in a second orientation relative to the imaging marker.
Figure 16:
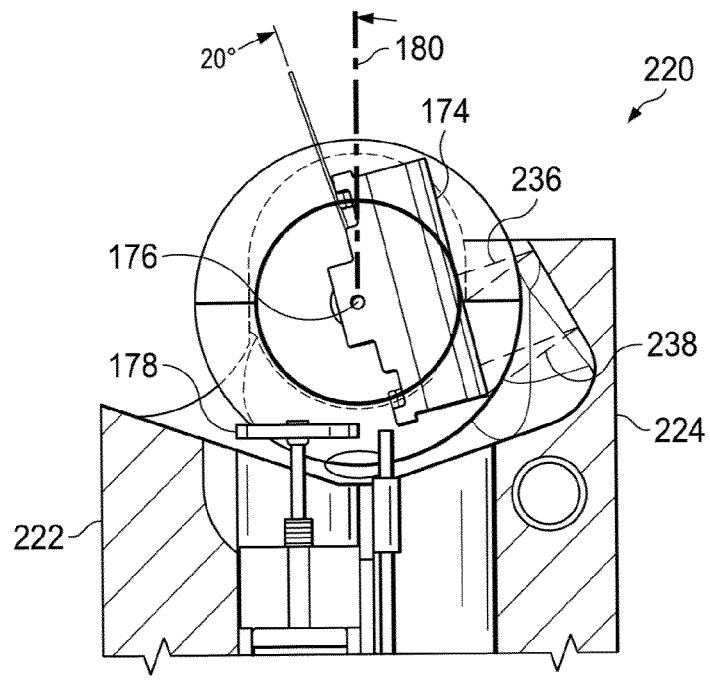
FIG. 16 is a diagrammatic cross-sectional side view of the distal end portion of the elongated member of FIG. 14, but where the transducer of the elongate member is in a third orientation relative to the imaging marker.

Referring now to FIGS. 14-16, shown therein are aspects of an imaging device 220 according to an embodiment of the present disclosure. Referring initially to FIG. 14, a diagrammatic cross-sectional side view of a distal portion 222 of the imaging device 220 is shown. In that regard, the imaging device 220 includes some elements similar to those discussed above with respect to imaging devices 170 and 200 and, therefore, the same reference numerals are utilized in the context of imaging device 220. For example, the imaging device 220 includes an imaging element 174 that rotates about a pivot axis 176 in response to actuator 178. The imaging element 174 may be any type of imaging element (e.g., ultrasound transducer, optical emitter/receiver, reflector, and/or otherwise), but for the sake of clarity will be described as an ultrasound transducer.

As shown in FIG. 14, the imaging device 220 includes a marker or target 224. In some instances, the marker 224 is positioned between arms of the imaging device similar to acoustic target 162 of elongated member 150 discussed above. In the illustrated embodiment, the marker 224 is positioned such that when the ultrasound transducer 174 reaches the ending orientation of its motion profile the marker 224 is within the visible field of the transducer 174. In that regard, with the marker 224 within the visible field or frame of the transducer 174, the marker 224 can be identified within the imaging data obtained from the transducer. Accordingly, a processing system receiving data from the transducer 174 can determine whether the marker 224 is present in any particular image or set of images and/or the location of the marker within such an image or set of images.

In the embodiment of FIG. 14, the marker 224 is a wall or portion of a wall defined by the distal portion 222 of the imaging device 220. The marker 224 has an inner wall 226 that extends at an oblique angle with respect to the longitudinal axis 180 and the axis 188 of the imaging device 200. In that regard, in some embodiments the inner wall 226 extends at an angle 227 between about 1 degree and about 89 degrees relative to an axis extending perpendicular to the longitudinal axis 180 (e.g., axis 188), which corresponds to an angle between about 89 degrees and about 1 degree relative to the longitudinal axis 180. In some particular embodiments, the inner wall extends at an angle between about 50 degrees and about 80 degrees, which corresponds to an angle between about 40 degrees and about 10 degrees relative to the longitudinal axis 180. In some instances, the angle 227 is selected such that the inner wall extends substantially perpendicular to the primary axis of transmission of the imaging element (e.g., the ultrasound acoustic vector) when the desired field of view is reached. In the illustrated embodiment of FIG. 14, the inner wall 226 extends at a 60 degree angle relative to the axis 188. In some instances, the inner wall 226 defined by the marker 224 is planar. In other instances, the inner wall 226 is at least partially concave. In yet other instances, the inner wall 226 is at least partially convex. In some instances, the inner wall 226 is a combination of two or more of planar, concave, and/or convex surfaces.

The inner wall 226 is sized and shaped to reflect energy emitted from the transducer 174 when the transducer reaches one or more points along the motion profile of the transducer. For example, in the embodiment of FIG. 14, the marker 224 is configured to reflect energy emitted from the transducer 174 when the transducer reaches the ending orientation (i.e., 60 degrees offset to the right of the longitudinal axis 180 as viewed in FIG. 14). More specifically, the inner wall 226 is configured to extend substantially parallel to the outer surface of the transducer 174 when the transducer is in the ending orientation such that the inner wall 226 extends substantially perpendicular to a primary axis along which the transducer 174 will emit energy. Further, in the illustrated embodiment a distal most portion or distal tip 228 of the marker 224 ends at a position that is distal of the axis of rotation 176 of the transducer 174. In that regard, the distal tip 228 of the marker 224 ends at distance 230 between about 0.001 inches and about 0.100 inches distal of an axis 188 extending perpendicular to the longitudinal axis 180 and through the pivot axis 176, as shown.

In some instances, the distal tip 228 of the marker 224 is positioned such that a distal boundary of the inner surface 226 (e.g., where the distal tip 228 and the inner surface 226 come together) is at a predetermined angle 231 with respect to the axis 188. For example, in the illustrated embodiment the distal tip 228 is positioned such that the distal boundary of the inner surface 226 is at approximately a 15 degree angle with respect to the axis 188 as measured from the point where the central longitudinal axis 180 intersects the axis 188. Generally, the angle as measured from the point where the central longitudinal axis 180 intersects the axis 188 is between about 1 degree and about 89 degrees and, in some particular instances, is between about 1 degree and about 75 degrees. In some instances, instead of extending substantially perpendicular to the longitudinal axis 180 (as shown in FIG. 14), the surface defining the distal tip 228 of the marker extends an oblique angle with respect to the longitudinal axis. In some instances, the surface defining the distal tip 228 extends at an angle between about 1 degree and about 89 degrees and, in some particular instances, extends at an angle between about 1 degree and about 75 degrees. The distance the distal tip 228 of the marker 224 extends along the longitudinal axis 180 beyond the pivot axis 176 and/or the angle of the surface defining the distal tip 228 are selected based on the desired field-of-view angle in some instances.

As noted above, in the embodiment of FIGS. 14-16, the marker 224 is configured to reflect energy emitted from the transducer 174 when the transducer reaches the ending orientation of the transducer motion profile (i.e., 60 degrees offset to the right of the longitudinal axis 180 as viewed in FIG. 14). In that regard, referring to FIG. 14, when the transducer 174 is at a 50 degree angle to the right of the longitudinal axis 180, 10 degrees short of the ending orientation, none (or a negligible amount) of the energy emitted by the transducer is reflected by the marker 204 and back onto the transducer. However, referring to FIG. 15, when the transducer 174 is at a 60 degree angle to the right of the longitudinal axis 180 (i.e., at the ending orientation) a portion 232 of the energy emitted by the transducer contacts the marker 224 and reflects a signal 234 back onto the transducer. Referring now to FIG. 16, when the transducer 174 is at a 70 degree angle to the right of the longitudinal axis 180 (i.e., 10 degrees beyond the ending orientation) a portion 236 of the energy emitted by the transducer contacts the marker 224 and reflects a signal 238 back onto the transducer.

Figure 17:
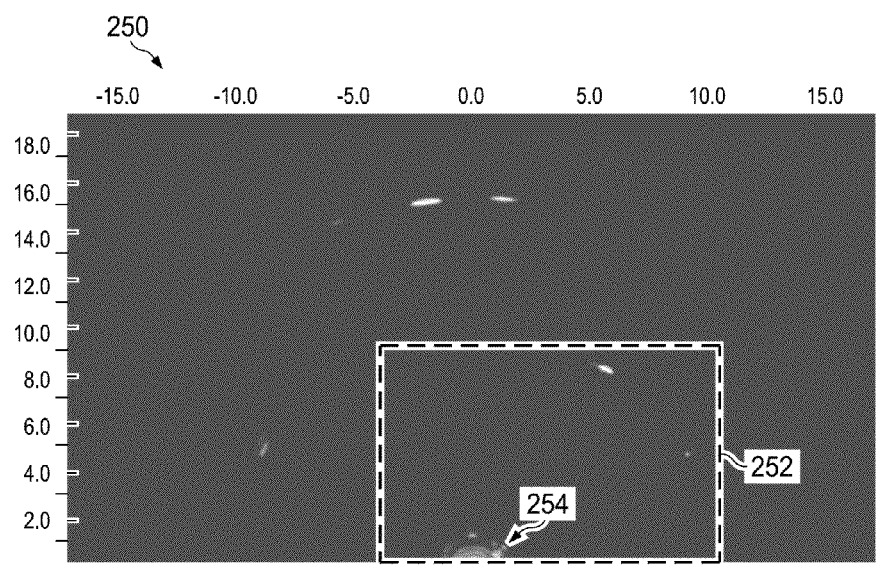
FIG. 17 is an image showing a full field of view of an imaging device having an imaging marker according to an embodiment of the present disclosure.
Figure 18:
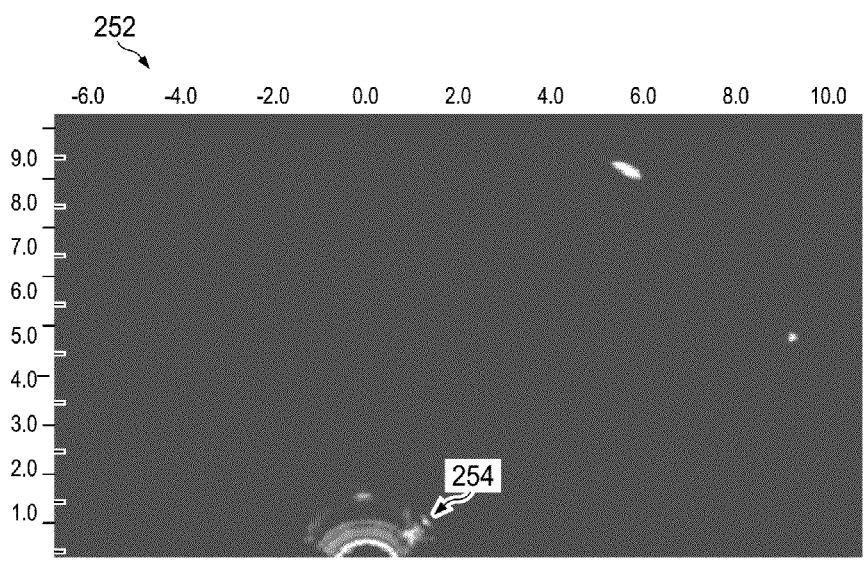
FIG. 18 is a close-up of a portion of the image of FIG. 17 containing the imaging marker.

As the discussed above, markers, such as markers 162, 182, 204, and 224, are incorporated into the distal portions of the imaging devices in some instances, the marker is often positioned between about 0.051 mm (about 0.002 inches) and about 5 mm (about 0.197 inches) from the longitudinal axis of the imaging device. As a result, in some instances the marker is positioned between about 0.0254 mm (about 0.001") and about 1 mm (about 0.0394 inches) from the transducer 174 when the transducer is aimed at the marker such that energy is reflected back towards the transducer from the marker. In contrast, the depth of focus of the transducer or other imaging element used for imaging the anatomy or other structure is typically much larger, for example between about 3 mm and about 15 mm in some instances. In that regard, FIG. 17 shows a full field of view screen shot 250 of an imaging device having an imaging marker according to an embodiment of the present disclosure, while FIG. 18 shows a close-up of a portion 252 of the image of FIG. 17 (as indicated by the dotted-line box) containing the imaging marker. As shown FIGS. 17 and 18, the marker 254 is positioned at a very shallow depth of focus relative to the overall depth of the focus of the imaging device. As a result, the image data at depths where the marker 254 is found is often very noisy. For this reason, in some embodiments this near-field region of the image data is omitted from the display that is provided to a user. However, it is still necessary to identify the marker 254 within the image data. Various techniques suitable for identifying the marker 254 within the noisy signal of the close depth of focus and controlling the field of view of the imaging device based thereon are discussed below.

The imaging targets or markers and the associated field-of-view control techniques of the present disclosure are suitable for use in a wide variety of catheters, guidewires, and other elongate imaging devices having medical applications. In that regard, the targets are incorporated into imaging devices having forward looking and/or side-looking capabilities in some instances. That is, the targets are incorporated into imaging devices that are configured to image generally along the longitudinal axis of the imaging device (i.e., forward-looking) and/or generally perpendicular to the longitudinal axis of the imaging device (i.e., side-looking). Further, in some instances the targets are incorporated into imaging devices that are configured to image at an oblique angle (either distally or proximally) relative to the longitudinal axis of the imaging device. As a result, the field-of-view control techniques of the present disclosure are likewise utilized in the context of forward-looking, side-looking, and oblique-looking imaging devices.

Combinations of one or more of the embodiments of targets and/or field-of-view control techniques described herein can also be used. The small size and relative simplicity of the structures of the markers of the present disclosure make it possible to manufacture imaging devices that utilize two or more markers within a single catheter, guidewire, or other imaging device, including devices ranging from about 0.5 Fr (0.16 mm, 0.006 inches) up to 12 Fr (4 mm, 0.1 inches) or larger in outside diameter or cross-sectional width. For example, in some particular embodiments the feedback mechanisms of the present disclosure are incorporated into guidewires having a diameter of 0.011 inches, 0.014 inches, and/or 0.018 inches.

Figure 19:
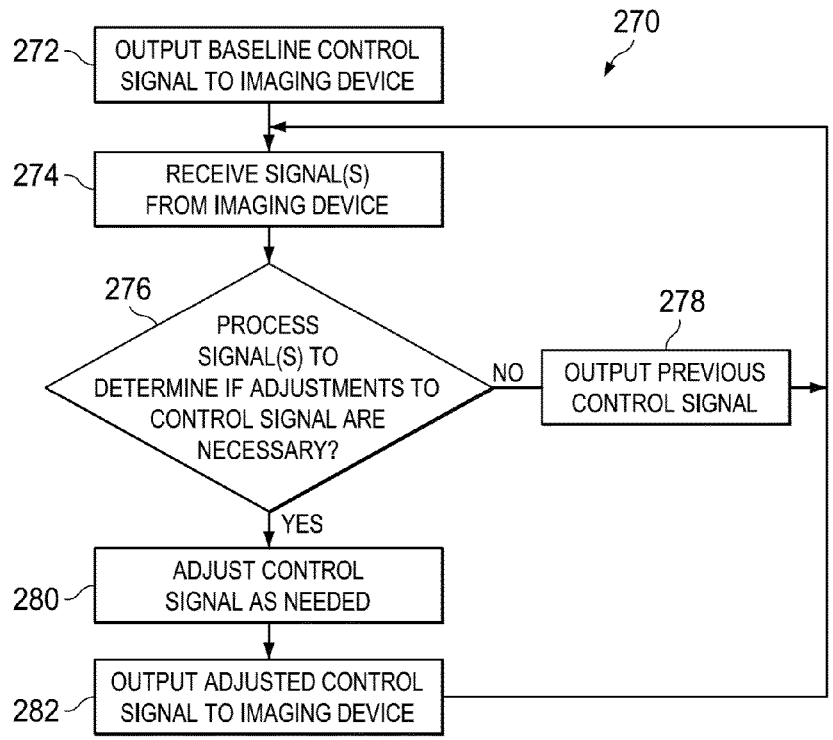
FIG. 19 is a flow chart illustrating a method of controlling a control signal of an imaging system according to an embodiment of the present disclosure.

Referring now to FIG. 19, shown therein is a flow chart illustrating a method 270 of controlling a control signal of an imaging system according to an embodiment of the present disclosure. The method 270 provides a technique that allows a detectable marker, such as those described above, to be utilized to control the field of view of an imaging device. In that regard, method 270 utilizes the data obtained using one or more markers to provide a feedback control loop for more consistent scanning and accurate imaging. The method 270 begins at step 272 with the imaging system providing a baseline control signal to the imaging device, such as the elongated members discussed above. At step 274, signals are received from the imaging device. In some instances, the signals include the imaging data received from the imaging device. At step 276, the signals are processed to determine if any adjustments to the control signal are necessary. In some instances, this processing step includes detecting and identifying the marker(s) within the imaging data to determine a motion profile of the transducer, which corresponds to the field of view of the imaging device. Various techniques for detecting and identifying markers from image data are discussed below. In that regard, one or more of the techniques discussed below are implemented as part of step 276 of method 270 in some instances. Based on the motion profile and/or field of view, it is determined whether any adjustments to the control signal are necessary. If no adjustments are necessary, then the method 270 continues to step 278 where the previous control signal is output to the imaging device again. However, if adjustments to the control signal are necessary, then the method 270 continues to step 280 where the control signal is adjusted based on the signals received from the imaging device at step 274. With the appropriate correction to the control signal calculated at step 280, an adjusted control signal is output to the imaging device at step 282. Then the method 270 continues at step 274 where the feedback signals based on the adjusted control signal are received. This iterative process continues during the operation of the imaging system to provide a consistent transducer motion profile that, in turn, provides accurate imaging.

Figure 20:
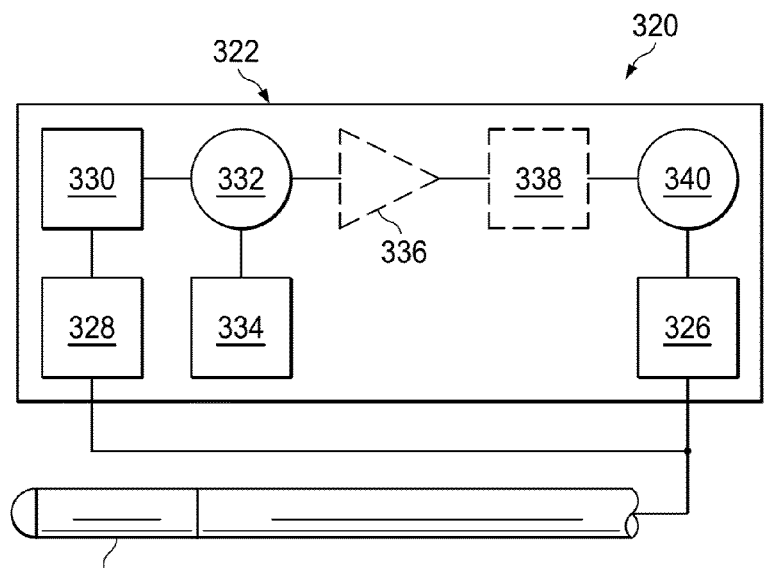
FIG. 20 is a diagrammatic schematic view of a portion of an imaging system according to an embodiment of the present disclosure configured for implementing one or more of the methods of controlling a field of view of an imaging device of the present disclosure.

Referring now to FIG. 20, shown therein is a diagrammatic schematic view of a portion of an imaging system 320 according to an embodiment of the present disclosure. In that regard, the illustrated portion of the imaging system 320 is configured for implementing one or more of the field-of-view control methods of the present disclosure. As shown, the imaging system 320 includes a controller 322 and an imaging device 324. The controller 322 has a control signal output 326 that sends a control signal to the imaging device 324. The controller 322 also receives signals from the imaging device 324 via an input unit 328. Between the input unit 328 and the output unit 326 is a processing pathway that includes a plurality of components 330, 332, 334, 336, 338, and 340. In that regard, the components 330, 332, 334, 336, 338, and 340 are representative of a combination of one or more of a processor, a memory unit, a filter, an amplifier, and/or other component suitable for processing the signals received from the imaging device and controlling the output signal sent from the output unit 326. The specific combination of component types utilized is dependent upon the particular field-of-view control technique(s) to be implemented by the system 320. In that regard, it is understood that the imaging system and, in particular, the controller 322 may include any number and type of electronic components and/or circuitry for performing the field-of-view control techniques of the present disclosure.

Further, it is understood that the various components of the controller may be implemented in hardware, software, firmware, and/or combinations thereof. In that regard, it is also understood that two or more of the various components of the controller may be combined into a single hardware or software component in some instances. Likewise, it is understood that a single component of the controller may be split into two or more hardware or software components in some instances. Further, it is understood that the components of the controller need not be positioned within a single chassis, but instead may be positioned in separate housings and/or be positioned remote from one another. In that regard, it is understood that components of the system may communicate through wired and/or wireless protocols, including communications requiring connection over a network.

Figure 21B:
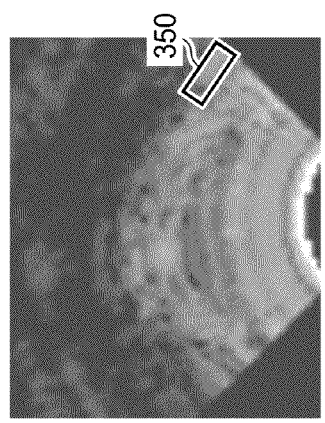
FIGS. 21$a$-21$k$ are a series of images obtained from an imaging device having a visual marker according to an embodiment of the present disclosure, the series of images showing the motion of the visual marker across the field of view of the imaging device.
Figure 21E:
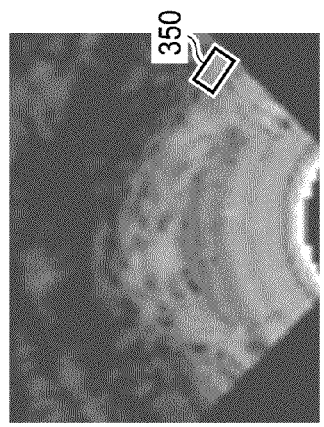
Figure 21A:
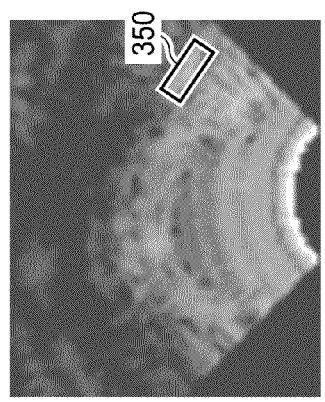
Figure 21D:
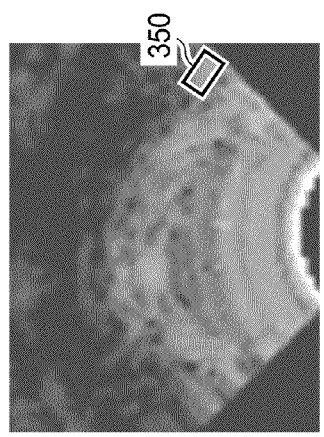
Figure 21C:
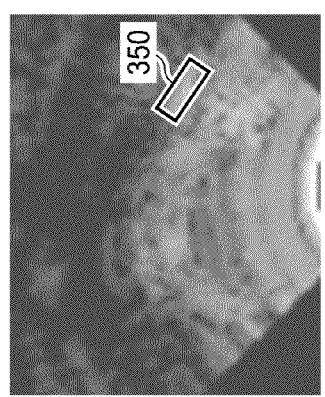
Figure 21F:
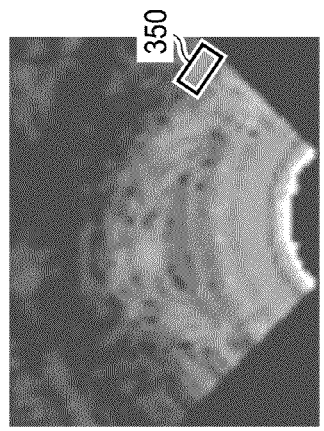
Figure 21I:
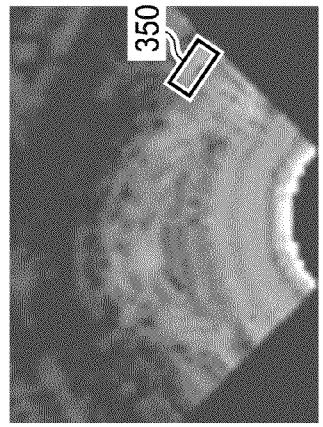
Figure 21H:
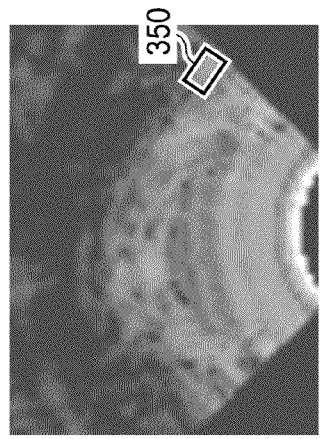
Figure 21G:
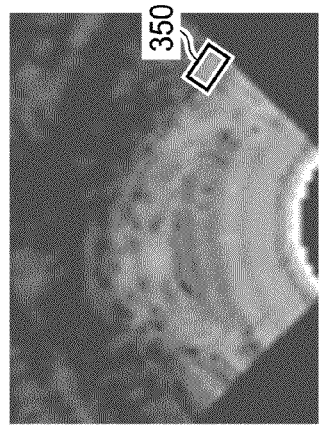
Figure 21K:
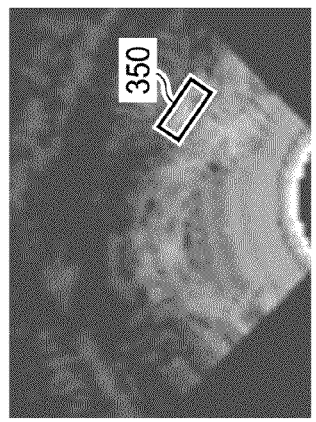
Figure 21J:
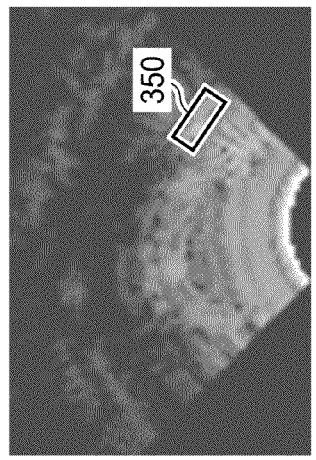

Referring now to FIGS. 21a-21k, shown therein is a series of images obtained from an imaging device having a visual marker according to an embodiment of the present disclosure. In that regard, the series of images show the path of a marker 350 between the frames. In that regard, to make visual identification of the location of the marker 350 easier, FIGS. 21a-21k have been annotated to include a box 350 that is representative of the position of the marker. Each of the frames illustrated in FIGS. 21a-21k are spaced apart by an equal amount of time or number of frames. In the specific data set utilized to generate FIGS. 21a-21k, each of the illustrated frames is separated by 1 second and 9 frames such that, for example, the image of FIG. 21a corresponds to Frame 0 taken at time 0, the image of FIG. 21b corresponds to Frame 10 taken at time 1.0 s, the image of FIG. 21c corresponds to Frame 20 taken at time 2.0 s, and so on. Taken together, the series of images show the motion of the visual marker across the field of view of the imaging device. In the illustrated data set, the marker 350 begins within the field of view of the imaging device (as shown in FIG. 21a) moves further to the right until it is partially out of the field of view (as shown in FIG. 21f, for example) and then moves back to the left and fully within the field of view again (as shown in FIG. 21k). The imaging dataset corresponding to the series of images shown in FIGS. 21a-21k are utilized below in the context of a thresholding algorithm and a running average algorithm for identifying the marker 350.

Figure 22C:
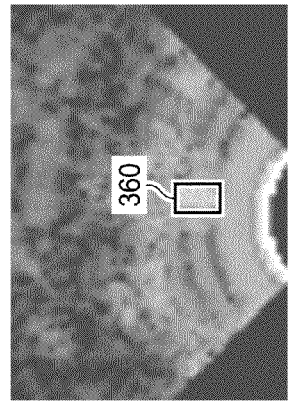
FIGS. 22a-22k are a series of images obtained from an imaging device having a visual marker according to another embodiment of the present disclosure, the series of images showing the motion of the visual marker across the field of view of the imaging device.
Figure 22F:
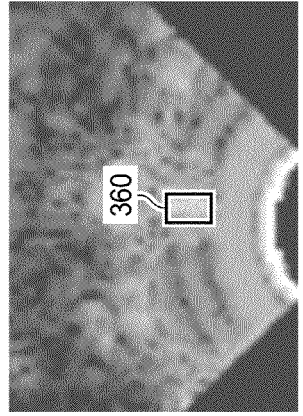
Figure 22B:
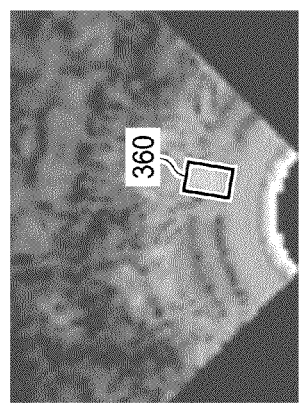
Figure 22E:
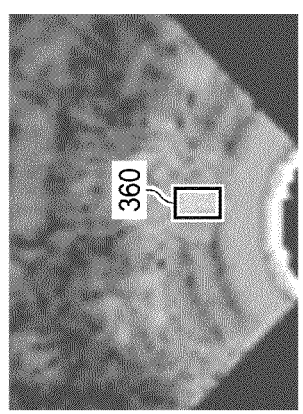
Figure 22A:
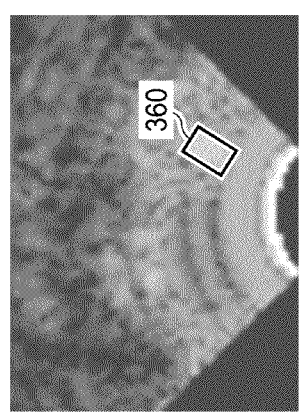
Figure 22D:
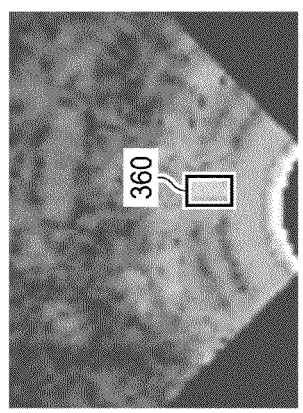
Figure 22G:
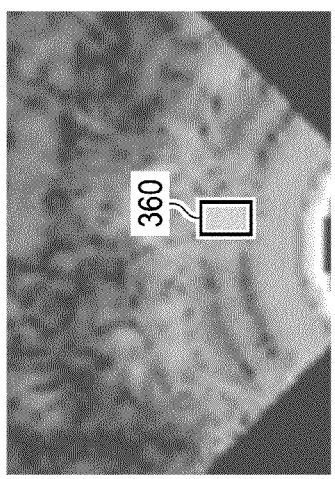
Figure 22H:
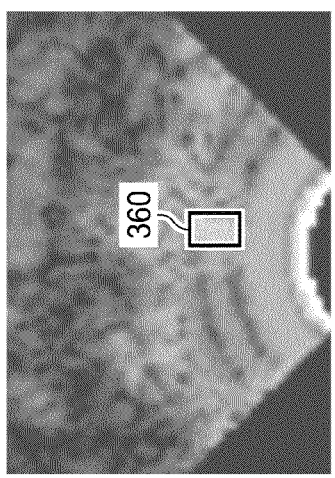
Figure 22I:
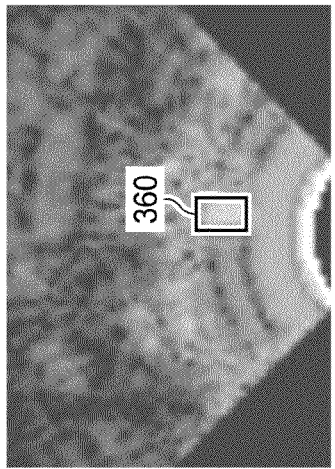
Figure 22J:
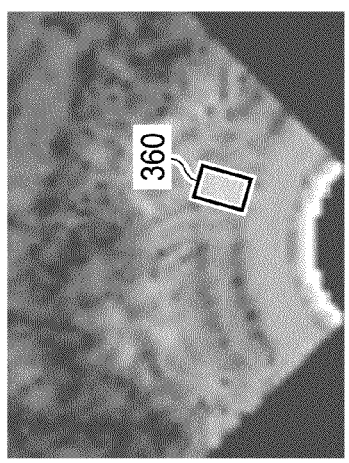
Figure 22K:
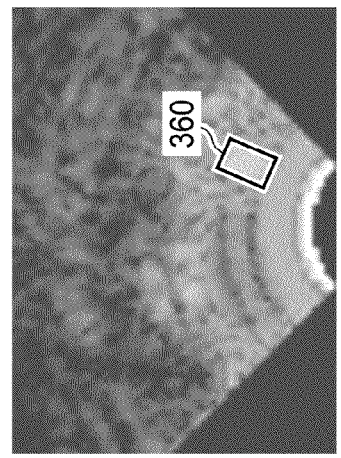

Referring now to FIGS. 22a-22k, shown therein is a series of images obtained from another imaging device having a visual marker according to another embodiment of the present disclosure. In that regard, the series of images show the path of a marker 360 between the frames. In that regard, to make visual identification of the location of the marker 360 easier, FIGS. 22a-22k have been annotated to include a box 360 that is representative of the position of the marker. Each of the frames illustrated in FIGS. 22a-22k are spaced apart by an equal amount of time or number of frames. In the specific data set utilized to generate FIGS. 22a-22k, each of the illustrated frames is separated by 1 second and 9 frames such that, for example, the image of FIG. 22a corresponds to Frame 0 taken at time 0, the image of FIG. 22b corresponds to Frame 10 taken at time 1.0 s, the image of FIG. 22c corresponds to Frame 20 taken at time 2.0 s, and so on. Taken together, the series of images show the motion of the visual marker across the field of view of the imaging device. In the illustrated data set, the marker 360 begins within the field of view of the imaging device on the right hand side of the image (as shown in FIG. 22a) moves left towards the middle of the image (as shown in FIGS. 22e and 22f, for example) and then moves back to the right to the right hand side of the image again (as shown in FIG. 22k). The imaging dataset corresponding to the series of images shown in FIGS. 21a-21k are utilized below in the context of a thresholding algorithm and a running average algorithm for identifying the marker 360.

Referring now to FIG. 23, shown therein is a graph 370 illustrating the tracking of the markers 350 and 360 of FIGS. 21a-21k and FIGS. 22a-22k according to an embodiment of the present disclosure. More specifically, the graph 370 illustrates the tracking of the markers 350 and 360 utilizing a thresholding algorithm of the present disclosure. In that regard, the thresholding algorithm operates based on the assumption that the marker 350, 360 will have the highest amplitude reflection within a predefined region, such as a particular depth of field range. As discussed above with respect to FIGS. 17 and 18, because the region of focus of an imaging is typically much greater than the region of focus where the marker will appear, in most instances there will be no tissue reflectors of interest in the near-field of the imaging device. Accordingly, the presence of the marker can be identified by identifying a reflector within a region of interest (e.g., a particular depth or range of depths) in the imaging data that meets a predefined threshold. The particular region of interest may be selected based on factors such as the expected depth of marker relative to the transducer, the angle position of the marker relative to the total field of view, and/or combinations thereof. The actual value(s) of the threshold utilized can vary greatly between imaging devices and even different applications of a single imaging device. For example, in some instances the threshold value is selected based on one or more of: system gain (analog and digital, including depth gain control ("DGC")), transmit amplitude, marker proximity to transducer, marker structure, marker orientation, marker material, manufacturing tolerances of markers, transducer insertion loss, sensitivity, and/or combinations thereof. Accordingly, in some instances the threshold value ranges between about −40.0 dB and about −10.0 dB, but in other instances the threshold value is outside (greater than or less than) the values of this range. With respect to the datasets of FIGS. 21a-21k and FIGS. 22a-22k that were utilized in generating the graph 370, a threshold value of −20.0 dB was utilized. In that regard, line 372 of graph 370 is representative of the dataset of FIGS. 21a-21k, while line 374 is representative of the dataset of FIGS. 22a-22k.

In some embodiments, the thresholding algorithm utilizes the following to determine marker location:

$$\text{if } \underset{u=u1}{\overset{u=u2}{A}}(u, v) \geq A_t$$
$$Y(n) = v$$
$$\text{else}$$
$$Y(n) = NaN$$
$$\text{end}$$

where:
A(u, v) is the echo amplitude at sample number u from samples u1 to u2 for A–Scan v
Y(n) is an array of length n whose elements are A–Scans that contain fir marker.

This algorithm is performed for each A-Scan such that a one-dimensional depth value is provided for each A-scan. In some instances, the depth output is provided as a single sample out of all samples within a single A-Scan. Accordingly, Y(n) provides an array of all the A-scans within a frame in which the threshold value is exceeded. The final marker location for the B-scan associated with a collection of A-scans is determined based on Y(n). In that regard, in some embodiments the final marker location is selected as the average of the sample numbers of Y(n). In other embodiments, the final marker location is selected as the median of the sample numbers of Y(n). In yet other embodiments, other computational techniques are utilized to select the final marker location based on the collection of A-scans determined based on Y(n).

Referring now to FIG. 24, shown therein is a graph 380 illustrating the tracking of the markers 350 and 360 of FIGS. 21a-21k and FIGS. 22a-22k according to another embodiment of the present disclosure. More specifically, the graph 380 illustrates the tracking of the markers 350 and 360 utilizing a running average algorithm of the present disclosure. In some instances, the running average algorithm utilizes an n-line average filter. In that regard, the running average is computed for one or more A-scans and subsequent A-scans are compared against that running average. Accordingly, if the peak reflector in an A-scan exceeds the peak of the running average by a predefined threshold, then the marker has been detected. Similar to the thresholding algorithm discussed above, in some instances only a region of interest (e.g., a particular depth or range of depths) of the image data is considered when evaluating in the imaging data to identify the marker. In that regard, the particular region of interest may be selected based on factors such as the expected depth of marker relative to the transducer, the angle position of the marker relative to the total field of view, and/or combinations thereof.

The presence of the marker can be identified by identifying a reflector within the region of interest that is greater than the running average by a predefined threshold. Again, the actual value(s) of the threshold utilized can vary greatly between imaging devices and even different applications of a single imaging device. For example, in some instances the threshold value is selected based on one or more of: system gain (analog and digital, including depth gain control ("DGC")), transmit amplitude, marker proximity to transducer, marker structure, marker orientation, marker material, manufacturing tolerances of markers, transducer insertion, sensitivity, and/or combinations thereof. Accordingly, in some instances the threshold value ranges between about 5 dB and about 10 dB, but in other instances the threshold value is outside (greater than or less than) the values of this range. With respect to the datasets of FIGS. 21a-21k and FIGS. 22a-22k that were utilized in generating the graph 380, a threshold value of 8.5 dB was utilized. In that regard, line 382 of graph 380 is representative of the dataset of FIGS. 21a-21k, while line 384 is representative of the dataset of FIGS. 22a-22k. The reflector in this data also requires a threshold, which is determined to be 8.5 dB in this data set. This reflector is also highly variable, again dependent on the application settings.

In contrast to the thresholding algorithm discussed above, the running average algorithm operates on an entire B-Scan as opposed to singular A-scans. In that regard, in some instances the running average algorithm utilizes the following to determine marker location:

$$A_{avg}(u, v) = \frac{\sum_{v}^{v+\Delta v} A(u, v)}{\Delta v}$$

$$\text{if } \frac{\sum_{u=u1}^{u2} A(u,v)}{u2-u1} \geq \frac{\sum_{u=u1}^{u2} A_{avg}(u,v)}{u2-u1}$$

$$Y(n) = v$$

else $$Y(n) = NaN$$

end where:

$A_{avg}$ is the average echo amplitude over $\Delta v$ A-scans for a sample u $$\frac{\sum_{u=u1}^{u=u2} A(u,v)}{u2-u1}$$

is the mean echo amplitude for an A-Scan v for samples between u2 and u1

$$\frac{\sum_{u=u1}^{u=u2} A_{avg}(u,v)}{u2-u1}$$

is the mean echo amplitude for group of $\Delta v$ A-Scans for samples between u2 and u1 Y(n) is an array representing all A-Scans that contain dr marker As a result, Y(n) provides an array of all the A-Scans in which the marker is detected within a frame. The final marker location for the B-scan is determined based on Y(n). In that regard, in some embodiments the final marker location is selected as the average of the sample numbers of Y(n). In other embodiments, the final marker location is selected as the median of the sample numbers of Y(n).

Referring now to FIGS. 25-27b, shown therein are aspects of a method 400 of controlling a control signal of an imaging system according to an embodiment of the present disclosure incorporating a correlation or template matching algorithm. Referring more specifically to FIG. 25, shown therein is a flow chart of the method 400. The method 400 starts at step 402 where a template of the marker is obtained. In that regard, imaging markers typically have unique or at least identifiable characteristics that is consistent from frame to frame, which may be considered the marker's signature. Accordingly, these identifiable characteristics of the marker can be utilized to create a template suitable for identifying the marker in other imaging data or frames. Due to various reasons, different imaging devices will have variances in the physical shape and location of the marker(s). As a result, a marker of one device can have different characteristics than a marker of another device (including devices intended to be identical to one another). As a result, in some instances a unique or custom template is utilized for each imaging device. In other instances, a common template is utilized across a plurality of imaging devices having similar arrangements and/or markers.

A template for a particular imaging device or group of imaging devices can be computed in a variety of ways. In some instances, the template is determined during manufacturing and stored on a memory device (such as an RFID tag) associated with the device. In other instances, the template is calculated at the beginning of use (in some instances, each use) by initially over-driving the actuator to ensure that the marker will be present in the initial image(s) obtained by the device. The location of the marker within the initial images is determined using thresholding methods (e.g., the thresholding algorithm discussed above), averaging methods (e.g., the running average algorithm discussed above), and/or other suitable techniques. In some instances, the template is a pixel intensity map or heat map of a region of an image containing the marker. For example, FIG. 26 provides an image 420 showing identification of a region 422 associated with a marker suitable for creating a template for use in a correlation algorithm of the present disclosure. More specifically, FIG. 26 is a pre-scan converted image where the x-axis is A-scan number (corresponding to angle), the y-axis is depth, and the color intensity indicates returned signal in dB. By identifying the marker within the image, a region 422 containing the marker can be utilized as the template.

Referring again to FIG. 25, once this template is obtained at step 402, the method 400 continues at step 404 by computing the correlation of the template with the current image. In other words, the method determines how closely the current image matches the template. In some instances, the following equation is utilized to calculate the cross correlation of the template and the image at position (u, v):

$$C(u,v) = \frac{\sum_{x,y} [I(x,y) - \bar{I}_{u,v}][T(x-u, y-v) - \bar{T}]}{\sqrt{\sum_{x,y} [I(x,y) - \bar{I}_{u,v}]^2 \sum_{x,y} [T(x-u, y-v) - \bar{T}]^2}}$$

where:

C(u, v) is the normalized cross-correlation with the template centered at pixel (u, v) where u indicates the depth location and v indicates the A-scan number I is the original image T is the template $\bar{I}^{u,v}$ is the mean of the original image in the region overlapping the template $\bar{T}$ is the mean of the template This equation is applied to all pixels within the search region or region of interest of the image such that the cross correlation of the template and the current image is calculated for various possible locations of the marker. The correlation is maximized where the template and image have the strongest match in relative amplitude. Since the marker is typically at a fixed location relative to the transducer, the marker will appear at approximately the same y distance (i.e., depth or distance along an A-scan) in each image.

Referring more specifically to FIGS. 27a and 27b, shown therein is a plot of the cross-correlation results for an exemplary frame of a dataset relative to a corresponding template. In that regard, FIG. 27a is a heat map 430 showing the cross-correlation values for the entire image, including an area 432 of maximum correlation. FIG. 27b is a close-up of the portion of the heat map of FIG. 27a containing the area 432 of maximum correlation. While FIG. 27a illustrates the cross-correlation values for the entire image, in some instances it is not necessary to calculate the cross-correlation for the entire image since the marker will only be detected in a limited region of interest of the image. Accordingly, to increase computational speed the correlation is computed for the pre-defined search region in some instances. In that regard, the selected search region may be selected based on one or more of the following: distance of marker relative to the transducer (i.e. depth marker should appear in image), angular extent of marker relative to the FOV, maximum anticipated frame-to-frame change in angle coverage, marker location in previous image, and/or combinations thereof.

Referring again to FIG. 25, in some instances, the method 400 continues at step 406 by limiting the search region of the image based on one or more of the factors discussed above. In some particular embodiments, the search region is limited based on image depth and the maximum expected transducer motion from one frame to the next. In other embodiments, the method 400 omits step 406 and the entire image is utilized as the search region.

At step 408, the point of maximum correlation between the image and the template is identified within the limited search region (if the method 400 includes step 406) or within the entire image (if step 406 is omitted). In that regard, the point where the correlation is maximized is considered to be the marker location. Once the marker location is found for the current frame at step 408, the method 400 continues at step 410 where the marker position is updated and the energy provided to the actuator of the imaging device that imparts motion on the imaging element is adjusted, as necessary, to ensure that the motion profile of the imaging transducer results in the marker being at the desired location(s) within the subsequent image(s). Steps 404, 406 (optional), 408, and 410 are repeated continuously or intermittently during operation of the imaging device to control the field of view of the imaging device.

Referring now to FIGS. 28-31, shown therein are aspects of a method 440 of controlling a control signal of an imaging system according to an embodiment of the present disclosure incorporating a reverse correlation or template matching algorithm. In that regard, the reverse correlation algorithm uses a template matching technique similar to that discussed above with respect to method 400, but the template is formed based on a region of image data that does not contain the marker. For example, in some embodiments, the first portion of the image depth of an imaging device (e.g., less than 10 mm, less than 5 mm, or otherwise) has a return signal with fairly constant amplitude across A-scans except when the marker is present. Accordingly, by generating a template of the constant amplitude signal (i.e., non-marker region) and correlating that with a frame, the correlation will be high everywhere except where the marker is located. Since this version of the template matching algorithm is looking for areas with low correlation to the template to identify the marker region, it is referred to as a reverse correlation algorithm in some instances.

Referring more specifically to FIG. 28, shown therein is a flow chart of the method 440. The method 440 starts at step 442 where a template of the non-marker or constant signal region is obtained. In that regard, FIG. 29 provides an image 460 showing identification of a constant signal region 462 suitable for creating a template for use in a correlation algorithm of the present disclosure and a region 464 associated with the presence of a marker. More specifically, FIG. 29 is a pre-scan converted image where the x-axis is A-scan number (corresponding to angle), the y-axis is depth, and the color intensity indicates returned signal in dB. By identifying the region 462 within the image where the marker could be found but is not found, a template can be created. In that regard, in some instances the template is formed by one or more unfiltered samples within the region 462. In other instances, the template is defined by filtering across multiple A-scans. For example, the template is defined by averaging across a plurality of A-scans within the region 462 in some embodiments.

Referring again to FIG. 28, once the template is obtained at step 442, the method 440 continues at step 444 by computing the correlation of the template with the current image. In other words, the method determines how closely the current image matches the template. In some instances, the same equation discussed above with respect to the cross correlation calculation of the method 400 is utilized to calculate the cross correlation of the template and the image at position (u,v) for method 440. In that regard, the equation is applied to all pixels within the search region or region of interest of the image such that the cross correlation of the template and the current image is calculated for various possible locations of the marker. The correlation is maximized where the template and image have the strongest match in relative amplitude and minimized where the template and image have the weakest match.

Referring more specifically to FIG. 30a, shown therein is a plot of the cross-correlation results for an exemplary frame of a dataset relative to a corresponding template. In that regard, FIG. 30a is a heat map 470 showing the cross-correlation values for an entire image, but where a marker is expected to be visible at a depth of approximately 36 pixels. Referring again to FIG. 28, in some instances, the method 440 continues at step 446 by limiting the search region of the image based on one or more of the factors discussed above with respect to the method 400. In some particular embodiments, the search region is limited based on image depth. For example, FIG. 30b provides a graph 472 showing the cross-correlation values at the $36^{th}$ pixel depth.

Referring again to FIG. 28, at step 448, the point of minimum correlation between the image and the template is identified within the limited search region (if the method 400 includes step 446) or within the entire image (if step 446 is omitted). In that regard, the point where the correlation is minimized is considered to be the marker location. For example, where the search region is limited to a pixel depth of 36, as shown in FIG. 30b, the point of lowest correlation is identified near A-scan 185. FIG. 31 is a heat map 480 showing cross-correlation between a template and a dataset of 200 frames. The relative position of the marker between frames is illustrated by the cross-correlation values. In some instances, the marker location is determined by the median A-scan meeting a threshold of minimum correlation (i.e., A-scans having a cross-correlation less than the threshold value).

Referring again to FIG. 28, once the marker location is found for the current frame at step 448, the method 440 continues at step 450 where the marker position is updated and the energy provided to the actuator of the imaging device that imparts motion on the imaging element is adjusted, as necessary, to ensure that the motion profile of the imaging transducer results in the marker being at the desired location(s) within the subsequent image(s). Steps 444, 446 (optional), 448, and 450 are repeated continuously or intermittently during operation of the imaging device to control the field of view of the imaging device.

Figure 32:
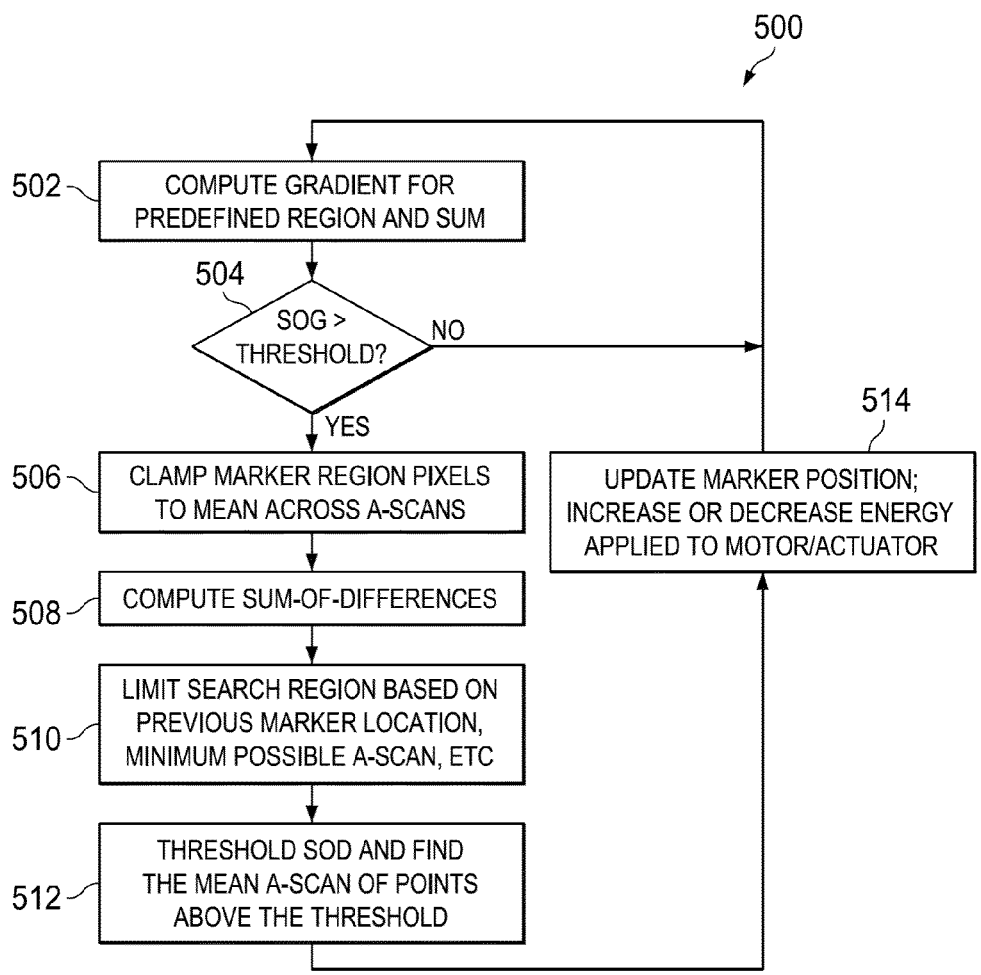
FIG. 32 is a flow chart illustrating a method of controlling a control signal of an imaging system according to an embodiment of the present disclosure incorporating a sum-of-differences and sum-of-gradient algorithm.
Figure 33:
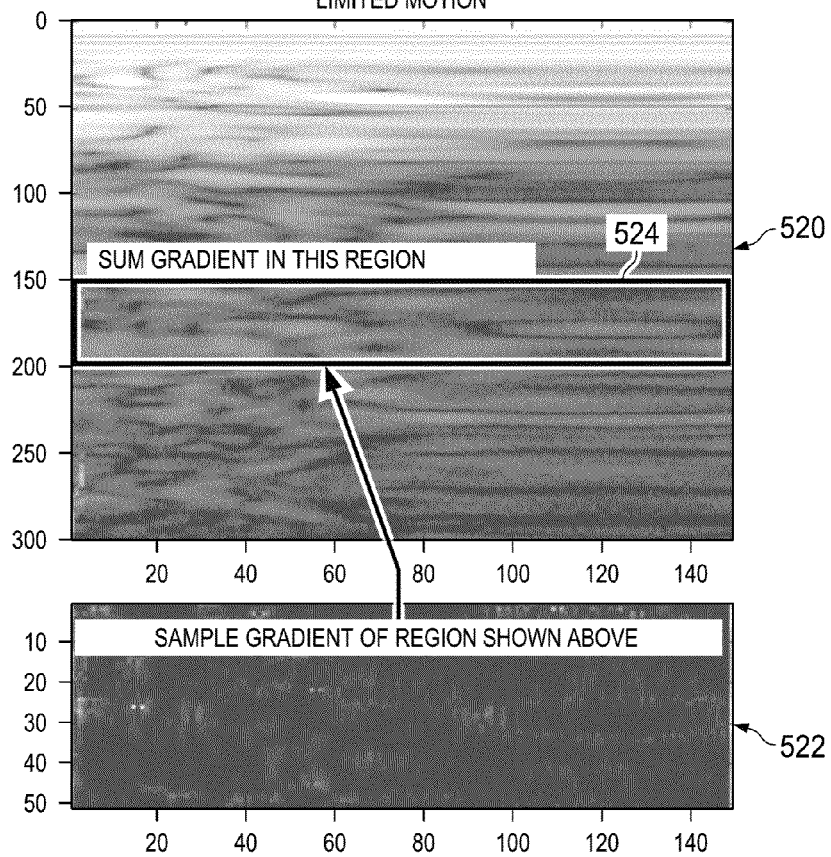
FIG. 33 is an image corresponding to limited transducer motion and a graph of the gradient of a portion of the image corresponding to the limited transducer motion according to an embodiment of the present disclosure.
Figure 34:
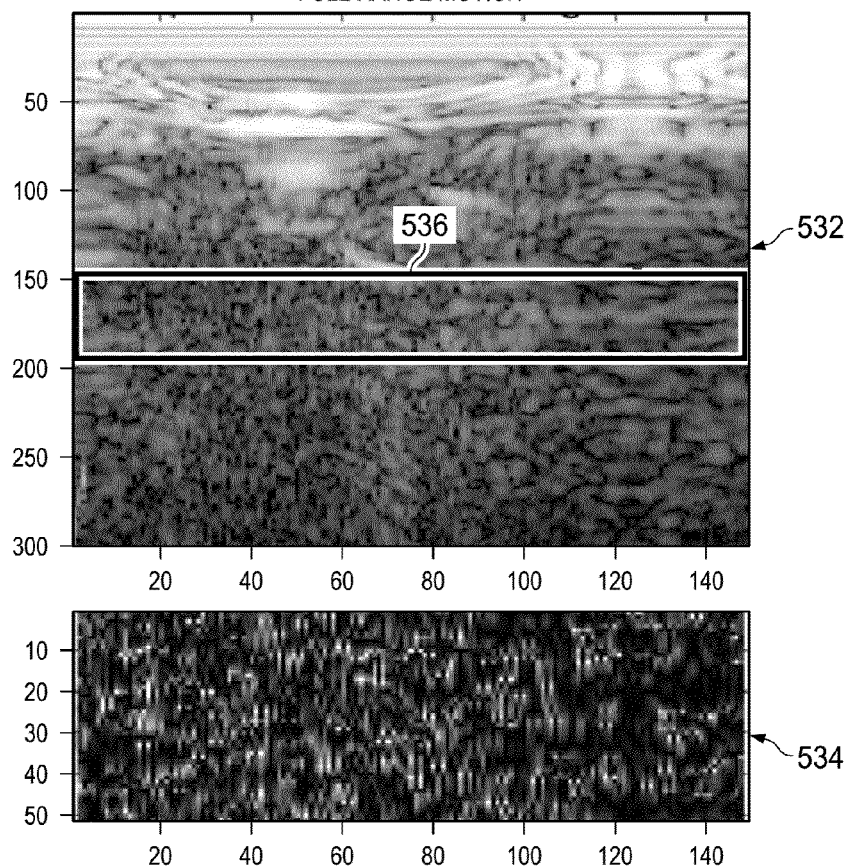
FIG. 34 is an image corresponding to full-range transducer motion and a graph of the gradient of a portion of the image corresponding to the full-range transducer motion according to an embodiment of the present disclosure.

Referring now to FIGS. 32-46, shown therein are aspects of techniques for controlling a control signal of an imaging system according to embodiments of the present disclosure that incorporate a sum-of-differences and sum-of-gradient algorithm. In some embodiments, the sum-of-differences and sum-of-gradient algorithm utilizes at least some features similar to the methods of identifying a marker discussed above. Referring to FIG. 32, shown therein is a flow chart of a method 500 incorporating a sum-of-differences and sum-of-gradient algorithm. The method 500 begins at step 502 where the gradient is computed over a pre-defined region across A-scans of an image (B-scan). In that regard, the pre-defined region or region of interest of the image may be selected based on one or more of the factors discussed above with respect to the other techniques for identifying the marker. The computed gradient within the pre-defined region are summed for all pixels within that region. In some instances the gradient of the image is approximated using a convolution operator. For example, in some embodiments the following convolution operator is utilized:

$$SOG = \Sigma_{u,v} G_x(u,v)$$

$$G_x = I_L * [-1\ 0\ 1]$$

where:
SOG is the final Sum of Gradients for a single frame
$G_x$ is an approximation of the horizontal gradient
$I_L$ is the original image limited to the SOG region
* indicates the 2D convolution operator At step 504 of the method 500, the sum-of-gradient calculation is utilized to determine if there is sufficient transducer motion to warrant attempting to identify a marker location. In that regard, the sum-of-gradient is compared to a threshold value indicative of transducer motion. If there is very little motion, then the image will have fairly constant signal across A-scans and, therefore, a corresponding low gradient. In that regard, FIG. 33 shows an image 520 that is representative of limited or no transducer motion. FIG. 33 also includes a graphical representation 522 that shows the gradient for region 524 of image 520. As shown in the graphical representation 522, the region 524 has a low and relatively constant gradient. In contrast, FIG. 34 shows an image 530 that is representative of full-range transducer motion. FIG. 34 also includes a graphical representation 532 that shows the gradient for region 534 of image 530. As shown in the graphical representation 532, the region 524 has a widely varying gradient that is indicative of transducer motion. In some instances, to determine if sufficient motion is present for the marker to be present in the image, the absolute value of the gradient is summed across all pixels in the region of interest and compared to the threshold value.

For example, FIG. 35 provides a line graph 540 of the sum-of-gradient across a plurality of frames of a dataset. As shown, the graph 540 includes a line 542 that is representative of the value of the sum-of-gradient for each frame of the dataset and a line 544 that is threshold value for the dataset. As shown, the first approximately 75 frames have insufficient gradient to meet the threshold value represented by line 544, while the remaining frames exceed the threshold value. In some instances the failure to meet the threshold value is an indication that more energy is needed to move the transducer to reach a desired field-of-view. Accordingly, in some embodiments, when the sum-of-gradient does not meet the threshold value the method 500 continues by increasing the power or energy provided to the actuator of the imaging device and returns to step 502 to calculate the resulting gradient. This process of increasing the power or energy and calculating the gradient is repeated until the sum-of-gradient meets the threshold value, exceeds the threshold value by a predetermined amount, meets the threshold value for a predetermined number of frames, and/or otherwise reaches a gradient value that indicates the presence of the marker is likely to be found in the image(s).

Referring again to FIG. 32, once the sum-of-gradient passes the threshold value for a frame, the method 500 continues to step 506 where the pixel values are clamped to the mean value across all A-scans. Clamping is done in step 506 to prevent extremely low intensity pixels around the marker from interfering with detection of the marker using a sum-of-differences calculation. In that regard, FIG. 36 provides a first graphical representation 550 of a region containing a marker before clamping or without clamping and a second graphical representation 552 that shows the same region after clamping. As shown, clamping cleans up the image by removing the low-intensity pixels from around the marker. In some instances, the following calculations are utilized to perform the image clamping:

if $I(u, v) < M_{row}(u)$
$I_{clamp}(u, v) = M_{row}(u)$
else
$I_{clamp}(u, v) = I(u, v)$
end $$M_{row}(u) = \frac{\sum_{i=1}^{n_A} I(u, v)}{n_A}$$

where:
$I_{clamp}$ is the resulting image after clamping the minimum value to the mean of each row
$M_{row}(u)$ is the mean of the image across row (or depth position) u
$I(u, v_i)$ is the value of the image at row (or depth position) u and column (or A-scan) v
$n_A$ is the total number of columns (A-scans) in the image
In some instances, the method 500 omits step 506.

Figure 37:
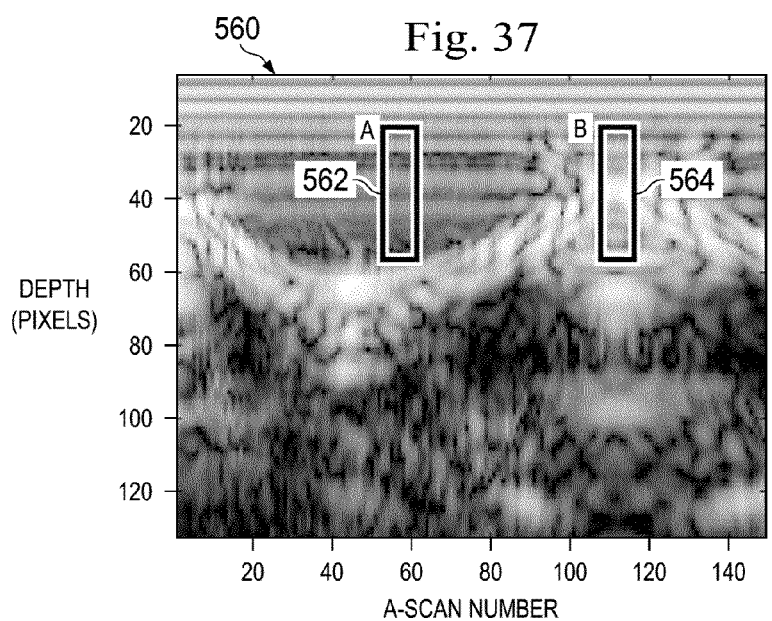
FIG. 37 is an image showing identification of a first window and a second window utilized in a sum-of-differences algorithm according to an embodiment of the present disclosure.
Figure 38:
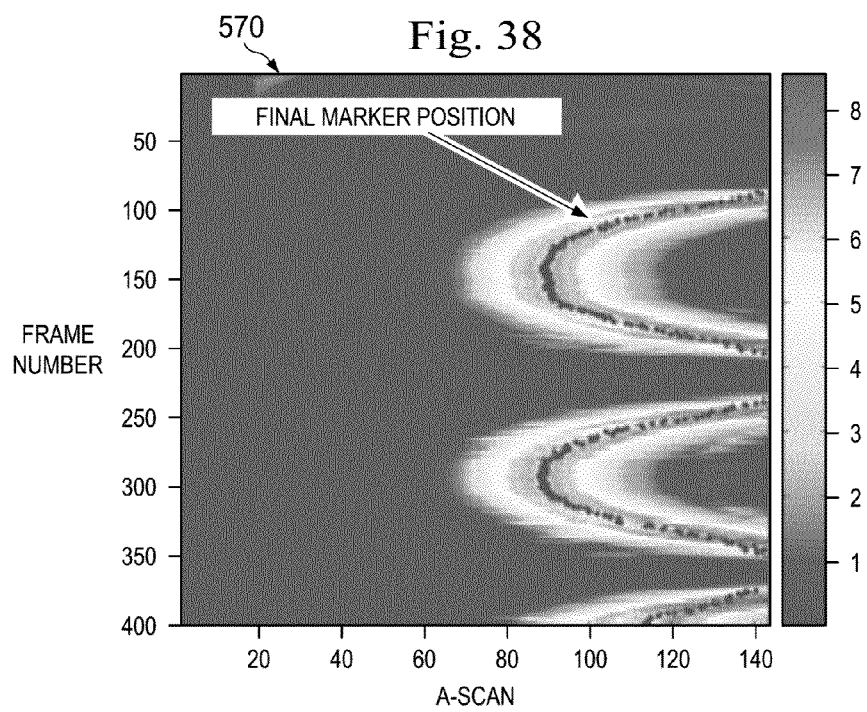
FIG. 38 is a heat map showing detection of an imaging marker across a plurality of frames of a dataset according to an embodiment of the present disclosure.

Referring again to FIG. 32, after clamping of the image at step 506, the method 500 continues to step 508 where the sum-of-differences is calculated. In that regard, for identification of the marker, the sum-of-differences algorithm assumes that the A-scans that contain the marker will have a higher amplitude within the pre-defined region of interest (e.g., depth(s) where marker is expected to be detected) than the other A-scans of an image. In order to detect this difference in amplitude, a sliding window is compared with a window at half the A-scan distance (i.e., half the angle) and the difference between the two windows are summed. For example, in some instances the following equation is utilized:

$$SOD(u, v) = \sum_{x=u-h}^{u+h} \sum_{y=v-w}^{v+w} \left[ I_{clamp}(x, y) - I_{clamp}\left(x, y - ceil\left(\frac{v}{2}\right)\right) \right]$$

where:
SOD(u,v) is the final Sum of Difference for position(u, v)
$I_{clamp}$ is the clamped image
h is half the height of the desired SOD window
w is half the width of the desired SOD window
ceil is the ceiling operator Referring to FIG. 37, shown therein is an image 560 illustrating the use of windows as discussed above. In that regard, image 560 includes a first window 562 and a second window 564 that are used for differencing. In particular, the sum-of-differences is calculated as the sum of the difference between the window 564 and the window 562. In that regard, window 564 is translated from left to right across the image. As window 564 is moved across the image 560, window 562 is also moved across the image such that window 562 is positioned halfway between A-scan #1 and window 564. FIG. 38 provides a heat map 570 showing detection of an imaging marker by computing the sum-of-differences across all A-scans and frames of a sample dataset. The marker is visually identified in the heat map 570 as the region with the highest sum-of-differences. In that regard, a final marker position is also identified for each image. In that regard, the specific A-scan(s) associated with the final marker position of an image may be selected based on the mean value, the median A-scan of A-scans where the marker is present, and/or any other suitable method. This sum-of-differences technique exploits the fact that, for imaging devices where the marker is positioned at or near the end of the desired range of motion of the transducer, when the transducer is at half its full range of motion the region of interest should have a relatively low amplitude signal and when the transducer is at its maximum field of view the region of interest should have the highest average amplitude due to the presence of the marker.

Referring again to FIG. 32, once the sum-of-differences is computed for an individual frame, the method 500 continues at step 510 where the search region or region of interest is then limited based on the previous marker location and the maximum movement between frames. In some embodiments, the method 500 omits step 510. After step 510, the method 500 continues to step 512 where the sum-of-differences is compared to a threshold value. In that regard, the threshold may be based on one or more of the following: an average sum-of-differences, a maximum sum-of-differences, a minimum sum-of-differences, a median sum-of-differences, an absolute threshold based on the expected minimum value, and/or combinations thereof. In some instances, multiple threshold values are utilized. For example, in one embodiment two threshold values are utilized. The first threshold is utilized to find all points above a minimum average sum-of-differences, while the second threshold is utilized to find all points that have a sum-of-differences value of greater than a certain percentage of the maximum sum-of-differences. Accordingly, A-scans that are above both of these thresholds are indicative of marker detections. In some particular embodiments of the present disclosure, the minimum average sum-of-differences is between about 1 dB and about 15 dB, but in other instances the minimum average sum-of-differences is outside (greater than or less than) the values of this range. In some instances, the percentage of the maximum sum-of-differences is between about 25% and about 90%. In one specific implementation of such a technique, the minimum average sum-of-differences is 3 dB and the percentage of the maximum sum-of-differences is 75%. As noted above, the final marker position can be defined as the median A-scan of A-scans where the marker is present, a mean of the A-scans where the marker is present, and/or any other suitable method. In some embodiments of the method 500, the sum-of-differences is utilized without the sum-of-gradient threshold calculations. In other words, in some embodiments, steps 502, 504, and 506 are omitted.

Figure 39:
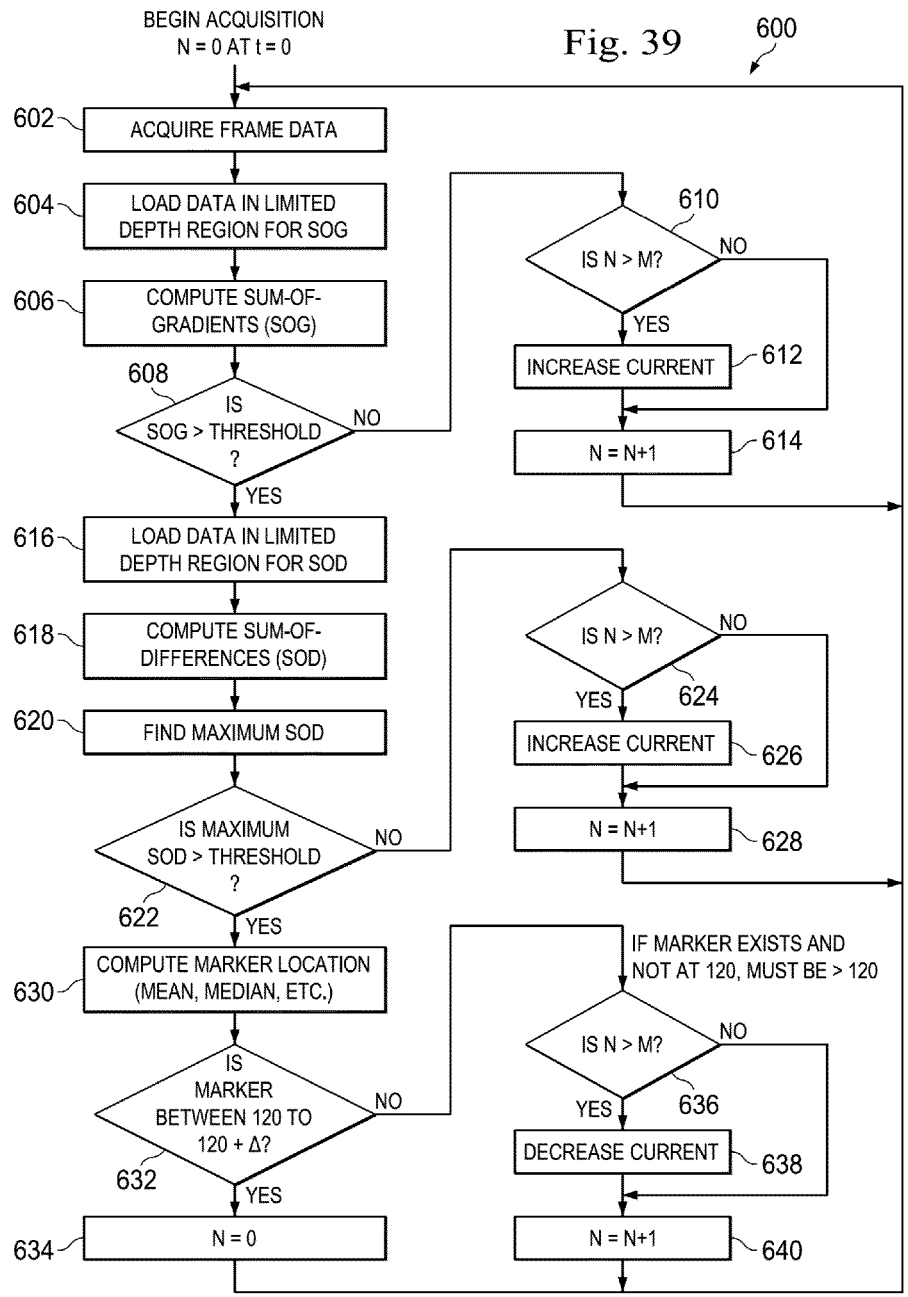
FIG. 39 is a flow chart illustrating a method of controlling a control signal of an imaging system according to an embodiment of the present disclosure incorporating a sum-of-differences and sum-of-gradient algorithm.

Referring now to FIG. 39, shown therein is a flow chart for a method 600 of implementing a sum-of-gradient and sum-of-differences algorithm according to an embodiment of the present disclosure. The method 600 begins at step 602 with acquiring image frame data. Once the frame data has been acquired, then the method 600 continues at step 604 where the data is loaded into a sum-of-gradient algorithm. The loaded data is limited to a predefined depth region in which significant signal variation is expected when the transducer is moving. With the data loaded and limited to the region of interest, the method 600 continues at step 606 where the sum-of-gradient is calculated and then compared to a threshold at step 608.

If the sum-of-gradient for the current frame is below the threshold, then the method 600 continues to step 610 where it is determined how many times this condition has been reached (hysteresis). More specifically, the number of times a frame has been below the sum-of-gradient threshold is compared to a threshold value M. If more than M frames have been below the sum-of-gradient threshold, then the method 600 continues to step 612 where the current or power supplied to the actuator of the imaging device is increased. The counter for the number of frames failing to satisfy the sum-of-gradient threshold is then increased at step 614. If less than M frames have been below the sum-of-gradient threshold, then the method 600 skips step 612 and simply increases the counter at step 614. After increasing the counter, the method 600 returns to step 602 and acquires the next frame data.

If the sum-of-gradient for the current frame is above the threshold at step 608, then the method 600 continues to step 616 where the data is loaded into a sum-of-differences algorithm. At step 618, the sum-of-differences is calculated. At step 620, the maximum of the sum-of-differences is identified. At step 622 the maximum sum-of-differences is compared to a threshold. If the maximum sum-of-differences is below the sum-of-differences threshold, then the method 600 continues to step 624 where it is determined how many frames have failed to satisfy the sum-of-differences threshold. More specifically, the number of times a frame has been below the sum-of-differences threshold is compared to a threshold value M. If more than M frames have been below the sum-of-differences threshold, then the method 600 continues to step 626 where the current or power supplied to the actuator of the imaging device is increased. The counter for the number of frames failing to satisfy the sum-of-differences threshold is then increased at step 628. If less than M frames have been below the sum-of-differences threshold, then the method 600 skips step 626 and simply increases the counter at step 628. After increasing the counter at step 628, the method 600 returns to step 602 and acquires the next frame data.

If the maximum sum-of-differences is above the sum-of-differences threshold, then the method 600 moves on to step 630 where the marker location is determined. In that regard, the marker location is determined based on calculation of a mean, median, and/or combinations thereof in some instances. After determining the marker location, the method 600 continues to step 632 where it is determined if the marker location is within an acceptable margin of error (e.g., distance, angle, etc.) around a desired marker position. In the illustrated embodiment, it is presumed that the desired position for detection of the marker is a position that corresponds to a rotation of 120 degrees relative to a starting point of the transducer. Generally, the desired position and the region of error around that position may be considered the target region of the image for the marker. If the marker is within the target region, then the current or power supplied to the actuator of the imaging device is maintained at its current level and the counter is set to 0 in step 634. If the marker is not within the target region, then the method 600 continues to step 636 where it is determined how many frames have failed to have the marker within the target region. More specifically, the number of times a frame has had the marker outside of the target region is compared to a threshold value M. If more than M frames have had the marker outside of the target region, then the method continues to step 638 where the current or power supplied to the actuator of the imaging device is decreased. After decreasing the current or power, the counter for the number of frames failing to satisfy the sum-of-differences threshold is then increased at step 640. If less than M frames have had the marker outside of the target region, then the method 600 skips step 638 and simply increases the counter at step 640. After increasing the counter at step 640, the method 600 returns to step 602 and acquires the next frame data.

Figure 40:
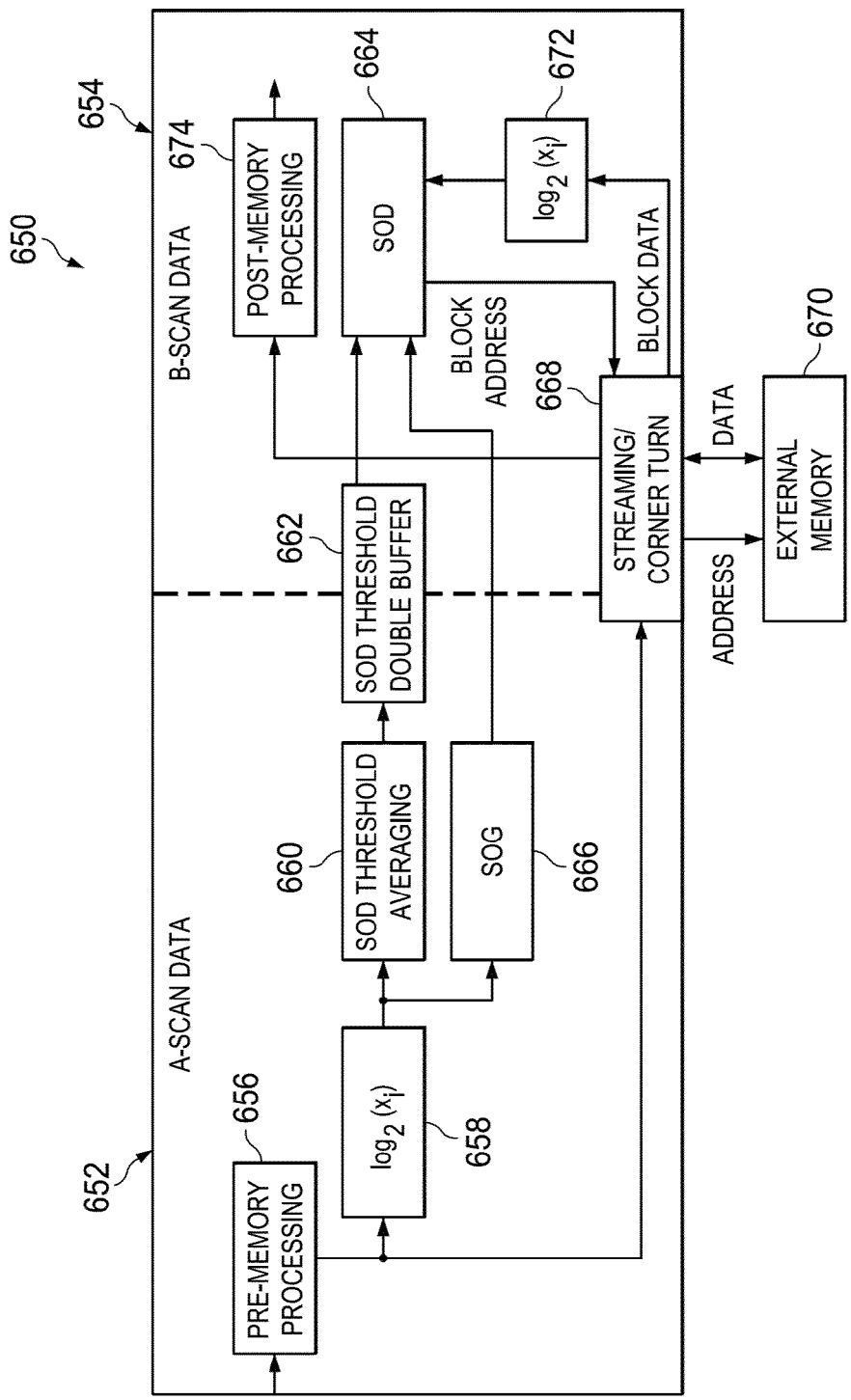
FIG. 40 is a diagrammatic schematic view of a portion of an imaging system illustrating aspects of a sum-of-differences and sum-of-gradient algorithm according to an embodiment of the present disclosure.

While the sum-of-differences and sum-of-gradient algorithms include complex calculations and analysis, embodiments of the present application provide hardware implementations that can determine the marker position utilizing the sum-of-differences and sum-of-gradient algorithms within the same amount of time it takes to perform two B-scans with the scanning mechanism. Referring now to FIG. 40, one such hardware implementation 650 is illustrated. The illustrated hardware architecture is suitable for use with the image processing systems where the "corner-turn" (transpose) operation is performed in hardware, but it should be apparent to a skilled practitioner that the same approach may be readily used for other image acquisition and processing architectures including those that do not utilize a corner turn.

In general, the calculations of the sum-of-gradient and sum-of-differences algorithms (e.g., thresholds, sum-of-gradient, sum-of-differences, etc.) operate on decibel power data for the ultrasound return. While the processing operations typically used to produce images for the clinical operator/end-user involve complex lateral filtering, autocorrelation for color Doppler flow, and other complex processing techniques, such steps are not required for effective field-of-view control. Accordingly, in some implementations of the sum-of-gradient and sum-of-differences algorithms it can be more important that the threshold average and the sum-of-differences operations use the same definition of signal power than that the most accurate signal power information is found for each point.

As shown in FIG. 40, the hardware architecture 650 includes a domain 652 configured to handle the A-scan data and a domain 654 configured to handle the B-scan data. The hardware architecture receives ultrasound or other imaging signals and performs pre-memory processing at 656. A simplified signal power calculation is utilized. In the illustrated embodiment, the power is calculated as $\log_2|x_i\oplus|$ at both 658 and 672, where $x_i$ denotes each pair of I/Q values that comprise the pre-memory-processed ultrasound signal or equivalent of other imaging signals (e.g., the complex Fourier-transform output values of a frequency-domain OCT or other electromagnetic depth imaging signal). Wherever a dBFS (Decibels Relative to Full Scale) value is used in the algorithm (e.g. 2 dBFS), the equivalent digital value would be approximately one-sixth that value (e.g., 2 dBFS≈0.33). Accordingly, if $\log_2(I_i^2+Q_i^2)$ is used to approximate dBFS while eliminating the square-root operation implied by $\log_2|x_i|$, then translating between dBFS and digital values includes both gain and offset terms.

The sum-of-gradient calculation involves a filtering convolution along the B-scan axis that can be performed efficiently on the post-transposed data. However, the sum-of-gradient calculation can also be performed on the A-scan data, as shown at 666. In some instances, the sum-of-gradient calculation is performed with the use of a two-A-scan buffer. If the threshold averaging and the sum-of-gradient operations are both implemented in the A-scan domain 652, then the results can be ready in time for the start of the corresponding sum-of-differences calculations 664 on the same B-scan frame. This approach minimizes latency in the control loop to less than one frame-time (e.g., 50 ms at 20 Hz) from the end of a B-scan to the time the corresponding sum-of-differences result is available to the field-of-view controller. As shown in FIG. 40, the threshold averages are computed for each A-scan at 660 and then written to a FIFO buffer 662 where they can be retrieved by the sum-of-differences module 664. The sum-of-differences calculation can also leverage the corner-turn 668 and external memory 670 and be performed on an entire frame or set of A-scans. In that regard, after passing through the corner turn 668, at least a portion of the imaging data is sent through post-memory processing at 674.

Figure 41:
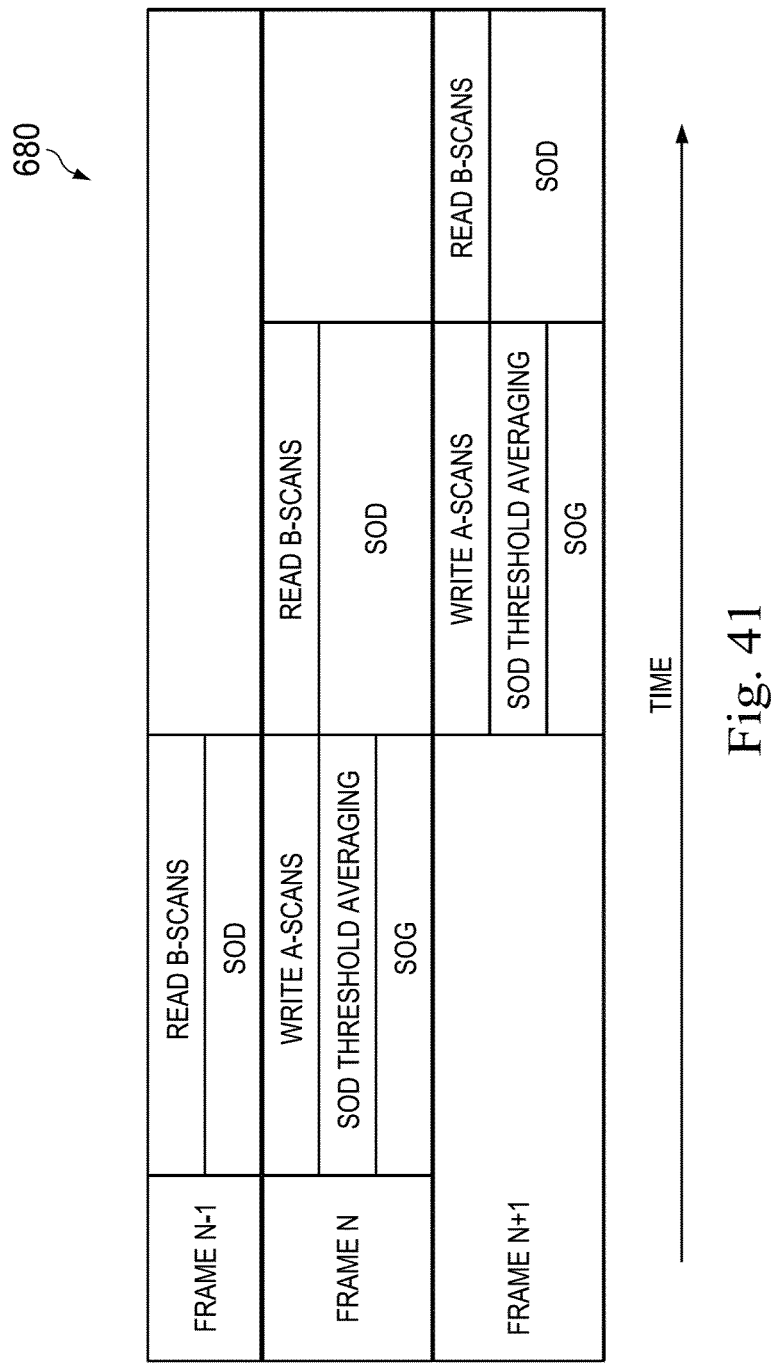
FIG. 41 is a timeline illustrating a timing of processing steps of a sum-of-differences and sum-of-gradient algorithm according to an embodiment of the present disclosure.

If the sum-of-gradient test for a given frame has a negative outcome, then the sum-of-differences calculation can either be bypassed or its output can be dumped. However, when the sum-of-gradient test is successful, then the sum-of-differences calculation is utilized to determine the optimal field-of-view. The threshold averaging may be performed regardless of whether the sum-of-gradient test is met. Accordingly, the threshold averaging is implemented in parallel hardware for best performance in some instances. In that regard, FIG. 41 provides a timeline 680 that illustrates the timing of the operations.

As described, to determine whether a given frame contains an adequate range of motion to find the marker, the sum of horizontal (B-scan-axis) gradient magnitudes over a representative region is calculated. For example, for one exemplary data set, the region of interest was considered to be all samples of rows 150-200 and the average gradient threshold was set to 2 dBFS. In some instances, the gradient filter coefficients are [−1 0 +1] and can be realized by the hardware arrangement shown in FIG. 42. In that regard, as each new A-scan data point arrives at 692, the value from two A-scans previous is just emerging from the 2-A-scan buffer 694 and is subtracted from the new incoming value at 696. This effectively transposes the data into the B-scan domain in a very limited fashion. The relevant subset of these gradient values are summed at 698 and compared against the threshold 702 at 700. As noted above, the threshold value for implementation of one dataset was set to 2 dBFS per point in the sum. In some instances, the kernel is non-normalized with an effective gain of 2, and because the values are being summed rather than averaged, the threshold becomes 4 dBFS times the number of samples in the region of interest. If the sum-of-gradient is below this threshold, then the sum-of-differences calculation should be ignored and the field of view should be expanded so that the marker becomes visible (i.e., the drive current to the transducer deflection mechanism should be increased).

As described in the clamping section of the sum-of-differences algorithm calculations above, the left half of the sum-of-differences region (e.g., the first 180 A-scans of a 360-A-scan image) is summed along the B-scan axis to produce a threshold value for each depth point in the sum-of-differences region (e.g., 45 samples along the A-scan axis as required to cover the intra-window image depth region). This summation can be performed on-the-fly as A-scan data arrives from the processing modules, as shown in the arrangement 710 of FIG. 43. In that regard, a dual-port RAM 712 allows the accumulators for each depth point to be initialized during the first A-scan and updated with each subsequent A-scan until the entire left half of the sum-of-differences region has arrived. As the last A-scan of the left half of the sum-of-differences region arrives, each sum is normalized to form an average. These average values for each of the depth points are then transferred to the sum-of-differences module. A ping-pong double-buffer based on a separate dual-port RAM provides a convenient mechanism for this transfer, as shown in FIG. 40 above. While the sum-of-differences module is using the threshold data from the previous frame, the threshold averaging module may be updating the dataset corresponding to the frame that is currently arriving. In effect, this double buffer is synchronized to the corner-turn buffer, but because it is small and data elements must be read many times it is more efficient to utilize resources within the FPGA or ASIC.

The averaging region can be constrained to a subset that forms a power-of-two number of elements so that no division is required. For example, if the left half of the sum-of-differences region nominally uses 180 of the 360 A-scans in a frame, then only N=128 of those 180 A-scans are averaged in some instances. Alternatively the sum of the region can be multiplied by the reciprocal of the number of accumulated points (with the reciprocal expressed in fixed point representation or floating point representation in some embodiments).

Figure 44:
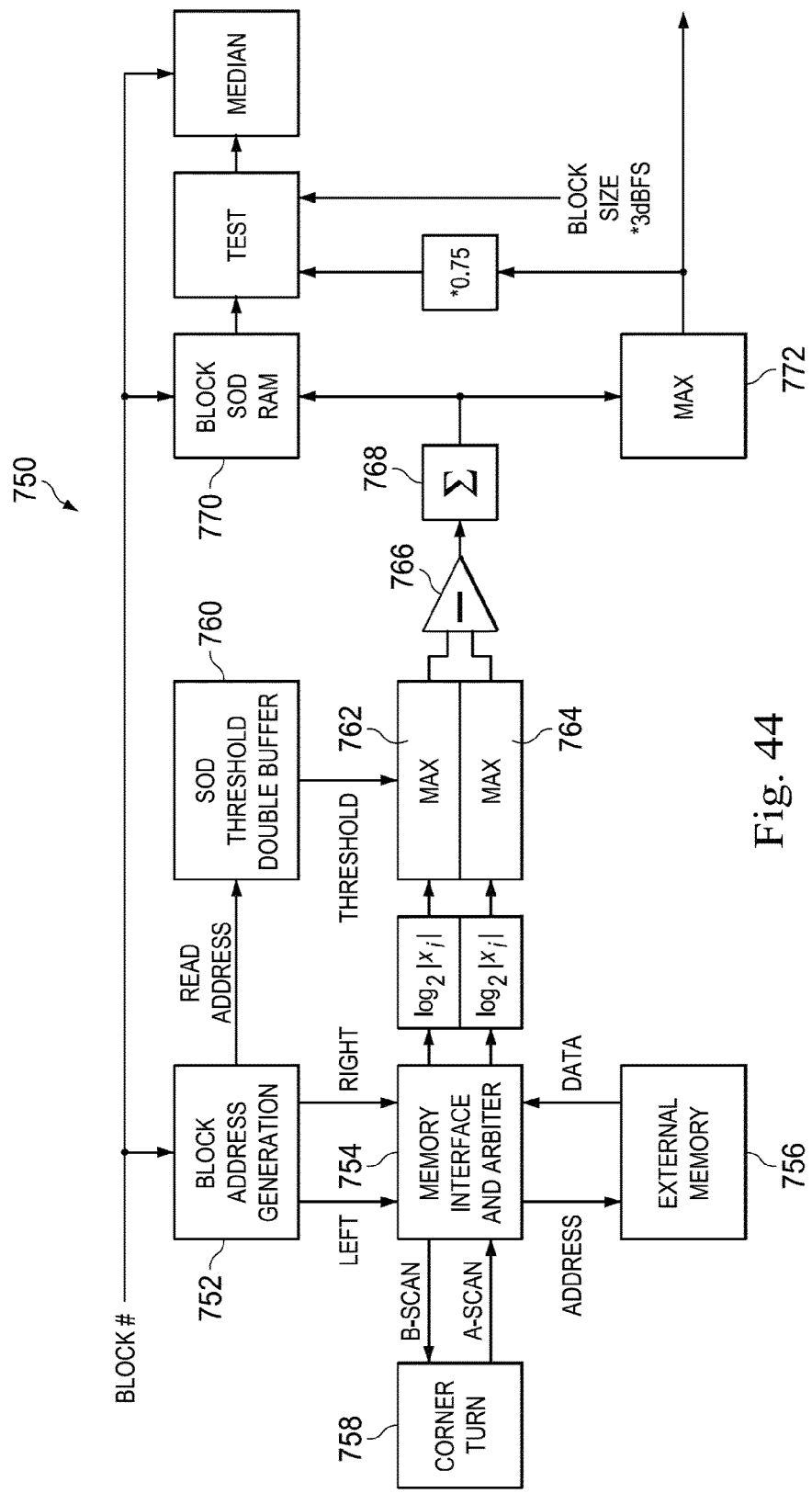
FIG. 44 is a diagrammatic schematic view of a hardware architecture suitable for implementing a sum-of-differences portion of an algorithm according to another embodiment of the present disclosure.

Once the sum-of-gradient and threshold average (clamping) values have been computed and transferred to the B-scan domain as discussed above with respect to FIG. 40, the sum-of-differences calculation is performed. In that regard, FIG. 44 illustrates a module 750 suitable for making the sum-of-differences calculation. As discussed above, the central calculation described above from which the algorithm takes its name is a sum-of-differences between two blocks. The size of the blocks varies based on the imaging device, size of the region of interest, size of the images, and/or other factors. In one embodiment, each block has a size of approximately 20 pixels by 45 pixels, covering a total of 900 pixels. In that regard, the width of each block (e.g., 20 pixels) is a parameter of the sum-of-differences module that is determined by the number of A-scans that are required to span a certain percentage or angle (e.g. 10% or a 10° angle) out of the desired field of view (e.g. 120° field of view). The module 750 is configured to iterate over the possible block locations or block numbers.

The block address generation module 752 takes a block number as input and generates the addresses of the left and right blocks to be differenced. These addresses are fed to a memory interface and arbiter 754 that shares the external memory 758 bandwidth between the corner-turn 758 A-scan write, corner-turn 758 B-scan read, and sum-of-differences block read operations.

The Y addresses (A-scan axis) of each block are fixed. The X addresses (B-scan axis) are given as: Right block X addresses: (location−width+1) to (location+width); and Left block X addresses: [round(location/2)−width+1] to [round (location/2)+width]. Note that the "width" referred to above is half the nominal block width (e.g., 10 versus 20). Rounding division by 2 can be accomplished by adding 1 and then shifting right by 1. Each (X,Y) coordinate translates into a memory offset as follows: Address=(X*A-scan length)+Y.

The block address generation module also outputs the address required to read a threshold from the threshold double-buffer 760 that corresponds to the current depth point along the A-scan axis. As discussed above, this dual-port double-buffer is written by the threshold averaging module. Having a true second port allows the sum-of-differences module to read thresholds at full speed from the "old" half of the buffer even while the threshold averaging module may be writing to the "new" half of the buffer.

Corresponding sample points in the first and second blocks have the same depth (along the A-scan axis) by definition, so the threshold is always the same for each pair of samples read from the external memory 756. Therefore, the same threshold value is fed to two parallel blocks 762, 764 that clamp each of the two corresponding samples to the minimum value for their particular depth at 766. The output of the sum-of-differences calculation 768 feeds an internal memory 770 and a running maximum calculation 772. The maximum 772 is one of two inputs to a thresholding operation that identifies those blocks satisfying the threshold(s). For example, in one embodiment the thresholding operation identifies the blocks whose sum-of-differences is both: ≥75% of the maximum sum-of-differences for this frame and ≥3 dBFS on average. The result of this testing is a stream of logical values, or one bit for each block, indicating whether the block met the threshold(s). In the illustrated embodiment, the marker location is selected as the median of all blocks that meet the thresholds.

In some embodiments, the median is determined by storing the bits in a FIFO while also counting the number of "1" bits encountered, as shown in the arrangement 780 of FIG. 45. Once all of the bits are stored in the FIFO, the count is used to find the median block. There are three possible scenarios: (1) No blocks met the threshold tests: marker not found (if this condition persists for some period of time, then increase the field of view); (2) An odd number of blocks were found (then the same location will be found by both of the paths, and averaging will have no effect); or (3) An even number of blocks were found (then the two center-most locations will be averaged).

Referring now to FIG. 46, the hardware architecture also relies on a control loop 790. A process variable (PV) is determined at 792. In some instances, the process variable is the position of the marker determined above as an integral number of A-scans (or an integral number+0.5 if the median spans two peak points). In some instances, rounding mechanisms (such as floor, ceiling, etc.) are utilized to select the position of the marker. Based on the values of the process variable and the setpoint, a manipulated variable is adjusted at 794. In that regard, in some instances the setpoint is an integral number of A-scans corresponding to the field of view location (e.g., 120 degrees). The objective of the controller is to adjust the manipulated variable to achieve a desired result, such as transducer deflection (actuator) that achieves the optimal or desired field of view. In some instances, to do this as quickly as possible, the relationship between the actuator drive input and field of view location output is characterized and its inverse approximated at 796. This information allows the control system to operate in a linear space that, in turn, maximizes its stable bandwidth. Based on the adjustments to the manipulated variable at 794 and the inverse transform at 796, the transducer is deflected at 798. A new process variable is determined at 792 based on the updated transducer deflection and the process repeats to facilitate control of the field of view of the imaging device.

In some instances, the transducer deflection does not have a well-defined relationship or transfer function between the manipulated variable (MV) (e.g. current or power) and the effect on the process variable (i.e., field of view). For example, the transfer function may not be readily inverted (e.g. due to hysteresis or other memory effects), the transfer function may vary from one interchangeable sensor unit to another such unit; the transfer function may vary over time as a given sensor unit is used; and the transfer function may have both random and deterministic jitter components (fast variations in time).

One way to compensate for these challenges is to make the smallest possible incremental changes in the manipulated variable (MV) in the direction needed to move the PV to the setpoint. This avoids the need for an inverse transformation or approximation, but may put more constraints on the ability of the system to compensate for variations on shorter time scales that may be deterministic (either periodic or serially correlated). Applying PID design techniques to determine the PID parameters results in faster times to achieve the optimal field of view in some instances. Further, modeling and/or locking to deterministic jitter patterns further improves this performance by adding a feed-forward component to the controller.

A cascaded controller may also be used if a secondary parameter can be sensed at a higher rate than the primary parameter (i.e., marker location). For example, if the current flow or total energy delivered to the actuator is predictive of its deflection but the resistance of the actuator varies, causing jitter, then the marker control loop may be used to drive the setpoint of the actuator driver control loop which in turn servos another parameter such as drive voltage, pulse shape, slew rate, or otherwise to achieve the requested current or energy delivery. If the random (i.e. uncompensated) jitter magnitude is known, then PV changes less than this magnitude may need to be suppressed by hysteresis. Another solution that results in a more optimal PID controller is to use gain scheduling to reduce the bandwidth of the controller as the error decreases, but keeping the integral gain parameter $K_i > 0$ to ensure convergence.

In some implementations a Viterbi algorithm is utilized to determine the location of the marker in one or more of the field of view control techniques described above. For example, in some embodiments a Viterbi algorithm is utilized for the field of view control techniques that implement a sum-of-difference algorithm. In that regard, the sum-of-difference algorithm often produces multiple candidate marker locations for every frame processed due to the fact that the width of the marker often spans multiple A-Scans within a frame. However, one of these peaks, and the corresponding A-scan, must be picked as the location of the marker. Several techniques can be used to pick the peak, such as the largest peak, the first peak greater than a threshold, and the median peak of a plurality of candidate peaks. In some instances, these techniques are noisy (e.g., inconsistent from frame to frame) because they do not use any previous marker locations to help determine the current marker location, resulting in marker locations that can vary considerably from frame to frame.

The Viterbi algorithm uses the past history of marker locations to reduce the noise in picking the marker location. More specifically, the marker location is picked by finding the largest value of a merit function. The merit function is computed by taking the values of the candidate marker locations and adding a cost function that punishes jumps in the marker position. In some implementations, the Viterbi algorithm is implemented using one or more of the following steps: obtain the candidate A-scans (e.g., from the sum-of-difference algorithm); input the candidate A-scans into a two-dimensional array where the x direction represents time and the y direction is marker position; update the two-dimensional array after each frame (or at a regular frame interval) so that a time history of marker locations and their relative positions is maintained; once the array is full with the desired amount of time history (e.g., based on threshold timeframe, number of frames, and/or combinations thereof), perform the Viterbi algorithm.

In that regard, for a state space S, initial probabilities $\pi_i$ of being in state I and transition probabilities $\alpha_{i,j}$ of transitioning from state i to state j, where outputs $y_1, \ldots, y_T$ are observed, then the most likely state sequence $x_1, \ldots, x_T$ that produces the observations is given by:

$$V_{1,k} = P(y_1|k) \cdot \pi_k$$

$$V_{1,k} = P(y_1|k) \cdot \max_{x \in S}(\alpha_{x,k} \cdot V_{t-1,x})$$

In that regard, $V_{t,k}$ is the probability of the most probable state sequence for the first t observation that has k as its final state. The Viterbi path is determined by saving past data that remember the state x that was used. Accordingly, letting Ptr(k,t) be the function that returns the value of x used to compute $V_{t,k}$ if $t>1$ and k if $t=1$, then $$x_T = \mathrm{argmax}_{x \in S}(V_{T,x})$$

$$x_{t-1} = Ptr(x_t, t)$$

While these equations have been described, it is understood that any implementation of a Viterbi algorithm may be utilized as will be understood by those skilled in the art. Below, an exemplary implementation of the Viterbi algorithm in the context of the present disclosure is described. Starting with the oldest values in the two-dimensional array, the merit function is calculated for each column of the array. In some instances, the merit function is a combination of the value of the peak and the cost function. For example, in some implementations the merit function is constructed of two terms that are added together for each potential peak location. In some embodiments, the first term is the value of a sum-of-difference calculation normalized by the largest peak to an 8 bit value, and the second term is the cost function that is described below. In that regard, the cost function is chosen as a parabolic shaped function that has a maximum value of 0 at the peak and decreases in y in some implementations. Accordingly, the cost function may be defined by a $2^{nd}$ order equation of the form of $X^2 + X$. This produces a parabolic shaped cost function. In some particular implementations, the cost function equation is implemented as $$X^2/10 - 2X.$$

This particular function scales nicely for 8 bit data. As a result, in some implementations the cost function is a parabola that has a maximum value of zero and tails off to a minimum value of $-255$. This cost function is applied to each line within the array and summed along the time axis. After applying the cost function, the maximum value of the merit function is determined for the newest column in time. The position (e.g., A-scan) corresponding to the maximum value is selected as the location of the marker.

Further, in some instances at least a portion of the return path of the transducer is included in a frame containing the forward path of the transducer, which results in the marker appearing multiple times within a single frame. Techniques of the present disclosure described below can be utilized to take this into account in determining marker location in conjunction with the field of view control algorithms described above. In some implementations it is desirable to focus on the forward scan. Accordingly, by placing a stronger emphasis on the earlier marker locations in the frame, the end of the forward scan can be more accurately determined based on the marker location. In some instances, a first peak bias is added to the field of view control algorithm. For example, in implementations incorporating a Viterbi algorithm the first peak bias is added as an additional term of the Viterbi cost function that biases the selection of the marker location to earlier peaks in the image. In some instances, the early peak bias is a negatively sloped ramp that starts at zero and linearly ramps down to the user set negative value. In some implementations, the value of the peak bias is represented in 8 bits. In some embodiments, the slope of this linear term is determined by finding the location of the first peak in a sum-of-difference calculation and ramping down the bias to the end of all the candidate peak locations. In some instances, the equation for the bias is Bias=(user defined value)/(last peak location−first peak location)*$Y$ where Y is the position of the sum-of-difference peaks. This bias is added on to the cost function, which has the effect to lower the maximum value of the cost function. Accordingly, in some instances the cost function equation becomes $-X^2/10-2X+\text{Bias}$. The amount of bias is set by the user and can be used to construct a function that decreases in time, either linear, or polynomial. This function can then be applied to the set of potential marker locations acquired within a frame, thereby biasing the selected marker location towards the initial potential marker locations that correspond to the end of the forward scan. Those skilled in the art will recognize that if desired this approach can be similarly utilized to identify later peaks, for example where the return scan is of interest.

In another embodiment, a point of symmetry algorithm is used to find the turnaround point of the image to assist in selecting the marker location. In that regard, as the transducer is driven by the actuator it scans across the target in one direction. At some point the actuator cannot continue to drive transducer in the original direction and the return mechanism starts moving the transducer in the opposite direction, imaging a region that the transducer has already swept through. This turnaround point is the point of symmetry. In some implementations, this point is found by computing the correlation coefficient between two sub matrices that are extracted from the marker region of interest as determined by one of the field of view control algorithms described above. Generally, the sub matrices are adjacent to each other so there is a right and left matrix. In some implementations, the right matrix is utilized as the template matrix and flipped across its left boundary or mirrored across its left boundary to define a mirror matrix (i.e., the left matrix) and the cross correlation coefficient is computed between the two matrices. In other implementations, the left matrix is utilized as the template matrix and flipped across its right boundary or mirrored across its right boundary to define a mirror matrix (i.e., the right matrix) and the cross correlation coefficient is computed between the two matrices. A high correlation value indicates high amount of symmetry. Thus, the highest correlation value is associated with the point of symmetry. This additional point of symmetry algorithm may be implemented to avoid keying in on the mirror incident (e.g., as imaged on the return path) of the marker.

In some instances, the point of symmetry algorithm is implemented using one or more of the following steps. Initially, a region of interest is identified (e.g., using one or more the techniques described previously). The region of interest will be utilized to identify the point of symmetry. The region of interest is selected to be a portion of the image that includes the marker. In some instances, the region of interest is the same region of interest that is used in the sum-of-differences calculation. Accordingly, the region of interest can be identified using the same technique as in the sum-of-differences marker detection. In some instances, the region of interest is user selectable.

Figure 47:
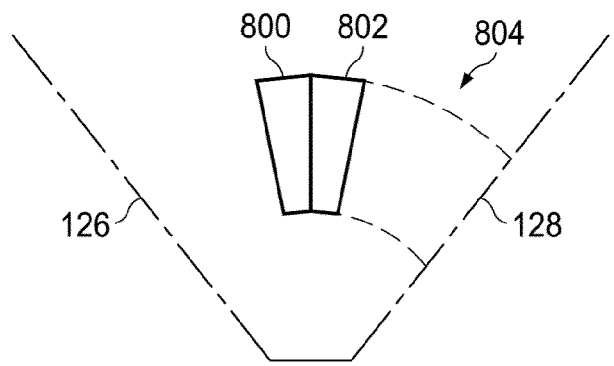
FIG. 47 is a diagrammatic schematic view of an imaging field of view illustrating aspects of a point of symmetry detection algorithm according to an embodiment of the present disclosure.

With the region of interest identified, the mean value for the rows of the image in the region of interest is calculated. In this context, a row represents a single image depth common across multiple A-scans. In that regard, a single A-scan includes image data for a range of depths and each row is associated with a particular depth. In some implementations, the region of interest extends across multiple rows. The mean value is then subtracted from each row in the region of interest to provide a value indicative of the difference relative to the mean value for each row. Two adjacent sub-matrices are defined within the region of interest as described above. For example, as shown in FIG. 47, a field of view having a starting orientation (represented by axis 126) and an ending orientation (represented by axis 128) associated with movement of an imaging transducer has a sub-matrix 800 and an adjacent sub-matrix 802 defined within the region of interest 804. The imaging transducer generally travels between the starting orientation and the ending orientation at an angle between about 1 degree and about 400 degrees, depending on the imaging application. In some instances, the angle is between about 25 degrees and about 360 degrees. In some particular instances, the angle is approximately 120 degrees.

In some instances, the sub-matrix 802 has a fixed angular size by default (i.e., the sub-matrix is comprised of the number of A-scans necessary to cover a specific field of view angle). In that regard, the fixed angular size of the sub-matrix 802 is set in some instances based on an angular width that matches the size of the marker to be detected. In order for the sub-matrices 800, 802 to match each other in the field of view angle represented, the sizes of sub-matrices 800, 802 vary due to the dependence of the angular velocities on position. In that regard, in order to accurately compare the sub-matrices 800, 802, the sub-matrices should cover the same angle in the field of view. Because the angular velocity of the transducer on the forward scan may be different than the angular velocity of the transducer on the return scan (i.e., faster or slower), the amount of time it takes the transducer to traverse a given angle may be correspondingly different between the forward and return scans and/or portions of each of the forward and return scans. For example, the transducer typically has a faster angular velocity at the beginning of the forward scan than at the end of the forward scan. Accordingly, in some instances, one or both of the sub-matrices 800, 802 are sized to cover a specific field of view angle based on the position of the sub-matrix in the field of view of the transducer.

To this end, as has been described above, in some instances the transducer is driven by an actuator to a turnaround point where the actuator stops and moves in the opposite direction where the return motion is controlled by a spring that has been stretched while the actuator was driving the transducer in the forward direction. Often, the return spring imparts a much more constant motion on the transducer than the actuator. As a result, the return motion has a more constant A-line density across multiple scans than the non-linear forward scanning motion of the transducer. Therefore, in some implementations, the size of the sub-matrix 802 is fixed based on the known, relatively constant return motion. On the other hand, the non-linear forward scanning of the actuator produces a lower line density in the beginning of the frame and higher line density at the end of the forward scan due to the decreasing angular velocity of the transducer. Accordingly, the size of sub-matrix 800 can be selected to cover the equivalent field of view angle of sub-matrix 802, for example by up sampling or down sampling the number of A-scans associated with sub-matrix 802. Accordingly, the resulting sizes of the sub-matrices 800, 802 to cover a common field of view angle may consist of a different number of A-scans. In some instances, linear interpolation/decimation is utilized to resize the sub-matrix 800 to match the size of the sub-matrix 802.

In some embodiments, the sub-matrices 800, 802 are defined by starting at the center angle of the region of interest and splitting the matrix encompassing the entire region of interest into the component template sub matrix 802 and the mirror sub matrix 800. With the sub-matrices 800, 802 defined and resized (as necessary) a correlation coefficient between the two sub-matrices is calculated. In some implementations, the correlation coefficient is calculated using at least one of a Pearson product-moment correlation coefficient, a Spearman's rank correlation coefficient, a Kendall Tau rank correlation coefficient, and/or other suitable correlation coefficient calculation technique. Further, in some instances other techniques for evaluating the similarity between data sets are utilized, such as cross-correlation and/or other statistical evaluation techniques.

Figure 48:
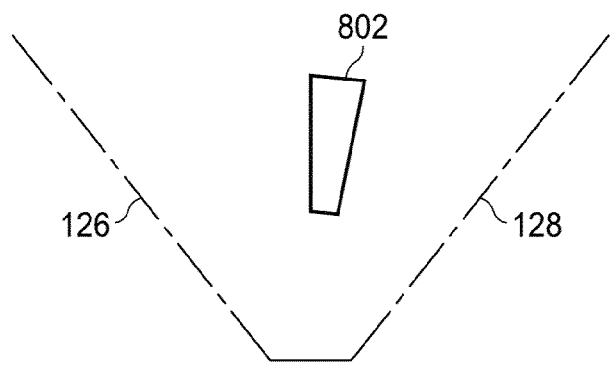
FIG. 48 is a diagrammatic schematic view of an imaging field of view illustrating a template region of a point of symmetry detection algorithm according to an embodiment of the present disclosure.
Figure 49:
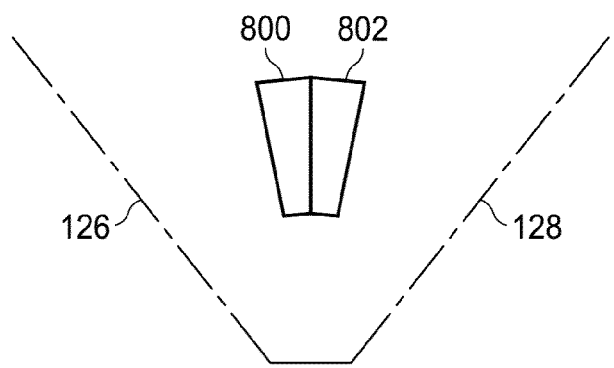
FIG. 49 is a diagrammatic schematic view of the imaging field of view of FIG. 48 illustrating a mirror region adjacent to the template region of the point of symmetry detection algorithm according to an embodiment of the present disclosure.
Figure 50:
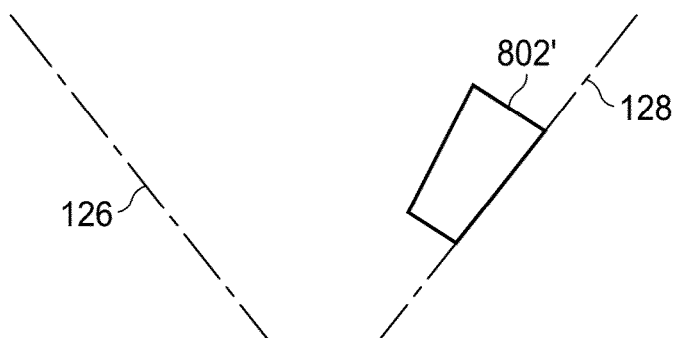
FIG. 50 is a diagrammatic schematic view of the imaging field of view of FIGS. 48 and 49 illustrating a further template region of the point of symmetry detection algorithm according to an embodiment of the present disclosure.
Figure 51:
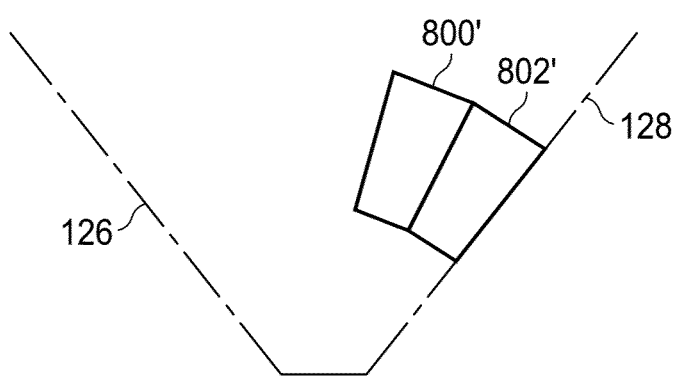
FIG. 51 is a diagrammatic schematic view of the imaging field of view of FIGS. 48-50 illustrating a further minor region adjacent to the further template region of the point of symmetry detection algorithm according to an embodiment of the present disclosure.

After calculation of the correlation coefficient between sub-matrices 800, 802, the axis/angle over which the template matrix is flipped is shifted to the right, for example by a fixed angle amount (e.g., 1 degree, 2 degrees, etc.) or fixed time amount. The template matrix size is adjusted to match the desired field of view angle for the template matrix based on the A-scan line density associated with the new orientation. Similarly, the size of the mirror matrix is adjusted as necessary to match the new template matrix based on the new orientation. With the new sub-matrices defined and resized (as necessary) a correlation coefficient between the two new sub-matrices is calculated. This iterative process (i.e., adjusting the location of the matrices across the region of interest and calculating corresponding correlation coefficients) is repeated across the entire region of interest. In that regard, FIGS. 48-51 generally show aspects of this iterative process. More specifically, FIG. 48 shows the template matrix 802 defined within the region of interest of the field of view of the transducer to cover a desired angle within the field of view, which is based on the angular size of the marker to be detected in some implementations. FIG. 49 shows the mirror matrix 800 being defined by flipping or mirroring the template matrix 802 over the left boundary of the template matrix 802. With the matrix 800 resized, as necessary, to match the desired field of view angle of the template matrix 802, a correlation coefficient is calculated between the matrices 800, 802. Subsequently, the location of the template matrix 802 is moved continuously or step-wise to the right (as shown in FIGS. 48-51) along the path of the transducer through the region of interest. In that regard, FIG. 50 shows the template matrix 802' that is positioned at the far right boundary of the region of interest of the field of view. In other words, template matrix 802' represents the last iteration of the movement of the template matrix 802 across the region of interest. FIG. 51 shows the mirror matrix 800' defined by flipping or mirroring the template matrix 802' over the left boundary of the template matrix 802'. With the matrix 800' resized, as necessary, to match the desired field of view angle of the template matrix 802', a correlation coefficient is calculated between the matrices 800, 802.

By finding the location in the region of interest of the image that produces the largest value of the correlation coefficient between the matrices 800, 802 as the matrices 800, 802 are moved across the region of interest, the point of symmetry is identified. In some implementations, a user supplied threshold is utilized to identify the point of symmetry. For example, in some instances the first location that results in a correlation coefficient meeting and/or exceeding the threshold is identified as the point of symmetry. With the point of symmetry identified, selection of a marker location can be biased to a particular appearance of the marker (e.g., the first occurring or the second occurring) in the image.

Utilizing the field-of-view control techniques described above, scanning mechanism performance can be adjusted in real time to account for device to device variation. In that regard, there are several parameters that contribute to the device to device variation, such as actuator shaft friction, actuator return spring, pre-loading of transducer return spring, transducer height and diameter and housing friction. While effort is made to reduce the variations among these parameters during manufacturing and assembly, it is not possible to completely eliminate the variation. As a result, a time consuming characterization step is typically necessary for every completed imaging device/system in order to determine the scanning performance variation (e.g. scan time, scan velocity) of that particular device/system. In addition to the time it takes to characterize the device/system, the information specific to that device/system must be stored, tracked, and used to run that specific device/system in the future. By utilizing one or more of the markers and associated control techniques described above, the need for characterization and device/system specific information tracking can be eliminated or significantly reduced as at least some of the control techniques themselves provide the necessary calibration of the device/system to ensure optimized imaging performance. In that regard, as described above, the feedback and control mechanisms of the present disclosure can adjust scanning parameters, such as actuator current or actuator current wave form, on the fly to compensate for variations. As a result, any variation that exists between devices (or within a single device over time) is accounted for and adjusted for in real time as the device is used.

Further, the markers and control techniques of the present disclosure are also suitable for reducing image jitter. Image jitter is defined as the variation in the scan angle vs. time between two consecutive frames or groups of consecutive frames. Jitter can be a result of slight changes in the thermal environment or friction experienced during consecutive scans. These variations can be accounted for and compensated for in real time using the field-of-view control mechanisms of the present disclosure. In that regard, image jitter is also a function of scan angle. For example, the last portions of a scan tend to suffer from increased image jitter as compared to the middle portions of the scan. Accordingly, one way to address this issue is to disregard the last portions of a scan, such as the last 1, 5, 10, 15, 20, 25, 30, 35 degrees, or a range defined by two of these values. By not displaying the last portions of the scan, the most problematic jitter area is eliminated. Accordingly, by overdriving the scanning mechanism by the amount of scan angle that will not be displayed to the user, the full field of view is provided to the user without the jitter problems associated with the last portions of the scan. In that regard, the field-of-view control mechanisms described above can be utilized to monitor the amount of scan overdrive (or total rotational motion) and adjust as necessary to achieve the desired realized field-of-view taking into consideration the portion that will be disregarded.

Although the present disclosure has been described primarily in connection with the use of imaging transducers (e.g., devices suitable for ultrasound imaging, optical coherence tomography imaging, and/or other scanning, oscillatory, and rotational imaging modalities), it should be appreciated that the present disclosure can be utilized in other medical devices in which it is desired to provide diagnostic and/or therapeutic procedures utilizing rapid oscillatory motion.

Further, although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

What is claimed is:

1. An imaging device, comprising:
   a flexible elongate member having a proximal portion and a distal portion, the flexible elongate member sized and shaped for use within an internal structure of a patient;

an imaging transducer positioned within the distal portion of the flexible elongate member, the imaging transducer movable along a motion profile; and a housing disposed at the distal portion of the flexible elongate member, the housing comprising a first side including an integrally formed marker within a field of view of the imaging transducer at a predetermined position along the motion profile and an opposite second side that does not include a component within the field of view of the imaging transducer along the motion profile, wherein the integrally formed marker is positioned adjacent to the imaging transducer such that the marker is identifiable in image data obtained by the imaging transducer when the imaging transducer reaches the predetermined position along the motion profile;

wherein the marker includes an inner surface for reflecting energy emitted from the imaging transducer;

wherein a cross-section of the inner surface is curved at a proximal portion and linear at a distal portion; and wherein the inner surface of the marker is located at a shallow depth of focus of the imaging transducer that is outside a target depth of focus of the imaging transducer that contains the internal structure of the patient.

2. The device of claim 1, wherein the predetermined position is a start boundary or an end boundary of the motion profile.

3. The device of claim 2, wherein the motion profile has a desired field of view of between about 30 degrees and about 400 degrees.

4. The device of claim 3, wherein the desired field of view is 120 degrees.

5. The device of claim 3, wherein the desired field of view is 360 degrees.

6. The device of claim 1, wherein the inner surface is planar.

7. The device of claim 1, wherein the inner surface is curved.

8. The device of claim 1, wherein the inner surface of the integrally formed marker extends at an oblique angle with respect to the longitudinal axis of the flexible elongate member such that the distal portion of the inner surface is positioned closer to the longitudinal axis than the proximal portion of the inner surface.

9. The device of claim 8, wherein the oblique angle is between about 1 degrees and about 89 degrees.

10. The device of claim 8, wherein the oblique angle is between about 10 degrees and about 40 degrees.

11. The device of claim 1, wherein a distal end of the inner surface is positioned between about 0.001" and about 0.100" distal of the axis of rotation of the imaging transducer.

12. The device of claim 1, wherein a distal end of the inner surface is positioned at an angle between about 0 degrees and about 75 degrees distally relative to the axis of rotation of the imaging transducer.

13. The device of claim 1, wherein the flexible elongate member has a diameter equal to or less than 4 mm.

14. The system of claim 13, wherein the diameter is equal to or less than 1 mm.

15. The system of claim 14, wherein the diameter is equal to or less than 0.3 mm.

16. The device of claim 1, wherein the inner surface of the integrally formed marker is at least one of planar, concave, or convex.

17. The device of claim 1, wherein the integrally formed marker is secured to the distal portion of the flexible elongate member and is formed of a material having an increased acoustic reflectivity relative to other sections of the distal portion of the flexible elongate member.

18. The device of claim 1, wherein the inner surface of the integrally formed marker extends parallel to the longitudinal axis of the flexible elongate member.

19. The device of claim 1, wherein the integrally formed marker is positioned between about 0.051 mm and about 5 mm from the longitudinal axis of the flexible elongate member.

20. The system of claim 1, wherein the predetermined position occurs when the field of view exceeds a desired field of view and wherein a distal end of the inner surface is positioned beyond an axis of rotation of the imaging transducer along a longitudinal axis of the flexible elongate member when the imaging transducer is within the desired field of view.

21. An imaging system, comprising:
an imaging device including:
a flexible elongate member having a proximal portion and a distal portion, the flexible elongate member sized and shaped for use within an internal structure of a patient;
an imaging transducer positioned within the distal portion of the flexible elongate member, the imaging transducer movable along a motion profile; and
a housing disposed at the distal portion of the flexible elongate member, the housing comprising a first side including an integrally formed marker within a field of view of the imaging transducer at a predetermined position along the motion profile and an opposite second side that does not include a component within the field of view of the imaging transducer along the motion profile, wherein the integrally formed marker positioned adjacent to the imaging transducer such that the marker is identifiable in image data obtained by the imaging transducer when the imaging transducer reaches the predetermined position along the motion profile, wherein the inner surface of the marker is located at a shallow depth of focus of the imaging transducer that is outside a target depth of focus of the imaging transducer that contains the internal structure of the patient, wherein the marker includes an inner surface for reflecting energy emitted from the imaging transducer, wherein a distal end of the inner surface is positioned in alignment with an axis of rotation of the imaging transducer along a longitudinal axis of the flexible elongate member, and wherein a cross-section of the inner surface is curved at a proximal portion and linear at a distal portion; and
a controller in communication with the imaging device, the controller configured to adjust a control signal being provided to an actuator moving the imaging transducer along the motion profile based on identifying the marker within the image data in order to achieve a desired field of view for the imaging transducer as well as the start and end positions of the field of view.

22. The system of claim 21, wherein the predetermined position is a start boundary or an end boundary of the motion profile.

23. The system of claim 22, wherein the motion profile has a desired field of view of between about 30 degrees and about 400 degrees.

24. The system of claim 21, wherein the integrally formed marker is secured to the distal portion of the flexible elongate member and is formed of a material having an increased acoustic reflectivity relative to other sections of the distal portion of the flexible elongate member.

25. The system of claim 21, wherein the integrally formed marker has a simple geometrical profile.

26. The system of claim 21, wherein the inner surface of the marker extends at an oblique angle with respect to the longitudinal axis of the flexible elongate member such that the distal portion of the inner surface is positioned closer to the longitudinal axis than the proximal portion of the inner surface.

27. The system of claim 26, wherein the oblique angle is between about 1 degrees and about 89 degrees.

28. The device of claim 27, wherein the oblique angle is between about 10 degrees and about 40 degrees.

29. The system of claim 21, wherein the inner surface of the integrally formed marker extends parallel to the longitudinal axis of the flexible elongate member.

30. The system of claim 21, wherein the integrally formed marker is positioned between about 0.051 mm and about 5 mm from the longitudinal axis of the flexible elongate member.

31. The system of claim 21, wherein the inner surface of the integrally formed marker is at least one of planar, concave, or convex.

32. The system of claim 21, wherein the flexible elongate member has a diameter equal to or less than 4 mm.

* * * * *